US010508276B2

(12) United States Patent
Lieberman et al.

(10) Patent No.: US 10,508,276 B2
(45) Date of Patent: Dec. 17, 2019

(54) METHODS AND COMPOSITIONS FOR THE PRODUCTION OF SIRNAS

(71) Applicant: CHILDREN'S MEDICAL CENTER CORPORATION, Boston, MA (US)

(72) Inventors: Judy Lieberman, Brookline, MA (US); Linfeng Huang, Quincy, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/804,258

(22) Filed: Nov. 6, 2017

(65) Prior Publication Data

US 2018/0273950 A1    Sep. 27, 2018

Related U.S. Application Data

(63) Continuation of application No. 14/758,924, filed as application No. PCT/US2014/010784 on Jan. 9, 2014, now Pat. No. 9,840,703.

(60) Provisional application No. 61/751,489, filed on Jan. 11, 2013.

(51) Int. Cl.
*C12N 15/113* (2010.01)
*A61K 31/713* (2006.01)
*C12N 15/11* (2006.01)

(52) U.S. Cl.
CPC .......... *C12N 15/113* (2013.01); *A61K 31/713* (2013.01); *C12N 15/111* (2013.01); *H05K 999/99* (2013.01); *C12N 2310/14* (2013.01); *C12N 2330/50* (2013.01); *Y02A 50/473* (2018.01)

(58) Field of Classification Search
None
See application file for complete search history.

(56) References Cited

U.S. PATENT DOCUMENTS

| 2005/0215777 | A1* | 9/2005 | Vargeese | ................ C07H 21/00 536/25.33 |
| 2006/0239971 | A1 | 10/2006 | Mohapatra | |
| 2009/0093026 | A1 | 4/2009 | Dowdy et al. | |
| 2010/0209933 | A1 | 8/2010 | McReynolds et al. | |

FOREIGN PATENT DOCUMENTS

| WO | 2004/011647 A1 | 2/2004 |
| WO | 2007/102140 A2 | 9/2007 |

OTHER PUBLICATIONS

Dasgupta et al., "Genetic uncoupling of the dsRNA—binding and RNA cleavage activities of the *Escherichia coli* endoribonuclease RNase III—the effect of dsRNA binding on gene expression." Molecular microbiology 283 (3):629-640 (1998).
Huang et al., "Production of highly potent recombinant siRNAs in *Escherichia coli*." Nature Protocols 8(12):2325-2336 (2013).
Nakanishi et al. "Structure of yeast Argonaute with guide RNA." Nature 486(7403):368-374 (2012).
Oh et al., "siRNA delivery systems for cancer treatment." Advanced Drug Delivery Reviews 61(10):850-862 (2009).
Park et al. "The multifunctional plant viral suppressor of gene silencing P19 interacts with itself and an RNA binding host protein." Virology 323(1):49-58 (2004).
Xiao et al. "*E. coli* RNase III (E38A) generates discrete-sized products from long dsRNA." RNA 15(5):984-991 (2009).
Zhao et al., "High-throughput screening of effective siRNAs from RNAi libraries delivered via bacterial invasion." Nature Methods 2(12):967-973 (2005).

\* cited by examiner

*Primary Examiner* — J. E Angell
(74) *Attorney, Agent, or Firm* — Nixon Peabody LLP; David S. Resnick; Nicole D. King

(57) ABSTRACT

The technology described herein relates to siRNAs, e.g., methods and compositions relating to the production of siRNAs in bacterial cells.

17 Claims, 34 Drawing Sheets

Specification includes a Sequence Listing.

SEQUENCE LISTING

<160> NUMBER OF SEQ ID NOS: 126

<210> SEQ ID NO 1
<211> LENGTH: 172

```
<212> TYPE: PRT
<213> ORGANISM: Tomato bushy stunt virus

<400> SEQUENCE: 1

Met Glu Arg Ala Ile Gln Gly Asn Asp Ala Arg Glu Gln Ala Asn Ser
1               5                   10                  15

Glu Arg Trp Asp Gly Gly Ser Gly Gly Thr Thr Ser Pro Phe Lys Leu
            20                  25                  30

Pro Asp Glu Ser Pro Ser Trp Thr Glu Trp Arg Leu His Asn Asp Glu
        35                  40                  45

Thr Asn Ser Asn Gln Asp Asn Pro Leu Gly Phe Lys Glu Ser Trp Gly
    50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Phe Gly Phe Asp Gln Ile Gly Cys Thr Tyr
            100                 105                 110

Ser Ile Arg Phe Arg Gly Val Ser Ile Thr Val Ser Gly Gly Ser Arg
        115                 120                 125

Thr Leu Gln His Leu Cys Glu Met Ala Ile Arg Ser Lys Gln Glu Leu
    130                 135                 140

Leu Gln Leu Ala Pro Ile Glu Val Glu Ser Asn Val Ser Arg Gly Cys
145                 150                 155                 160

Pro Glu Gly Thr Glu Thr Phe Glu Lys Glu Ser Glu
                165                 170

<210> SEQ ID NO 2
<211> LENGTH: 226
<212> TYPE: PRT
<213> ORGANISM: Escherichia coli

<400> SEQUENCE: 2

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Glu Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175
```

-continued

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Lys Leu Glu
    210                 215                 220

Leu Glu
225

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Gln Lys Leu Ile Ser Glu Glu Asp Leu
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Ser His Pro Gln Phe Glu Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Tyr Lys Asp Asp Asp Asp Lys
1               5

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Lys Pro Ile Pro Asn Pro Leu Leu Gly Leu Asp Ser Thr
1               5                   10

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uagugguugu cgggcagcag c    21

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uauagacguu guggcuguug    20

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uggucgagcu ggacggcgac g    21

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aatcgctagc atggaacgag ctatacaagg a    31

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aatcggatcc ctcgctttct ttttcgaagg    30

<210> SEQ ID NO 12
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aatcggatcc gatccaaaaa agaagagaaa ggtagatcca aaaagaaga gaaaggta    58

<210> SEQ ID NO 13
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aatcctcgag tcacttatcg tcgtcatcct tgtaatcgcc tacctttctc ttctttt    58

```
<210> SEQ ID NO 14
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aatcgctagc atgcaccacc accaccacca cgcgggcgaa cgagctatac aagga          55

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aatcggatcc tcactcgctt tcttttcga agg                                   33

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccgagtggca ctgagggccg gctacataac gatgagacga attc                      44

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tagccggccc tcagtgccac tcggactttc gtcaggaagt ttga                      44

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gttgtatttg cgggctatct cagatacgac aggacggaag cttc                      44

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tctgagatag cccgcaaata caactttccc gaaaccccag cttt                      44
```

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aatatctaga atggaacgag ctatacaagg a                              31

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aatctctaga tcagtggtgg tggtggtggt g                              31

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aatcggatcc atggaacgag ctatacaagg a                              31

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aatcctcgag tcagtggtgg tggtggtggt gctcgctttc ttttcgaag g         51

<210> SEQ ID NO 24
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
acttgctagc atggattaca aggatgacga cgataagaac cccatcgtaa ttaatcg   57

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atcgggatcc tcattccagc tccagttttt tcaa                           34

```
<210> SEQ ID NO 26
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atcgagctcc cctatagtga gtcgtattag attcagtggt ggtggtggtg gt            52

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
atgaattcgt cgacactgcg gccgctctag agggcccgtt taaacccgct              50

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atctcgagaa tgagctcgct gatcagcggg tttaaacggg ccctctagag              50

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
atcccatatg tcccctatac taggttattg                                    30

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aatcctcgag tcagtggtgg tggtggtggt g                                  31

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aatcgagctc catggtgagc aagggcgagg a                                  31

<210> SEQ ID NO 32
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aatcgcggcc gcatggtgag caagggcgag ga                                    32

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aatcgtcgac ctacttgtac agctcgtcca                                       30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aatcctcgag ctacttgtac agctcgtcca                                       30

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atccgcggcc gcatggtgag caagggcgag gag                                   33

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
atcgagctca tggtgagcaa gggcgaggag                                       30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atcgtcgacc agggtgtcgc cctcgaactt                                       30

<210> SEQ ID NO 38
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atcctcgagc agggtgtcgc cctcgaactt                                        30

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
atccgcggcc gcgtgaaccg catcgagctg aag                                    33

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
atcgagctcg tgaaccgcat cgagctgaag                                        30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
atcgtcgacc tacttgtaca gctcgtccat                                        30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atcctcgagc tacttgtaca gctcgtccat                                        30

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aatcgagctc ccgctacccc gaccacatga a                                      31

<210> SEQ ID NO 44
<211> LENGTH: 34
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 44
aatccgcggc cgcccgctac cccgaccaca tgaa                                  34

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aatcgtcgac gttgccgtcg tccttgaaga a                                     31

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aatcctcgag gttgccgtcg tccttgaaga a                                     31

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aatcgtcgac caacctcagg cggctcatag g                                     31

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aatcctcgag caacctcagg cggctcatag g                                     31

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aatcgcggcc gctactcccc tgccctcaac aagatg                                36

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aatcgagctc tactcccctg ccctcaacaa gatg                                34

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aatcgagctc ggaaaacaga tggcaggtga tg                                  32

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aatcgcggcc gcggaaaaca gatggcaggt gatg                                34

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aatcgtcgac ctagtgtcca ttcattgtgt gg                                  32

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aatcctcgag ctagtgtcca ttcattgtgt gg                                  32

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aatcgagctc caagacccTT gactcagtag cc                                  32

<210> SEQ ID NO 56
<211> LENGTH: 34
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 56
aatcgcggcc gccaagaccc ttgactcagt agcc                                    34

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aatcgtcgac cagctccttc ttatactgct cca                                     33

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aatcctcgag cagctccttc ttatactgct cca                                     33

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aatcgcggcc gctctctgct gctcaagccg cac                                     33

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
aatcgagctc tctctgctgc tcaagccgca c                                       31

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aatcgtcgac aagtctcaaa aggtggtttg cc                                      32

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
aatcctcgag aagtctcaaa aggtggtttg cc                                    32

<210> SEQ ID NO 63
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
atccgcggcc gctgtggcaa agaagggcac acag                                  34

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
atcgagctct gtggcaaaga agggcacaca g                                     31

<210> SEQ ID NO 65
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
atcgtcgact cttctggtgg ggctgttggc t                                     31

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
atcctcgagt cttctggtgg ggctgttggc t                                     31

<210> SEQ ID NO 67
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atccgcggcc gcaagcattg ggaccagcgg ctac                                  34

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 68
atcgagctca agcattggga ccagcggcta c                              31

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
atcgtcgact tattgtgacg aggggtcgtt g                              31

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
atcctcgagt tattgtgacg aggggtcgtt g                              31

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caagcagaag acggcatacg a                                         21

<210> SEQ ID NO 72
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aatgatacgg cgaccaccga caggttcaga gttctacagt ccga                44

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctgggctaca ctgagcacc                                            19

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 74
cactcccaaa acctgctgct gag                                    23

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tctcttcaga agtgcaaggg ta                                     22

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gatgagtaca aaagtcctga tcca                                   24

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ctgcagccac tggttctgt                                         19

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
agacagcaga gcacacaagc                                        20

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
atggttcctt ccggtggt                                          18

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cagcctcttc tccttcctga t                                             21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gccagagggc tgattagaga                                               20

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
agggaaagct agggatggt ttt                                            23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cccaaatgcc agtctctttc tcc                                           23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
aaagagagct aatggatggt ttt                                           23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cccaaatgcc aatctctttc ccc                                           23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aaagaaagct actggttggt gtt                                              23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cccaagtgcc agtcttttc tcc                                               23

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cctaggaaaa agggctgttg ga                                               22

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aggaaggcca gatcttccct aaa                                              23

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gccacaaaaa atcacaagcc a                                                21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ccattgtctg gatttaagcg g                                                21

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
agcagcgtga gtttgagagc                                                  20

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
ccagcttggc agaataagtc tt					22

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
cgaggacaac gacttcgtgt t					21

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
acaatttgcc gtaggtagta tcg					23

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
acagctttga ggtgcgtgtt t					21

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
ccctttcttg cggagattct ct					22

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 98
acgtaaacgg ccacaagttc					20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aagtcgtgct gcttcatgtg                                               20

<210> SEQ ID NO 100
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
actaatacga ctcactatag ggatggtgag caagggcgag ga                      42

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cgtgctgctg cccgacaacc actacct                                       27

<210> SEQ ID NO 102
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gaggtagtgg ttgtcgggca gcagcacg                                      28

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ctacaacagc cacaacgtct atatca                                        26

<210> SEQ ID NO 104
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tgatatagac gttgtggctg ttgtag                                        26

```
<210> SEQ ID NO 105
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cctggtcgag ctggacggcg acgtaa                                              26

<210> SEQ ID NO 106
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ttacgtcgcc gtccagctcg accagg                                              26

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tatgaggaac agattttctc acatgg                                              26

<210> SEQ ID NO 108
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
guucagaguu cuacaguccg acgaucgcuu                                          30

<210> SEQ ID NO 109
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
guucagaguu cuacaguccg acgaucgagu                                          30

<210> SEQ ID NO 110
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
guucagaguu cuacaguccg acgauccguu                                          30

<210> SEQ ID NO 111
```

```
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
guucagaguu cuacaguccg acgaucccgu                                           30

<210> SEQ ID NO 112
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
guucagaguu cuacaguccg acgauccacu                                           30

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(23)
<223> OTHER INFORMATION: Inverted deoxythimidine

<400> SEQUENCE: 113
ucguaugccg ucuucugcuu gut                                                  23

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
ggcuacgucc aggagcgcac c                                                    21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
ugcgcuccug gacguagccu u                                                    21

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 116
guucagaagu acacauccct                                                 20

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
gggaugugua cuucugaact t                                               21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
cagauggcag gugaugauug t                                               21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
aaucagcacc ugccaucugt t                                               21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gauuguacug agagacaggc u                                               21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
```
ccugucucuc aguacaaucu u                                                    21

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 122

His His His His His His
1               5

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gattgtactg agagacagg                                                       19

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gactgcactg aaagacagg                                                       19

<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gactgtactg aaagacagg                                                       19

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
aagtggtcgt tgagggcaat g                                                    21

METHODS AND COMPOSITIONS FOR THE PRODUCTION OF SIRNAS

CROSS-REFERENCE TO RELATED APPLICATIONS

This application is a continuation application of U.S. Ser. No. 14/758,924, filed on Jul. 1, 2015, which is a 35 U.S.C. § 371 National Phase Entry Application of International Application No. PCT/US2014/010784 filed Jan. 9, 2014, which designates the U.S., and which claims benefit under 35 U.S.C. § 119(e) of U.S. Provisional Application No. 61/751,489 filed Jan. 11, 2013, the contents of which are incorporated herein by reference in its entirety.

GOVERNMENT SUPPORT

This invention was made with federal funding under Grant Nos. AI087431 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Jan. 9, 2014, is named 701039-075001-PCT_SL.txt and is 33,506 bytes in size.

TECHNICAL FIELD

The technology described herein relates to methods of producing siRNAs in vivo in bacterial cells.

BACKGROUND

RNA interference (RNAi) by double-stranded (ds) small interfering RNAs (siRNA) suppresses gene expression by inducing the degradation of mRNAs bearing complementary sequences (Fire, A. et al. Nature 1998 391:806-811; Hamilton, A. J. & Baulcombe, D. C. Science 1999 286:950-952). Transfection of synthetic siRNAs into eukaryotic cells to silence genes has become an indispensable tool to investigate gene function, and siRNA-based therapy is being developed to knockdown genes implicated in disease (Elbashir, S. M. et al. Nature 2001, 411:494-8; Caplen, N. J., et al. Proc Natl Acad Sci USA 2001 98:97427; Rettig, G. R. & Behlke, M. A. Mol Ther 2012 20:483-512). More efficient ways to produce siRNAs are desired.

SUMMARY

The technology described herein is directed to methods and compositions relating to the production of active siRNAs generated in vivo, e.g. in bacterial cells.

In one aspect, described herein is a bacterial cell comprising a siRNA-binding polypeptide and a dsRNA comprising a nucleic acid sequence substantially complementary to a target RNA. In some embodiments, the siRNA-binding polypeptide comprises a purification tag. In some embodiments, the siRNA-binding polypeptide is encoded by a nucleic acid. In some embodiments, the siRNA-binding polypeptide is selected from the group consisting of: p19 polypeptide; tombusvirus p19 polypeptide; B2 polypeptide; HC-Pro polypeptide; p38 polypeptide; p122 polypeptide; p130 polypeptide; p21 polypeptide; p1b polypeptide; and NS3 polypeptide. In some embodiments, the dsRNA is greater than 21 nucleotides in length. In some embodiments, the dsRNA is a hairpin RNA. In some embodiments, the bacterial cell expresses an RNase III polypeptide. In some embodiments, the bacterial cell expresses an RNase III polypeptide encoded by an exogenous nucleic acid sequence. In some embodiments, the bacterial cell is an *Escherichia coli* cell. In some embodiments, at least one of the siRNA-binding polypeptide and the dsRNA are constitutively expressed. In some embodiments, at least one of the siRNA-binding polypeptide and the dsRNA are inducibly expressed. In some embodiments, the DNA encoding at least one of the siRNA-binding polypeptide or the dsRNA is part of a plasmid.

In one aspect, described herein is a method of producing one or more siRNA species which can inhibit the expression of a target RNA, the method comprising: culturing a bacterial cell as described herein under conditions suitable for the production of siRNAs. In some embodiments, the method further comprises a second step of isolating the siRNA-binding polypeptide and eluting the siRNAs bound to the siRNA-binding polypeptide. In some embodiments, the method further comprises purifying the siRNAs eluted from the siRNA-binding polypeptide by chromatography e.g. anion exchange HPLC. In some embodiments, the method further comprises contacting the cell with one or more modified nucleotides before or during the culturing step.

In one aspect, described herein is a pharmaceutical composition comprising a siRNA produced according to the methods described herein. In some embodiments, the composition further comprises a population of siRNA species.

In one aspect, described herein is a pharmaceutical composition comprising a siRNA isolated from a bacterial cell as described herein. In some embodiments, the composition further comprises a population of siRNA species.

In one aspect, described herein is the use of a siRNA produced according to the methods described herein in the production of a medicament.

In one aspect, described herein is the use of a siRNA isolated from a bacterial cell of as described herein in the production of a medicament.

In one aspect, described herein is a vector comprising: a nucleic acid encoding a siRNA-binding polypeptide; and a dsRNA cloning site. In some embodiments, the dsRNA cloning site comprises at least one restriction enzyme site and can accept the insertion of at least one nucleic acid sequence such that a dsRNA is encoded and can be expressed. In one aspect, described herein is a vector comprising: a nucleic acid encoding a siRNA-binding polypeptide; and a dsRNA comprising a nucleic acid sequence substantially complementary to a target RNA. In some embodiments, the siRNA-binding polypeptide is selected from the group consisting of: p19 polypeptide; tombusvirus p19 polypeptide; B2 polypeptide; HC-Pro polypeptide; p38 polypeptide; p122 polypeptide; p130 polypeptide; p21 polypeptide; p1b polypeptide; and NS3 polypeptide. In some embodiments, the vector is a plasmid. In some embodiments, the plasmid further comprises a bacterial origin of replication.

In one aspect, described herein is a library of siRNA species, the library comprising: a plurality of clonal bacterial cell populations; wherein each clonal population is comprises bacterial cells as described herein. In one aspect, described herein is a library of siRNA species, the library comprising: a plurality of populations of siRNAs; wherein each population of siRNAs is obtained according to the methods described herein. In some embodiments, each population of siRNAs binds to a single target RNA.

In one aspect, described herein is a kit comprising a bacterial cell as described herein. In one aspect, described herein is a kit for the production of one or more species of siRNA, the kit comprising: a bacterial cell comprising an siRNA-binding polypeptide; and at least one vector comprising a dsRNA cloning site. In one aspect, described herein is a kit for the production of one or more species of siRNA, the kit comprising: a bacterial cell comprising an siRNA-binding polypeptide; and at least one vector comprising a dsRNA comprising a nucleic acid sequence substantially complementary to a target RNA. In one aspect, described herein is a kit comprising a vector as described herein. In one aspect, described herein is a kit for the production of one or more species of siRNA, the kit comprising two vectors; wherein the first vector comprises a nucleic acid encoding a siRNA-binding polypeptide; and wherein the second vector comprises a dsRNA cloning site. In one aspect, described herein is a kit for the production of one or more species of siRNA, the kit comprising two plasmids; wherein the first vector comprises a nucleic acid encoding a siRNA-binding polypeptide; and wherein the second vector comprises a dsRNA comprising a nucleic acid sequence substantially complementary to a target RNA. In some embodiments, at least one vector is a plasmid. In some embodiments, the plasmid further comprises a bacterial origin of replication. In some embodiments, the kit further comprises a bacterial cell. In one aspect, described herein is a kit for the production of one or more species of siRNA, the kit comprising; a bacterial cell comprising a nucleic acid encoding a siRNA-binding polypeptide; and a vector comprising a dsRNA cloning site. In one aspect, described herein is a kit for the production of one or more species of siRNA, the kit comprising; a bacterial cell comprising a nucleic acid encoding a siRNA-binding polypeptide; and a vector comprising a dsRNA comprising a nucleic acid sequence substantially complementary to a target RNA. In some embodiments, the siRNA-binding polypeptide comprises a purification tag. In some embodiments, the siRNA-binding polypeptide is encoded by a nucleic acid. In some embodiments, the bacterial cell expresses an RNase III polypeptide. In some embodiments, the cell is an *Escherichia coli* cell. In some embodiments, at least one of the siRNA-binding polypeptide and the dsRNA are operably linked to a constitutive promoter. In some embodiments, at least one of the siRNA-binding polypeptide and the dsRNA are operably linked to an inducible promoter. In some embodiments, the DNA encoding at least one of the siRNA-binding polypeptide or the dsRNA is part of a plasmid. In one aspect, described herein is a kit comprising the library as described herein.

BRIEF DESCRIPTION OF THE DRAWINGS

FIG. 1A depicts an image of a gel from experiments in which p19-coupled magnetic beads were used to isolate small dsRNAs from total RNA isolated from mammalian ACH2 cells, or from *E. coli* cells, or from *E. coli* cells containing a pcDNA3.1-P19 expression plasmid. Captured RNAs were 5' $^{32}$P-labeled, separated on a native polyacrylamide gel and detected by autoradiography. FIG. 1B depicts images of gels from experiments in which expression of FLAG-tagged p19, but not TREX1 or empty plasmid (V, vector), from pcDNA3.1+ in *E. coli* led to accumulation of ~21 nt RNAs. Total RNAs purified from *E. coli* containing an empty vector, or pcDNA3.1+ expressing FLAG-tagged p19 or TREX1 were separated on a denaturing polyacrylamide gel and stained with SYBR Gold. FLAG immunoblot verified protein expression. FIG. 1C depicts an image of a gel from experiments in which total RNAs purified from *E. coli* containing an empty vector, or pcDNA3.1+ expressing His-tagged p19 or His-tagged p19 mutant proteins defective in RNA binding (Mut1[14]: W39G, W42G and Mut2[16]: K71A, R72G) were separated on a denaturing polyacrylamide gel and stained with SYBR Gold. His immunoblot verified protein expression. FIG. 1D depicts images of gels from experiments in which p19-associated RNAs were isolated with p19-coupled magnetic beads from total RNA extracted from WT *E. coli* (DH5a or MG1655 Δlac) or RNase III mutant strains (in MG1655 Δlac background) expressing the His-tagged p19 protein. p19-captured RNAs were separated on native or denaturing gels and stained with SYBR Gold. p19 expression was verified by His immunoblot. The asterisk (*) indicates equal loading of a background band. FIG. 1E depicts an image of a gel from experiments in which p19-associated RNAs were isolated with p19-coupled magnetic beads from total RNA extracted from p19 expressing *E. coli* WT BL21(DE3) cells or rnc14 mutant HT115(DE3) cells co-transfected with p19 and pcDNA3.1 vector that was empty or encoded Flag-tagged *E. coli* RNase III. p19-captured RNAs were separated on a native polyacrylamide gel and stained with SYBR Gold. p19 and RNase III expression was verified by immunoblots. M, markers. Arrows indicate the ~21 nt small RNA band. Data are representative of at least 2 independent experiments.

FIG. 2A depicts a schematic of pGEX-4T-1-p19-T7 plasmid and the method to produce pro-siRNAs from *E. coli*. FIG. 2B depict an image of a gel from experiments in which anion exchange HPLC fractions of SDS-eluted RNAs (isolated from *E. coli* transformed to express pro-siRNAs) were separated on a native polyacrylamide gel and stained with SYBR Gold. FIG. 2C depicts images of gels from experiments in which nuclease sensitivity assay confirms pro-siRNAs are dsRNAs. Synthetic siRNAs and HPLC purified pro-siRNAs were incubated with nucleases and separated on a native polyacrylamide gel stained with SYBR Gold. FIG. 2D depicts images of gels from experiments in which anti-Ago mAb 2A8 or mouse total IgG was used to immunoprecipitate RNAs in negative control (NC) siRNA or EGFPFL pro-siRNA-transfected HeLa-d1EGFP cells. Immunoprecipitated RNAs were analyzed by Northern blot using a probe complementary to the full length EGFP coding sequence (top) or 5' $^{32}$P end-labeling (middle). Bottom immunoblot is probed for Ago protein. FIG. 2E depicts a graph of the results of qRT-PCR of EGFP expression and EGFP mean fluorescence intensity by flow cytometry in HeLa-d1EGFP cells transfected with either 4 nM of siRNA or pro-siRNAs. Data are normalized to cells treated with negative control (NC) siRNA and are mean±SD of 2 (qRT-PCR) and 3 (EGFP fluorescence) independent experiments. mRNA level is relative to GADPH. FIG. 2F depicts images og gels from experiments in which HPLC-purified pro-siRNAs were separated on native or denaturing polyacrylamide gels stained with SYBR Gold.

FIG. 3A depicts graphs and images of gels from experiments in which qRT-PCR and immunoblot assays of genes targeted for knockdown with the indicated siRNAs or pro-siRNAs, which were transfected (4 nM) into HeLa-d1EGFP (top) or HCT116 (bottom) cells. FIG. 3B depicts graphs of cell counts after transfection with PLK1 siRNA or pro-siRNA (4 nM) or negative control (NC) siRNA or EGFP pro-siRNA as nontargeting controls, respectively. FIG. 3C depicts a schematic and graphs of the results of experiments demonstrating inhibition of HIV-1 spreading by transfection of vif siRNAs and pro-siRNAs (4 nM). vif siRNAs were either individually transfected (vif siRNA-1 and vif siRNA-2) or co-transfected with 2 nM each of vif siRNA-1 and siRNA-2 (vif siRNA1+2). (left) vif mRNA knockdown in HeLa-CD4 cells; (right) infectivity of culture supernatants from transfected HeLa-CD4 cells by TZM-bl assay. FIG. 3D depicts graphs of the suppression of multiple HIV-1 strains by gag pro-siRNAs (transfected at 20 nM). Sequence of gagB siRNA (from IIIB) and its corresponding sequences in UG29 and IN22 strains were shown. (left) bar graph is gag mRNA knockdown in HeLa-CD4 cells (for IIIB), U87.CD4.CXCR4 cells (for UG29) and U87.CD4.CCR5 cells (for IN22); (right) infectivity of culture supernatants by TZM-bl assay. Data are mean±SD of 3 (FIGS. 3A-3C) and 2 (FIG. 3D) independent experiments. mRNA expression and TZM-bl luciferase data are normalized to cells transfected with NC siRNA. FIG. 3D discloses SEQ ID NOS 123-125, respectively, in order of appearance.

FIG. 4A depicts a graph of length distribution of EGFPFL, EGFP100 and LMNA pro-siRNAs assessed by deep sequencing. FIG. 4B depicts a graph of the percentage of sequence content of all aligned deep sequencing reads. FIG. 4C depicts graphs of the distribution of aligned deep sequencing reads of EGFPFL, EGFP100 and LMNA pro-siRNAs. FIG. 4D depicts volcano plots of expression changes versus p value of all annotated transcripts detected by RNA deep sequencing in HeLa-d1EGFP cells transfected with EGFP siRNAs or pro-siRNAs relative to expression in cells transfected with a negative control (NC) siRNA. Arrows indicate EGFP and the number is its fold change. Cut-off of significance is q_value<0.05 (default in Cufflinks). FIG. 4E depicts volcano plots of expression changes (1.2 fold less or more) versus p value detected by microarray in HeLa-d1EGFP cells transfected with LMNA siRNAs or pro-siRNAs relative to expression in cells transfected with a NC siRNA. Arrows indicate LMNA and the number is its fold change. Cut-off of significance is p<0.05 (by paired T-test). FIG. 4F depicts a graph of the percentage of significantly changed transcripts in FIGS. 4D-4E.

FIG. 5A depicts an image of gel demonstrating that approximately 21 nt small RNAs co-purify with p19. *L. monocytogenes* was transformed with an empty vector (pLIV-1) or with pLIV-1 encoding inducible N-terminal His-tagged p19 (pLIV-1-p19-His). Duplicate cultures were grown in the presence of IPTG to induce protein expression. Samples were then lysed and incubated with Ni resin to purify the His-p19 protein and any associated RNAs. p19-bound RNAs were separated on a denaturing polyacrylamide gel stained with SYBR gold. M, RNA markers. Arrow indicates ~21 nt small RNAs. FIG. 5B depicts an image of an immunoblot with His antibody to confirm IPTG-dependent induction of His-p19.

FIG. 6A depicts an image of gel from an experiment in which GST-p19-His protein, induced in *E. coli* with IPTG and purified by imidazole elution from Ni resin, was assayed by SDS-PAGE and Coomassie blue staining FIG. 6B depicts an image of a gel demonstrating that imidazole, but not SDS (0.5%), elutes GST-p19-His protein from Ni beads. Coomassie blue staining of proteins eluted from Ni resin with imidazole (lane 1) or SDS (lane 2). Lane 3 shows proteins bound to the Ni resin before any elution, lane 4 is a sample of the SDS eluate and lane 5 shows proteins remaining on the beads after SDS elution (lane 5). M, protein markers. FIG. 6C depicts an image of a gel demonstrating that SDS elution efficiently elutes GST-p19-His-bound small RNAs. Ni resin was boiled before or after incubation with 0.5% SDS and bound RNAs were analyzed on a denaturing polyacrylamide gel stained with SYBR Gold. Arrow indicates ~21 nt small RNAs, which were removed by SDS treatment. FIG. 6D depicts a schematic summary of the effect of imidazole or SDS elution of material captured by Ni resin from *E. coli* expressing GST-p19-His protein.

FIG. 7A depicts a graph of EGFP fluorescence in HeLa-d1EGFP cells transfected with either siRNAs or pro-siRNAs at the indicated concentrations. Data are a representative dose-response experiment. FIG. 7B depicts schematics and a graph. Schemes of empty, EGFP antisense and hairpin plasmids used to produce pro-siRNAs. Bar graph is the percentage of EGFP expressing HeLa-d1EGFP cells after transfection of NC siRNA and pro-siRNAs (at 0.5 nM). Data are mean±SD of 2 independent transfections.

FIG. 8A depicts a graph of Negative control (NC) siRNA, EGFP siRNA or EGFPFL pro-siRNA co-transfected with pEGFP-N1 plasmid into HCT116 cells that contained a Dicer exon 5 deletion mutation (HCT116 Dicer$^{-/-}$)[19] EGFP knockdown by siRNAs or pro-siRNAs, as measured by flow cytometry, occurred in Dicer-deficient cells. Data are representative of 3 independent experiments. FIG. 8B depicts an image of a gel from experiments in which double stranded RNAs, siRNAs and pro-siRNAs were incubated or not with recombinant Dicer protein for 18 hrs at 37° C. Resulting products were separated on a 20% polyacrylamide gel and stained with SYBR Gold.

FIG. 10A depicts a graph of the results of a qRT-PCR assay of the indicated proinflammatory cytokine gene mRNAs, 4 hr after treatment with the indicated concentrations of LPS, synthetic siRNAs, HPLC-purified pro-siRNAs or SDS-eluate. mRNA levels were normalized to levels in untreated cells. FIG. 10B depicts a graph of the results of a qRT-PCR assay of the indicated proinflammatory cytokine gene, LMNA and IFIT1 mRNAs, 24 hrs after transfection with indicated siRNA and pro-siRNA (at 20 nM). PolyI:C was used as positive control and mRNA levels were normalized to levels in mock transfected cells.

FIG. 12A depicts a graph of the position of DNA oligonucleotides (26-27 nt) used for probing EGFPFL small RNAs compared to position of aligned sequencing reads. The linear scale emphasizes sequencing hot spots. F, forward probe: R, reverse probe. FIG. 12B depicts images of gels from experiments in which purified pro-siRNAs were denatured and incubated with the indicated DNA probes, and then the reaction mixture was analysed for the formation of DNA:RNA hybrids by native polyacrylamide gel electrophoresis and autoradiography. (top) short exposure; (middle) long exposure; (bottom) DNA oligonucleotides only, exposed for 1 hr, to show comparable labelling. Arrows indicate the DNA:RNA hybrids. FIG. 12C depicts a graph of band intensities from FIG. 12B which were quantified using Multi-gauge software (Fujifilm); FIG. 12D depicts a graph of the ratio of sense to antisense signal for each pair of probes calculated by dividing the DNA:RNA hybrid band intensities detected with the "R" oligonucleotide by that detected with the "F" oligonucleotide. FIG. 12E depicts a graph of normalized levels (to Si1) of hybridization signals (from FIG. 12C) and numbers of deep sequencing reads (from Table 2) of the three hot spots.

FIG. 13E depicts a graph comparing deep sequencing reads profiles of pro-siRNAs made from top (1-360 nt, Hotspot-1) or bottom half of EGFP (361-720 nt, Hotspot-2) with pro-siRNAs made from full length EGFP (1-720 nt, EGFPFL-1). In (13D-13E) dashed lines and * highlighted shared hotspots. NC, negative control siRNA FIGS. 14A-14D demonstrate the off-target effect of siRNAs and pro-siRNAs. FIG. 14D depicts Venn diagrams for significantly changed genes in HeLa-d1EGFP cells transfected with LMAN siRNAs or pro-siRNAs.

FIG. 15A depicts a schematic of method to produce pro-siRNAs in E. coli using a two plasmid approach, where one plasmid directs p19 expression and the other expression of dsRNA corresponding to the target sequence. FIG. 15B depicts and image of a gel from experiments in which SDS eluate of pro-siRNAs targeting EGFP, produced using this two-plasmid approach from bacteria transformed with either pRSF-GST-p19-His or pCDF-GST-p19-His (encoding GST-p19-His fusion protein) in combination with L4440-EGFP plasmid (encoding T7-driven sense and antisense EGFP transcripts), were separated on a native polyacrylamide gel stained with SYBR Gold. FIG. 15C depicts graphs of EGFP fluorescence measured by flow cytometry in HeLa-d1EGFP cells transfected with indicated siRNA or pro-siRNA (~10 nM). Data are representative of 3 independent experiments.

DETAILED DESCRIPTION

Figure 1A:
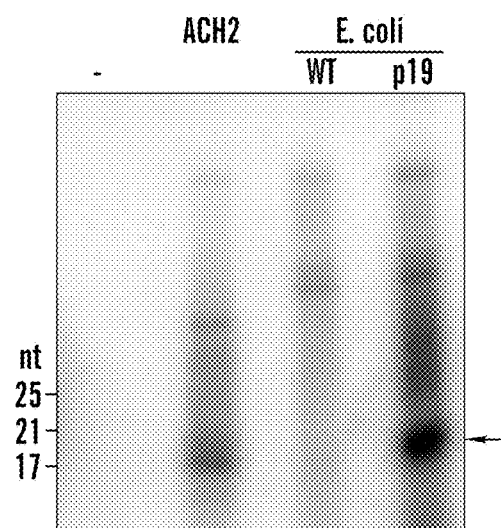
FIGS. 1A-1E demonstrate that ectopic p19 expression captures small RNAs in *E. coli*.

Embodiments of the invention described herein are directed to methods and compositions relating to the production of siRNAs in vivo, e.g. in bacterial cells (siRNAs produced according to the methods and compositions described herein are also referred to herein as "pro-siRNAs"). The technology described herein is derived from the inventors' discovery that prokaryotic cells have the ability to generate siRNAs (e.g. pro-siRNAs). As prokaryotic cells are not known to express components of the canonical RNAi machinery (e.g. Dicer), it was previously believed that prokaryotic cells were incapable of producing siRNAs.

As described in the Examples herein, when the inventors isolated p19 polypeptide which was expressed in a prokaryotic cell, it was found that the p19 polypeptide was bound to siRNAs present in the prokaryotic cell (pro-siRNAs). In the absence of the exogenous p19 polypeptide, these siRNAs are undetectable. These results indicated, in contrast to existing consensus in the field, that prokaryotic cells are capable of generating siRNAs, even in the absence of the canonical siRNA machinery, e.g. Dicer. The results further indicate that the endogenous siRNAs have exceptionally short half-lives which prevent their detection and/or isolation. When the inventors expressed both a p19 polypeptide and a dsRNA having sequence complementary to a target RNA in the prokaryotic cell, siRNAs specific for the target RNA were generated by the prokaryotic cell. The activity of these siRNAs in silencing the target RNA expressed by a eukaryotic cell is demonstrated herein.

Embodiments described herein use endogenous biological processes to generate siRNAs from dsRNA, not requiring the use of algorithms which attempt to predict efficacious siRNA sequences. Embodiments described herein also relate to populations of multiple siRNA species, wherein the population as a whole is specific for a target RNA. Such populations of siRNA species can have reduced off-target effects and greater efficacy than single RNA species.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or at least about 90% or more or any decrease of at least 10% as compared to a reference level. In some embodiments, the terms can represent a 100% decrease, i.e. a non-detectable level as compared to a reference level. In the context of a marker or symptom is meant a statistically significant decrease in such level. The decrease can be, for example, at least 10%, at least 20%, at least 30%, at least 40% or more, and is preferably down to a level accepted as within the range of normal for an individual without such disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. A subject can be male or female.

A "subject in need" of treatment for a particular condition can be a subject having that condition, diagnosed as having that condition, or at risk of developing that condition.

As used herein, the term "proteins" and "polypeptides" are used interchangeably herein to designate a series of amino acid residues connected to the other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA.

The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. A gene may or may not include regions preceding and following the coding region, e.g. 5' untranslated (5'UTR) or "leader" sequences and 3' UTR or "trailer" sequences, as well as intervening sequences (introns) between individual coding segments (exons).

The term "operatively linked" includes having an appropriate start signal (e.g., ATG) in front of the polynucleotide sequence to be expressed, and maintaining the correct reading frame to permit expression of the polynucleotide sequence under the control of the expression control sequence, and, optionally, production of the desired polypeptide encoded by the polynucleotide sequence. In some examples, transcription of a nucleic acid modulatory compound is under the control of a promoter sequence (or other transcriptional regulatory sequence) which controls the expression of the nucleic acid in a cell-type in which expression is intended. It will also be understood that the modulatory nucleic acid can be under the control of transcriptional regulatory sequences which are the same or which are different from those sequences which control transcription of the naturally-occurring form of a protein.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

As used herein, the term "exogenous" refers to a substance (e.g. a nucleic acid or polypeptide) present in a cell other than its native source. The term exogenous can refer to a nucleic acid or a protein (that has been introduced by a process involving the hand of man into a biological system such as a cell or organism in which it is not normally found or in which it is found in undetectable amounts. A substance can be considered exogenous if it is introduced into a cell or an ancestor of the cell that inherits the substance. In contrast, the term "endogenous" refers to a substance that is native to the biological system or cell.

As used herein, the term "complementary" or "complementary base pair" refers to A:T and G:C in DNA and A:U in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U).

As used herein, "substantially complementary" refers to a first nucleotide sequence having at least 90% complementarity over the entire length of the sequence with a second nucleotide sequence, e.g. 90% complementary, 95% complementary, 98% complementary, 99% complementary, or 100% complementary. Two nucleotide sequences can be substantially complementary even if less than 100% of the bases are complementary, e.g. the sequences can be mismatched at certain bases.

As used herein, the terms "gene silencing", "silencing", or "RNAi" refer to a phenomenon where an agent for causing RNAi, such as double-stranded RNA (dsRNA) causes the specific degradation of homologous RNA, thus suppressing the expression of gene products (see Coburn, G. and Cullen, B. (2002) J. of Virology 76:9225). This process has been described in plants, invertebrates, and mammalian cells. An RNAi agent can be substantially homologous to the target RNA gene or genomic sequence, or a fragment thereof. As used in this context, the term "homologous" is defined as being substantially identical, sufficiently complementary, or similar to the target RNA, or a fragment thereof, to effect RNA interference of the target RNA. In addition to native RNA molecules, RNAs suitable for inhibiting or interfering with the expression of a target RNA include RNA derivatives and analogs. RNAi can be caused by any type of interfering RNA, including but are not limited to, siRNA, shRNA, endogenous microRNA and artificial microRNA. In some embodiments, the RNAi molecule is a small interfering RNA (siRNA). An RNAi agent can cause a decrease in the level of a target RNA in a cell by at least about 5%, about 10%, about 20%, about 30%, about 40%, about 50%, about 60%, about 70%, about 80%, about 90%, about 95%, about 99% or more of the target RNA level found in the cell without the presence of the gene silencing agent. In one preferred embodiment, the target RNA levels are decreased by at least about 70%, about 80%, about 90%, about 95%, about 99% or more.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering" refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention can be performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

Embodiments of the technology described herein include methods and compositions relating to a bacterial cell comprising a siRNA-binding polypeptide and a dsRNA; wherein the dsRNA comprises a nucleic acid sequence substantially complementary to at least one target RNA. siRNA-generating enzymes (e.g. RNAses) present in the bacterial cell (e.g. either endogenous or exogenous) can generate siRNA molecules from the dsRNA, which can then be bound by the siRNA-binding polypeptide. The binding of the siRNA-binding polypeptide can enable purification of the siRNA molecules from the other constituents of the bacterial cell and prevent further degradation of the siRNA to non-siRNA constituents, e.g. dsRNAs of less than 15 nucleotides in length or individual ribonucleotides.

As used herein, "double stranded RNA" or "dsRNA" refers to RNA molecules that comprise two substantially complementary strands. Double-stranded molecules include those comprising a single RNA molecule that doubles back on itself to form a two-stranded structure, e.g. a stem-loop molecule or a hairpin molecule. In some embodiments, a dsRNA can comprise nucleic acid sequences which are not substantially complementary to other sequences of the dsRNA (i.e. a single-stranded portion of the dsRNA), for example, the loop part of a stem-loop structure. The portion of the dsRNA which comprises a nucleic acid sequence substantially complementary to a target RNA should comprise, at least in part, the double-stranded portion of a dsRNA. In some embodiments, the double-stranded portion of a dsRNA comprising a nucleic acid sequence substantially complementary to at least one target RNA can be 21 nucleotides in length or greater, e.g. 21 nucleotides or greater, 22 nucleotides or greater, 23 nucleotides or greater, 24 nucleotides or greater, 25 nucleotides or greater, 50 nucleotides or greater, 100 nucleotides or greater, 200 nucleotides or greater, 500 nucleotides or greater, 1000 nucleotides or greater in length.

As used herein, the term "target RNA" refers to a RNA present in a cell (i.e. the "target cell"). The target RNA comprises a target sequence to which one strand of a siRNA according to the methods and compositions described herein binds, thereby causing RNAi silencing of the target RNA. The target cell can be the bacterial cell comprising a siRNA-binding polypeptide or another cell, either prokaryotic or eukaryotic. The target sequence can be an RNA that can be translated (i.e. it can encode a polypeptide, e.g. mRNA) or it can be an RNA that is not translated (i.e. a non-coding RNA). In some embodiments, the target sequence can be any portion of an mRNA. In some embodiments, the target sequence can be a sequence endogenous to the cell. In some embodiments, the target sequence can be a sequence exogenous to the cell. In some embodiments, the target sequence can be sequence from an organism that is pathogenic to the target cell, e.g. the target sequence can be sequence from a viral, bacterial, fungal, and/or parasitic origin. In some embodiments, the target sequence is a viral nucleotide sequence.

In some embodiments, a nucleic acid sequence substantially complementary to a target RNA can comprise a nucleic acid sequence substantially complementary to part or all of the sequence of the target RNA. In some embodiments, a dsRNA comprising a nucleic acid sequence substantially complementary to a target RNA can comprise sequence complementary to part or all of a specific allele, variant, and/or mutation (e.g., insertions, deletions, fusions, SNPs, etc.) of a target RNA. In some embodiments, the dsRNA comprising a nucleic acid sequence substantially complementary to a target RNA can comprise nucleic acid sequence(s) substantially complementary to multiple target RNAs (e.g. target RNAs encoding separate genes or target RNAs encoding multiple variants of the same gene). In some embodiments, a dsRNA comprising a nucleic acid sequence substantially complementary to a target RNA can comprise a nucleic acid sequence substantially complementary to all or part of one or more exons of a target mRNA. In some embodiments, a dsRNA comprising a nucleic acid sequence substantially complementary to a target RNA can comprise a nucleic acid sequence substantially complementary to a cDNA. In some embodiments, a dsRNA comprising a nucleic acid sequence substantially complementary to a target RNA can comprise a nucleic acid sequence (or its complement) obtained from the transcriptome and/or genome of a cell.

In some embodiments, the dsRNA can comprise two separate complementary strands, e.g. a sense and antisense strand.

In some embodiments, the dsRNA can be a hairpin RNA, i.e. an RNA comprising two portions which are reverse complements, separated by a sequence which will not self-anneal, thus forming a stem-loop or "hairpin" structure. In some embodiments, the double-stranded portion of a hairpin RNA can be at least 19 nucleotides in length. In some embodiments, the double-stranded portion of a hairpin RNA can be at least 25 nucleotides in length. In some embodiments, the double-stranded portion of a hairpin RNA can be 30 nucleotides in length or greater, e.g. at least 30 nucleotides, at least 50 nucleotides, at least 100 nucleotides, at least 200 nucleotides, or at least 300 nucleotides. In some embodiments, the dsRNA can be a shRNA. As used herein "shRNA" or "small hairpin RNA" (also called stem loop) is a type of dsRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

In some embodiments, increased length of the double-stranded portion of a dsRNA can correlate with a decreased level of off-target effects, e.g. silencing of non-targeted genes. In some embodiments, one strand of the double-stranded portion of a dsRNA can be at least 100 nucleotides in length. For example, one strand of the double-stranded portion of a dsRNA can be at least 100 nucleotides in length, at least 200 nucleotides in length, at least 300 nucleotides in length, at least 400 nucleotides in length, at least 500 nucleotides in length, at least 700 nucleotides in length, or at least 1000 nucleotides in length.

In some embodiments, the dsRNA can be exogenous to the cell. In some embodiments, the target sequence of the target RNA can be exogenous to the cell. In some embodiments, the target RNA can be exogenous to the cell. In some embodiments, the nucleic acid sequence substantially complementary to a target RNA can be exogenous to the cell.

In the methods and compositions described herein, siRNAs can be generated from the dsRNA comprising a nucleic acid sequence substantially complementary to a target RNA. As used herein, the term "siRNA" refers to a nucleic acid that forms an RNA molecule comprising two individual strands of RNA which are substantially complementary to each other. Typically, the siRNA is at least about 15-40 nucleotides in length (e.g., each complementary sequence of the double stranded siRNA is about 15-40 nucleotides in length, and the double stranded siRNA is about 15-40 base pairs in length, preferably about 19-25 base nucleotides, e.g., 19, 20, 21, 22, 23, 24, or 25 nucleotides in length). In some embodiments, a siRNA can be blunt-ended. In some embodiments, a siRNA can comprise a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. The siRNA molecules can also comprise a 3' hydroxyl group. In some embodiments, the siRNA can comprise a 5' phosphate group. A siRNA has the ability to reduce or inhibit expression of a gene or target RNA when the siRNA is present or expressed in the same cell as the target gene, e.g. the target RNA. siRNA-dependent post-transcriptional silencing of gene expression involves cutting the target RNA molecule at a site guided by the siRNA.

In some embodiments, a single siRNA species can be generated from a dsRNA. In some embodiments, multiple siRNA species can be generated from a dsRNA. For example, two or more siRNA species can be generated from a dsRNA, e.g. two or more siRNA species, three or more siRNA species, five or more siRNA species, or ten or more siRNA species. As used herein, the term "a siRNA species" refers to one or more siRNA molecules which are identical in sequence. In embodiments where multiple siRNA species are generated from a single dsRNA, the species can comprise sequence complementary to the same target RNA or to separate target RNAs. In some embodiments, a single dsRNA can comprise sequence complementary to multiple target RNAs. In some embodiments, a single dsRNA can comprise multiple sequences, each of which is complementary to a unique target RNA, e.g. a multiplicity of siRNA species targeting (e.g. complementary to) a multiplicity of target RNAs can be generated from a single dsRNA.

In the methods and compositions described herein, a dsRNA present within a bacterial cell can be cleaved to generate one or more siRNA species. The siRNA molecules can then be bound by a siRNA-binding polypeptide also present within the bacterial cell. As used herein, the term "siRNA-binding polypeptide" refers to a polypeptide capable of binding to siRNAs and increasing the half-life or detectable level of siRNAs in a prokaryotic cell. In some embodiments, the siRNA-binding polypeptide can bind preferentially or specifically to siRNAs as compared to other dsRNA species, e.g. the polypeptide can bind preferentially or specifically to siRNAs as compared to dsRNAs greater than 25 or less than 15 nucleotides in size. In some embodiments, the siRNA-binding polypeptide can bind preferentially or specifically to siRNAs as compared to other dsRNA species, e.g. dsRNAs greater than 25 or less than 15 nucleotides in size. In one embodiment, the siRNA-binding polypeptide does not bind to dsRNA having a double-stranded portion longer than 25 nucleotides in length. In some embodiments, the siRNA-binding polypeptide can bind preferentially or specifically to siRNAs as compared to single-stranded RNA species.

In some embodiments, a siRNA-binding polypeptide can detectably bind to a siRNA. In some embodiments, a siRNA-binding polypeptide can be a polypeptide that when expressed in a bacterial cell, can cause detectable levels of siRNAs to be present in that cell when detectable levels of siRNAs are not present in the wild-type bacterial cell. In some embodiments, a siRNA-binding polypeptide can be a polypeptide that increases the half-life or detectable level of siRNAs in a prokaryotic cell by at least 5%, e.g. by at least 5%, by at least 10%, by at least 20%, by at least 30%, by at least 50%, by at least 75%, by at least 100%, by at least 200% or more.

In some embodiments, a siRNA-binding polypeptide can be a p19 polypeptide. As used herein, the term "p19" refers to a viral protein which binds specifically to dsRNAs and which suppresses RNAi-mediated host plant viral defenses. The sequences of p19 polypeptides from a number of species are known, e.g. tombusvirus p19 (NCBI Gene ID: 1493957; SEQ ID NO:1). In some embodiments, the p19 polypeptide can be tombusvirus p19. Non-limiting examples of p19 homologues include Carnation Italian ringspot virus P19; Tomato bushy stunt virus p19; Artichoke mottled crinkle virus p19; Lisianthus necrosis virus p19; Pear latent virus p19; Cucumber Bulgarian virus p19; Cucumber necrosis virus p19; Pelargonium necrotic spot virus p19; Cymbidium ringspot virus p19; Lisianthus necrosis virus p19; Lettuce necrotic stunt virus p19; Maize necrotic streak virus p19; Grapevine Algerian necrosis virus p19; and Grapevine Algerian latent virus p19. A p19 polypeptide can comprise mutants, variants, homologues, and functional fragments of wildtype p19 polypeptides.

Further non-limiting examples of an siRNA-binding polypeptide can include the Flock house virus B2; HC-Pro; Tobacco etch virus HC-Pro; P38; P122; P130; Tobamovirus P122/P130; p21; Rice hoja blanca tenuivirus (RHBV) NS3; Cucumber vein yellowing virus P1b; HC-Pro of potyviruses; p21 of Beet yellows virus and Closterovirus; and variants, homologues, or functional fragments of the foregoing.

In some embodiments, an siRNA-binding polypeptide can be an enzymatically inactive member of the RISC complex, e.g. an enzymatically inactive variant or mutant of Argonaute or Dicer (see, e.g. Buker et al. Nat Struct Mol Bio 2007 14:200-7 and Liu et al. Molecular Cell 2012 46:1-11; which are incorporated by reference herein in their entireties). In some embodiments, the siRNA-binding polypeptide is not an enzymatically active member of the RISC complex, e.g. an Argonaute or RISC polypeptide. As used herein, the term "RISC complex" refers to the proteins and single-stranded polynucleotides that interact to recognize target RNA molecules. Demonstrated components of RISC include the Argonaute proteins (e.g. Aubergine; Argonaute 2), R2D2, and Dicer (e.g. Der-2). In the case of an active. RISC complex loaded with a single-stranded guide RNA derived from a siRNA, the RISC complex can cleave the target RNA molecule.

In some embodiments, a siRNA-binding polypeptide can be a polypeptide that can bind to nucleic acids, e.g. protamine, or a variant, homologue, or functional fragment thereof (see, e.g. Rossi. Nature Biotechnology 2005 23:682-4 and Reischl et al. Scientia Pharmaceutica 2010 78:686; which are incorporated by reference herein in their entirety). In some embodiments, a siRNA-binding polypeptide can be a polypeptide that can be bind to dsRNAs, e.g. TARBP2 or a polypeptide comprising a double-stranded RNA binding domain (see, e.g. US Patent Publication 2009/0093026; which is incorporated by reference herein in its entirety) or a variant, homologue, or functional fragment thereof.

A functional fragment of a siRNA-binding polypeptide can be any portion of a siRNA-binding polypeptide which retains at least 50% of the wild-type level of siRNA binding activity, e.g. at least 50%, at least 60%, at least 70%, at least 80%, at least 90%, at least 95%, at least 98%, or more.

In some embodiments, a siRNA-binding polypeptide can comprise a purification tag. The term "purification tag" as used herein refers to any peptide sequence suitable for purification of a siRNA-binding polypeptide, and optionally, siRNAs bound by the siRNA-binding polypeptide. The purification tag specifically binds to (or is bound by) another moiety with affinity for the purification tag. Such moieties which specifically bind to a purification tag can be attached to a matrix or a resin, e.g. agarose beads. Moieties which specifically bind to purification tags can include antibodies, nickel or cobalt ions or resins, biotin, amylose, maltose, and cyclodextrin. Exemplary purification tags can include histidine tags (such as a hexahistidine peptide (SEQ ID NO: 122)), which will bind to metal ions such as nickel or cobalt ions. Therefore, in certain embodiments the purification tag can comprise a peptide sequence which specifically binds metal ions. Other exemplary purification tags are the myc tag (EQKLISEEDL (SEQ ID NO:3)), the Strep tag (WSHPQFEK (SEQ ID NO:4)), the Flag tag (DYKDDDDK (SEQ ID NO:5)) and the V5 tag (GKPIPNPLLGLDST (SEQ ID NO:6)). The term "purification tag" also includes "epitope tags", i.e. peptide sequences which are specifically recognized by antibodies. Exemplary epitope tags can include the FLAG tag, which is specifically recognized by a monoclonal anti-FLAG antibody. The peptide sequence recognized by the anti-FLAG antibody consists of the sequence DYKDDDDK (SEQ ID NO: 5) or a substantially identical variant thereof. Therefore, in certain embodiments the purification tag can comprise a peptide sequence which is specifically recognized by an antibody. The term "purification tag" also includes substantially identical variants of purification tags. "Substantially identical variant" as used herein refers to derivatives or fragments of purification tags which are modified compared to the original purification tag (e.g. via amino acid substitutions, deletions or insertions), but which retain the property of the purification tag of specifically binding to a moiety which specifically recognizes the purification tag. In some embodiments, the siRNA-binding polypeptide can be a p19 fusion protein as described in US Patent Publication 2010/0209933; which is incorporated herein by reference in its entirety.

In some embodiments, the siRNA-binding polypeptide can be encoded by a nucleic acid present in the bacterial cell, i.e. the polypeptide is transcribed and translated by the bacterial cell. In some embodiments, the siRNA-binding polypeptide can be introduced into the bacterial cell as a polypeptide. Uptake of polypeptides can be induced by any means in the art. Non-limiting examples include the protocols described in Shellman and Pettijohn. J Bacteriology 1991 173:3047-3059; which is incorporated by reference herein in its entirety.

In some embodiments, a nucleic acid encoding a siRNA-binding polypeptide and/or a nucleic acid encoding a dsRNA can be present within the bacterial genome, e.g. the nucleic acids can be incorporated into the genome. In some embodiments, a nucleic acid encoding a siRNA-binding polypeptide and/or a nucleic acid encoding a dsRNA can be present within a vector. In some embodiments, a nucleic acid encoding a siRNA-binding polypeptide and/or a nucleic acid encoding a dsRNA can be present within portions of the same vector. In some embodiments, the nucleic acids encoding the siRNA-binding polypeptide and the dsRNA can be present within portions of separate vectors.

The term "vector", as used herein, refers to a nucleic acid construct designed for delivery to a host cell or transfer between different host cells. As used herein, a vector can be viral or non-viral. Many vectors useful for transferring exogenous genes into target cells are available, e.g. the vectors may be episomal, e.g., plasmids, virus derived vectors or may be integrated into the target cell genome, through homologous recombination or random integration. In some embodiments, a vector can be an expression vector. As used herein, the term "expression vector" refers to a vector that has the ability to incorporate and express heterologous nucleic acid fragments in a cell. An expression vector may comprise additional elements, for example, the expression vector may have two replication systems, thus allowing it to be maintained in two organisms. The nucleic acid incorporated into the vector can be operatively linked to an expression control sequence when the expression control sequence controls and regulates the transcription and translation of that polynucleotide sequence. In some embodiments, the dsRNA and the nucleic acid encoding the siRNA-binding polypeptide can be within the same operon. In some embodiments, the dsRNA and the nucleic acid encoding the siRNA-binding polypeptide can be within separate operons.

In some embodiments, a siRNA-binding polypeptide and/or dsRNA encoded by a nucleic acid can be present within a portion of a plasmid. Plasmid vectors can include, but are not limited to, pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," *Gene Expression Technology*, vol. 185 (1990), which is hereby incorporated by reference in its entirety).

As used herein, the term "viral vector" refers to a nucleic acid vector construct that includes at least one element of viral origin and has the capacity to be packaged into a viral vector particle. The viral vector can contain a transgenic gene in place of non-essential viral genes. The vector and/or particle may be utilized for the purpose of transferring any nucleic acids into cells either in vitro or in vivo. Numerous viral vectors are known in the art and can be used as carriers of a nucleic acid into a cell, e.g. lambda vector system gt11, gt WES.tB, Charon 4.

In accordance with the methods and compositions described herein, siRNAs specific for the target RNA can be produced in a bacterial cell when both the dsRNA and the siRNA-binding polypeptide are present and/or expressed. In some embodiments, the dsRNA and/or the siRNA-binding polypeptide can be constitutively expressed. In some embodiments, nucleic acids encoding the dsRNA and/or the siRNA-binding polypeptide can be operably linked to a constitutive promoter. In some embodiments, the dsRNA and/or the siRNA-binding polypeptide can be inducibly expressed. In some embodiments, nucleic acids encoding the dsRNA and/or the siRNA-binding polypeptide can be operably linked to an inducible promoter.

As described herein, an "inducible promoter" is one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, and tetracycline, steroid-responsive promoters, rapamycin responsive promoters and the like. Inducible promoters for use in prokaryotic systems are well known in the art, see, e.g. the beta.-lactamase and lactose promoter systems (Chang et al., Nature, 275: 615 (1978, which is incorporated herein by reference); Goeddel et al., Nature, 281: 544 (1979), which is incorporated herein by reference), the arabinose promoter system, including the araBAD promoter (Guzman et al., J. Bacteriol., 174: 7716-7728 (1992), which is incorporated herein by reference; Guzman et al., J. Bacteriol., 177: 4121-4130 (1995), which is incorporated herein by reference; Siegele and Hu, Proc. Natl. Acad. Sci. USA, 94: 8168-8172 (1997), which is incorporated herein by reference), the rhamnose promoter (Haldimann et al., S. Bacteriol., 180: 12774286 (1998), which is incorporated herein by reference), the alkaline phosphatase promoter, tryptophan (trp) promoter system (Goeddel, Nucleic Acids Res., 8: 4057 (1980), which is incorporated herein by reference), the $P_{LtetO-1}$ and $P_{lac/are-1}$ promoters (Lutz and Bujard, Nucleic Acids Res., 25: 1203-1210 (1997), which is incorporated herein by reference), and hybrid promoters such as the tac promoter. deBoer et al., Proc. Natl. Acad. Sci. USA, 80: 21-25 (1983), which is incorporated herein by reference.

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including $Cu^{2+}$ and $Zn^{2+}$), galactose, tetracycline, IPTG (isopropyl-β-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause the dissociation of the tet repressor from the engineered promoter and allow transcription of the sequence downstream of the engineered promoter to occur.

A bacterial cell of the methods and compositions described herein can be any of any species. Preferably, the bacterial cells are of a species and/or strain which is amenable to culture and genetic manipulation. In some embodiments, the bacterial cell can be a gram-positive bacterial cell. In some embodiments, the bacterial cell can be a gram-negative bacterial cell. In some embodiments, the parental strain of the bacterial cell of the technology described herein can be a strain optimized for protein expression. Non-limiting examples of bacterial species and strains suitable for use in the present technologies include *Escherichia coli, E. coli* BL21, *E. coli* Tuner, *E. coli* Rosetta, *E. coli* JM101, and derivatives of any of the foregoing. Bacterial strains for protein expression are commercially available, e.g. EXPRESS™ Competent *E. coli* (Cat. No. C2523; New England Biosciences; Ipswich, Mass.).

A dsRNA comprising a nucleic acid sequence substantially complementary to a target RNA can be processed to create siRNA molecules by a siRNA-generating enzyme (e.g. RNAse III) present within the bacterial cell. In some embodiments, the bacterial cell can be a cell which expresses a siRNA-generating polypeptide. In some embodiments, the bacterial cell can be a cell which overexpresses a siRNA-generating polypeptide. As used herein, a "siRNA-generating polypeptide" refers to an enzyme with RNase activity which can cleave dsRNA in such a way that siRNAs result. In some embodiments, the siRNA-generating polypeptide can be an RNaseIII polypeptide. As used herein the term "RNaseIII polypeptide" refers to a eukaryotic class I RNase III, e.g. *E. coli* RNaseIII (NCBI Gene ID: 947033; SEQ ID NO: 2). siRNA-generating polypeptides can be mutants, variants, homologues, or functional fragments of wildtype siRNA-generating polypeptides which retain at least 50% of the siRNA generating activity of the wildtype, e.g. at least 50%, at least 60%, at least 70%, at least 80%, at least 90% or more of the wildtype activity. In some embodiments, the siRNA-generating enzyme can be endogenous to the bacterial cell. In some embodiments, the siRNA-generating enzyme can be exogenous to the bacterial cell.

In some embodiments, a cell can comprise a mutation and/or transgene which enhances the expression and/or activity of a siRNA-generating polypeptide. By way of non-limiting example, a cell can comprise a mutation in the endogenous RNaseIII promoter which increases expression, or a cell can comprise a transgenic (e.g. exogenous) construct with an RNaseIII gene under the control of a strong constitutive or inducible promoter, or a cell can comprise a nucleic acid encoding a polypeptide which increases the activity and/or expression of RNaseIII, e.g. the T4 polynucleotide kinase/phosphatase (PNK) (see Durand et al. PNAS 2012 109:7073-8; which is incorporated by reference herein in its entirety). In some embodiments, a cell can express an ectopic level and/or amount of a siRNA-generating polypeptide (e.g. RNaseIII). As used herein, "ectopic" refers to a substance that is found in an unusual location and/or amount. An ectopic substance can be one that is normally found in a given cell, but at a lower amount and/or at a different time.

In one aspect, the technology described herein relates to a method of producing one or more siRNA species which can inhibit the expression of a target RNA, the method comprising culturing a bacterial cell comprising at least a siRNA-binding polypeptide and a dsRNA wherein the dsRNA comprises a nucleic acid sequence substantially complementary to a target RNA under conditions suitable for the production of siRNAs. As used herein, the term "conditions suitable for the production of siRNAs" refers to conditions under which a siRNA-generating enzyme within a bacterial cell cleaves the dsRNA in the presence of a siRNA-binding polypeptide. In embodiments wherein one or more of the dsRNA and the siRNA-binding polypeptide are encoded by nucleic acids, conditions suitable for the production of siRNAs can include conditions under which the cell will express (i.e. transcribe and, in some cases, translate) the dsRNA and/or the siRNA-binding polypeptide from the nucleic acid. The precise conditions will vary depending on the exact identity of the bacterial cell, the presence of other exogenous DNA or mutations, and whether or not a nucleic acid encoding a dsRNA and/or siRNA-binding polypeptide is operably linked to an inducible or constitutive promoter. In some embodiments, wherein the nucleic acid(s) encoding a dsRNA and/or siRNA-binding polypeptide are operably linked to inducible promoters, conditions suitable for the production of siRNAs can include conditions which induce expression from the inducible promoter, e.g. permissive temperatures and/or the presence of compounds which induce expression from the inducible promoter. In some embodiments, conditions suitable for the production of siRNAs can include conditions which encourage exponential growth of the bacterial cells. By way of non-limiting example conditions suitable for the production of siRNAs in *E. coli* T7 Express Iq (NEB) can include LB broth, Lennox (BD) at 37° C. with shaking at 250 rpm and appropriate antibiotics.

In some embodiments, a method of producing one or more siRNA species can further comprise isolating the siRNA-binding polypeptide and eluting the siRNAs bound to the siRNA-binding polypeptide. In some embodiments, the siRNA-binding polypeptide can be isolated via a purification tag as described elsewhere herein.

In some embodiments, the siRNAs bound to a siRNA-binding polypeptide can be eluted from the isolated siRNA-binding polypeptide. Methods of eluting nucleic acids from proteins are well known in the art. By way of non-limiting example, siRNAs can be eluted from a siRNA-binding polypeptide by contacting the polypeptide-siRNA complex with a solution comprising 0.5% SDS for 10 min at room temperature with rotation. The solution can then be collected and passed through a 0.22 µm centrifuge filter (Corning).

In some embodiments, the siRNAs eluted from a siRNA-binding polypeptide can be further purified. Methods of nucleic acid purification are well known in the art and include, but are not limited to anion exchange HPLC, PAGE purification, desalting, and filtration. See, e.g. Gjerde et al. "RNA Purification and Analysis" Wiley-VCH; 2009 and Farrell et al. "RNA Methodologies" 4$^{th}$ Ed., Academic Press; 2010. In some embodiments, the siRNAs eluted from a siRNA-binding polypeptide can be further purified by HPLC.

In some embodiments, the siRNAs can be isolated from the totality of the cell contents without first isolating the siRNAs bound to siRNA-binding polypeptides. Methods of purifying RNA molecules are well known in the art, as described above, and any method or combination of methods known in the art can be used to isolate and/or purify the siRNAs produced according to the methods described herein.

In some embodiments, the methods described herein can further comprise contacting the bacterial cell with one or more modified nucleotides before or during the culturing step, thereby causing one or more modified nucleotides to be incorporated into the siRNA(s) of the presently described technologies. A modified nucleotide can be any nucleotide other than adenine "A", guanine "G", uracil "U", or cytosine "C". Such modified nucleotides include nucleotides which contains a modified sugar moiety, a modified phosphate moiety and/or a modified nucleobase. A modified nucleotide residue or a derivative or analog of a natural nucleotide are also useful. Examples of modified residues, derivatives or analogues include, but are not limited to, aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH2 UTP, 2'NH2 CTP, and 2'F UTP. Such modified nucleotides include, but are not limited to, aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH2 uridine, 2'NH2 cytidine, and 2' F uridine, including the free pho (NTP) RNA molecules as well as all other useful forms of the nucleotides. Further non-limiting examples of modified nucleotides can include ribonucleotides having a 2'-O-methyl (TOme), 2'-deoxy-2'fluoro, 2'-deoxy, 5-C-methyl, 2'-methoxyethyl, 4'-thio, 2'-amino, or 2'-C-allyl group, locked nucleic acid (LNA) nucleotides (e.g., 2'-O, 4'-C-methylene-(D-ribofuranosyl) nucleotides), 2'-methoxyethoxy (MOE) nucleotides, 2'-methylthio-ethyl nucleotides, 2'-deoxy-2'-fluoro nucleotides, 2'-deoxy-2'-chloro nucleotides, and 2'-azido nucleotides), nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole. Modification of the sugar moiety can include, but is not limited to, replacement of the ribose, ring with a hexose, cyclopentyl or cyclohexyl ring. Alternatively, the D-ribose ring of a naturally-occurring nucleic acid can be replaced with an L-ribose ring or the (3-anomer of a naturally occurring nucleic acid can be replaced with the a-anomer. Modified phosphate moieties can include phosphorothioates, phosphomdithioates, methyl phosphonates, alkylphosphonates, alkylphosphonothioates, methyl phosphates, phosphoramidates, and the like, or combinations thereof. Oligonucleotides which comprise such modified phosphate linkages can have improved properties when compared to corresponding oligonucleotides comprising only phosphate diester linkages, e.g. increased resistance to degradation by nucleases. Modified nucleobases include 7-deazaguanine, 7-deaza-8-azaguanine, 5-propynylcytosine, 5-propynyluricil, 7-deazaadenine, 7-deaza-8azaadenine, 7-deaza-6-oxopurine, 6-oxopurine, 3-deazaadenosine, 2-oxo-5-methylpyrimidine, 2-oxo-4-methylthio-5methylpyrimidine, 2-thiocarbonyl-4-oxo-5-methylpyrimidine, 4-oxo-5-methylpyrimidine, 2-aminopurine, 5-fluorouricil, 2,6-diaminopurine, 8-aminopurine, 4triazolo-5-methylthymine, and 4-triazolo-5-methyluracil. Modified nucleobases can also include abasic moieties. Additional non-limiting examples of modified nucleotides include biotinylated nucleotides, amine-modified nucleotides, alkylated nucleotides, fluorophore-labeled nucleotides, radiolabeled nucleotides, phosphorothioates, phosphoramidites, phosphites, ring atom modified derivatives and the like. In some embodiments, a modified nucleotide can be a G-clamp nucleotide. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., J Am. Chem. Soc., 120:8531-8532 (1998); which is incorporated herein by reference in its entirety. In some embodiments, a modified nucleotide can comprise multiple modifications. In some embodiments, a cell can be contacted with any combination of modified nucleotides.

In one aspect, the technology described herein relates to a library of siRNA species, the library comprising a plurality of clonal bacterial cell populations; wherein each clonal population comprises bacterial cells as described herein. In some embodiments, the bacterial cells can comprise at least a siRNA-binding polypeptide and a dsRNA; wherein the dsRNA comprises a nucleic acid sequence substantially complementary to a target RNA. In some embodiments, wherein a bacterial cell comprises dsRNAs specific for a single target RNA, the clonal bacterial population comprising that cell can comprise a population of siRNAs which will specifically bind to the single target RNA and/or which will specifically silence the expression of the target RNA.

In one aspect, the technology described herein relates to a library of siRNA species, the library comprising a plurality of populations of siRNAs; wherein each population of siRNAs is obtained according to the methods described herein. As used herein, a "population of siRNAs" refers to two or more siRNAs, wherein at least two of the siRNAs comprise non-identical sequences, but wherein the two or more siRNAs each comprise a nucleic acid sequence substantially complementary to the same target RNA. For example, a population of siRNAs can comprise two more siRNA species. In some embodiments, a population of siRNAs can be generated from a single dsRNA comprising a nucleic acid sequence substantially complementary to a target RNA. In some embodiments, a population of siRNAs can bind to a single target RNA and/or can specifically silence the expression of the target RNA. A population of siRNAs can be present within a bacterial cell or isolated from a bacterial cell.

Methods of creating bacterial libraries, and/or libraries of compounds isolated from bacterial cells are well known in the art. By way of non-limiting example, a bacterial cell library can be in the form of a plurality of multi-well plates, with each well of a plate comprising a clonal bacterial population. The clonal bacterial populations can be provided in media or in glycerol stocks. In some embodiments, a library can comprise multiple wells which comprise identical clonal populations, i.e. a clonal population can appear multiple times in a library. In some embodiments, a library can comprise a plurality of multi-well plates, with each well of a plate comprising one or more siRNA species (e.g. a siRNA species or a population of siRNA species) isolated from one or more clonal bacterial populations. Methods of isolating nucleic acids from bacterial cells are well known in the art and examples are described elsewhere herein. In some embodiments, libraries can be created using automated and/or high-throughput methods, e.g. robotic colony-picking.

In some embodiments, a library can comprise pooled samples, e.g. multiple clonal bacterial populations, multiple isolated siRNAs, or multiple isolated populations of siRNA species can be pooled so that a smaller number of samples must be initially screened. The individual components of a "positive" pooled can be subsequently screened separately.

In some embodiments, a library can comprise 10 or more pools of, populations of, and/or individual siRNA species (e.g. isolated or present within bacterial cells), e.g. 10 or more, 100 or more, 1,000 or more, 10,000 or more, or 100,000 or more pools of, populations of, and/or individual siRNA species.

In some embodiments, a library can comprise a plurality of populations of siRNAs, wherein each population of siRNAs can silence at least one target RNA of a target set. A target set of RNAs can comprise, e.g. the transcriptome of a cell, the transcriptome of an organism, the transcriptome of a cell and/or organism in a specific state (e.g. a diseased organism or an organism at a specific stage of development) or a subtractive transcriptome (e.g. all the transcripts present in a cell under one condition but which are not present in the cell in a second condition).

In one aspect, the technology described herein relates to vectors which enable the use of the methods and compositions described herein. In some embodiments, the vector can be an expression vector. In some embodiments, the vector can be a plasmid. In some embodiments, a vector for use in the methods and compositions described herein can comprise (a) a nucleic acid encoding a siRNA-binding polypeptide and (b) a dsRNA cloning site. In some embodiments, a dsRNA cloning site further can further comprise a nucleic acid encoding a dsRNA, wherein the dsRNA comprises a nucleic acid sequence substantially complementary to a target RNA. As used herein, a "dsRNA cloning site" refers to a multiple cloning site comprising at least one restriction enzyme site and which can accept the insertion of nucleic acid sequence(s) comprising the sequence of both a sense and anti-sense strand of nucleic acid; wherein one strand is substantially complementary to the nucleic acid sequence of a target RNA, such that a dsRNA will be encoded and can be expressed, e.g. a sequence inserted at the dsRNA cloning site will be operably linked to a promoter as described herein. In some embodiments, a single nucleic acid molecule can comprise the sequence of both the sense and anti-sense strand prior to insertion at the dsRNA cloning site. In some embodiments, a dsRNA cloning site can comprise a nucleic acid sequence which comprises sequences which can be cleaved by at least two different restriction enzymes.

In some embodiments, a dsRNA cloning site can comprise a nucleic acid sequence which comprises sequences which can be cleaved by at least four different restriction enzymes. In some embodiments, a dsRNA cloning site can comprise two multiple cloning sites separated by a nucleic acid sequence encoding a hairpin sequence; wherein each multiple cloning site comprises a nucleic acid sequence which comprises sequences which can be cleaved by at least two different restriction enzymes. Methods of cloning various dsRNA sequences into expression vectors, as well as expression vectors which can be adapted for use as described herein, are well known in the art, see, e.g. Schwab et al. 2006 Plant Cell 18:1121-1133; Fraser. AfCS Reports 2004; Atayde et al. Mol Biochem Parasitol 2012 184:55-8: Kruhn et al. Cell Cycle 2009 8:3349-3354; and Timmons et al. Gene 2001 263:103-112; which are incorporated by reference herein in their entireties.

In some embodiments, a vector for use in the methods and/or compositions described herein can comprise at least one constitutive promoter operably linked to at least one of the siRNA-binding polypeptide or the dsRNA multiple cloning site. In some embodiments, a vector for use in the methods and/or compositions described herein can comprise at least one inducible promoter operably linked to at least one of the siRNA-binding polypeptide or the dsRNA multiple cloning site.

Aspects of the technology described herein further relate to kits comprising the compositions described herein and kits for practicing the methods described herein.

In some embodiments, the technology described herein relates to a kit comprising a bacterial cell as described herein, e.g. a bacterial cell comprising at least a siRNA-binding polypeptide and a dsRNA; wherein the dsRNA comprises a nucleic acid sequence substantially complementary to a target RNA as described herein.

In some embodiments, the technology described herein relates to a vector for use in the methods and compositions of the present technology, as described herein. In some embodiments, a kit for the production of one or more species of siRNA can comprise a vector comprising (a) a nucleic acid encoding a siRNA-binding polypeptide and (b) a dsRNA cloning site. In some embodiments, a kit for the production of one or more species of siRNA can comprise two vectors; wherein the first vector comprises a nucleic acid encoding a siRNA-binding polypeptide; and wherein the second vector comprises a dsRNA cloning site. In some embodiments, the dsRNA cloning site can further comprise a dsRNA; wherein the dsRNA comprises a nucleic acid sequence substantially complementary to a target RNA. In some embodiments, the kit can further comprise a bacterial cell.

In some embodiments, a kit for the production of one or more species of siRNA can comprise a bacterial cell comprising a siRNA-binding polypeptide and a vector comprising a dsRNA cloning site. In some embodiments, the bacterial cell can comprise a nucleic acid encoding a siRNA-binding polypeptide. In some embodiments, the nucleic acid encoding a siRNA-binding polypeptide can be a part of an expression vector, a plasmid, a naked nucleic acid, and/or the bacterial genome.

In some embodiments of a kit as described herein, the siRNA-binding polypeptide can comprise a purification tag. In some embodiments of a kit as described herein, the siRNA-binding polypeptide can be encoded by a nucleic acid. In some embodiments of a kit as described herein, the DNA encoding at least one of the siRNA-binding polypeptide or the dsRNA can be a portion of a vector. In some embodiments of a kit as described herein at least one of the siRNA-binding polypeptide or the dsRNA can be constitutively expressed. In some embodiments of a kit as described herein, at least one of the siRNA-binding polypeptide or the dsRNA can be inducibly expressed.

In some embodiments of a kit as described herein, the bacterial cell can express a siRNA-generating polypeptide. In some embodiments of a kit as described herein, the cell can be an *Escherichia coli* cell.

In some embodiments, the technology described herein relates to a kit comprising a library of siRNA species as described herein.

In some embodiments, the compositions and methods described herein can be used to test the efficacy of one or more siRNA species, and/or for the screening of a siRNA library.

In some embodiments, the efficacy of one or more siRNA species can be assessed in cultured mammalian cells. Methods of targeting mammalian cells with inhibitory RNAs via bacterial invasion are known in the art, see, e.g. Zhao et al. Nature Methods 2005 2:967-973; which is incorporated by reference herein in its entirety. In some embodiments, a bacterial cell for use in such an assay can comprise a polypeptide or nucleic acid encoding a polypeptide which can bind to a mammalian cell surface receptor, (e.g. the invasin (inv) gene of *Yersinia psuedotuberculosis* which binds the integrin receptor of mammalian cells. In some embodiments, a bacterial cell for use in such an assay or screen can comprise a mutation reducing the ability of the cell to synthesize or maintain the cell wall, (e.g. deletion of the asd gene of *E. coli*, thereby rendering the cell a diaminopimelic acid (DAP) auxotroph). Reducing the ability of the cell to synthesize or maintain the cell wall can make the cell susceptible to lysis or degradation after it enters a mammalian cell, thereby releasing inhibitory RNAs (e.g. in the methods described herein, siRNAs) into the mammalian cell.

In some embodiments, the efficacy of one or more siRNA species can be assessed in vivo in *C. elegans*. dsRNAs readily cross cell membranes in *C. elegans*, and a number of protocols are known for conducting RNAi in *C. elegans*, including bacterial feeding assays (see, e.g. Timmons, L., and A. Fire. Nature 1998 395:854 and Lehner et al. Protocol Exchange 2006 159; which are incorporated by reference herein in their entireties.

In some embodiments, the efficacy of one or more siRNA species can be assessed by first isolating the one or more species of siRNA from the bacterial cells and then contacting a cell and/or organism with the one or more species of siRNA. Methods of introducing ribonucleic acids, and in particular, ribonucleic acids which cause RNAi into various cells and organisms are well known in the art (see, e.g. Sioud, M. "siRNA and miRNA Gene Silencing" Humana Press: 2011; "Gene Silencing by RNA Interference" Sohail, M. ed. CRC Press: 2004: each of which are incorporated by reference herein in their entireties). Examples of cells and/or organisms suitable for use in such methods include cultured cells (e.g. mammalian cells or human cells), primary cells, diseased cells (e.g. cancerous cells), *C. elegans*, and *Danio rerio*.

The efficacy of one or more siRNA species can be assessed by screens, selections, and/or by assays. High throughput methods of screening siRNA libraries are known in the art, e.g. phenotype screens, automated cell and worm processing, etc. The appropriate method of determining the efficacy of one or more siRNA species can be dependent upon the nature of the target RNA, e.g. siRNA species specific for target RNAs which control reproduction in *C.*

*elegans* can be screened by examining the rate and success of reproduction of worms in the presence of the siRNAs.

In some embodiments, libraries of siRNA species as described herein, comprising siRNA species targeting a number of different target RNAs can be used in phenotypic screens to identify target RNAs associated with a particular phenotype (e.g. siRNAs which perturb a particular developmental process or which slow the progression of a disease). Phenotypic screens can comprise the assays described above for determining efficacy, e.g. mammalian cell invasion assays. In some embodiments, phenotypic screens can involve high-throughput assays.

In one aspect, described herein is a therapeutic agent comprising a siRNA species or population of siRNA species isolated from a bacterial cell as described herein and/or produced according to the methods described herein. According to the methods described herein, a dsRNA comprising a nucleic acid substantially complementary to a target RNA can be provided to a bacterial cell herein, and a siRNA species and/or population of siRNA species which can be used to reduce the expression of the corresponding target RNA can be produced. In some embodiments, target RNAs can be disease-associated RNAs, i.e. RNAs whose overexpression is associated with the cause, progression, or maintenance of a disease state, e.g. oncogenes. In some embodiments, target RNAs can be RNAs originating from a pathogenic organism, e.g. the target RNAs can comprise sequences of viral, bacterial, fungal, and/or parasitic origin. In some embodiments, target RNAs can be viral RNAs and/or RNAs produced from viral genomic material. In some embodiments, a siRNA species and/or population of siRNA species which can be used to reduce the expression of the target RNA can be produced according to the methods described herein and administered to a subject in need of a reduction of the level of expression of the target RNA. In some embodiments, a single siRNA species can be administered. In some embodiments, a population of siRNA species can be administered. As demonstrated in the Examples herein, a population of siRNA species can have increased efficacy and a lower likelihood of off-target effects as compared to a single siRNA species. In some embodiments, multiple populations of siRNA species can be administered, i.e. multiple target RNAs can be silenced. In some embodiments, the technology described herein relates to a pharmaceutical composition comprising a bacterial cell, siRNA species, and/or population of siRNA species according to the methods and compositions described herein. In some embodiments, the technology described herein relates to the use of a bacterial cell, siRNA species, or population of siRNA species according to the methods and compositions described herein in the manufacture of a medicament. Methods of preparing medicaments comprising RNA molecules, e.g. siRNAs, are known in the art, (see e.g. Oh and Park. Advanced Drug Delivery Reviews. 2009 61:850-62; which is incorporated by reference herein in its entirety).

It is contemplated that the siRNA technology described herein, as well as the methods and compositions relating thereto, can be applied to gene silencing applications in any cell and/or organism comprising siRNA machinery. Non-limiting examples include gene silencing applications humans, non-human animals, livestock species, insects (e.g. honeybees), plants, crop plants, etc. In some embodiments, the gene silencing can be for therapeutic purposes. In some embodiments, the gene silencing can be for agricultural purposes, e.g. to treat agricultural diseases in animals and/or crops or to increase yields in animals and/or crops.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A bacterial cell comprising a siRNA-binding polypeptide and a dsRNA comprising a nucleic acid sequence substantially complementary to a target RNA.
2. The bacterial cell of paragraph 1, wherein the siRNA-binding polypeptide comprises a purification tag.
3. The bacterial cell of any of paragraphs 1-2, wherein the siRNA-binding polypeptide is encoded by a nucleic acid.
4. The bacterial cell of any of paragraphs 1-3, wherein the siRNA-binding polypeptide is selected from the group consisting of:
    p19 polypeptide; tombusvirus p19 polypeptide; B2 polypeptide; HC-Pro polypeptide;

p38 polypeptide; p122 polypeptide; p130 polypeptide; p21 polypeptide; p1b polypeptide; and NS3 polypeptide.
5. The bacterial cell of any of paragraphs 1-4, wherein the dsRNA is greater than 21 nucleotides in length.
6. The bacterial cell of any of paragraphs 1-5, wherein the dsRNA is a hairpin RNA.
7. The bacterial cell of any of paragraphs 1-6, wherein the bacterial cell expresses an RNase III polypeptide.
8. The bacterial cell of any of paragraphs 1-7, wherein the bacterial cell expresses an RNase III polypeptide encoded by an exogenous nucleic acid sequence.
9. The bacterial cell of any of paragraphs 1-8, wherein the bacterial cell is an *Escherichia coli* cell.
10. The bacterial cell of any of paragraphs 1-9, wherein at least one of the siRNA-binding polypeptide and the dsRNA are constitutively expressed.
11. The bacterial cell of any of paragraphs 1-10, wherein at least one of the siRNA-binding polypeptide and the dsRNA are inducibly expressed.
12. The bacterial cell of any of paragraphs 1-11, wherein the DNA encoding at least one of the siRNA-binding polypeptide or the dsRNA is part of a plasmid.
13. The bacterial cell of any of paragraphs 1-12, wherein the dsRNA comprises nucleic acid sequences substantially complementary to a multiplicity of target RNAs.
14. A method of producing one or more siRNA species which can inhibit the expression of a target RNA, the method comprising:
   culturing a bacterial cell of any of paragraphs 1-13 under conditions suitable for the production of siRNAs.
15. The method of paragraph 14, further comprising a second step of isolating the siRNA-binding polypeptide and eluting the siRNAs bound to the siRNA-binding polypeptide.
16. The method of any of paragraphs 14-15, further comprising purifying the siRNAs eluted from the siRNA-binding polypeptide by HPLC.
17. The method of any of paragraphs 14-16, further comprising contacting the cell with one or more modified nucleotides before or during the culturing step.
18. A pharmaceutical composition comprising a siRNA produced according to the method of any of paragraphs 14-17.
19. The composition of paragraph 18, further comprising a population of siRNA species.
20. A pharmaceutical composition comprising a siRNA isolated from a bacterial cell of any of paragraphs 1-13.
21. The composition of paragraph 20, further comprising a population of siRNA species.
22. The use of a siRNA produced according to the method of any of paragraphs 14-17 in the production of a medicament.
23. The use of a siRNA isolated from a bacterial cell of any of paragraphs 1-13 in the production of a medicament.
24. A vector comprising;
   a nucleic acid encoding a siRNA-binding polypeptide; and
   a dsRNA cloning site.
25. The vector of paragraph 24, wherein the dsRNA cloning site comprises at least one restriction enzyme site and can accept the insertion of at least one nucleic acid sequence such that a dsRNA is encoded and can be expressed.
26. A vector comprising:
   a nucleic acid encoding a siRNA-binding polypeptide; and
   a dsRNA comprising a nucleic acid sequence substantially complementary to a target RNA.
27. The vector of any of paragraphs 24-26, wherein the siRNA-binding polypeptide is selected from the group consisting of:
   p19 polypeptide; tombusvirus p19 polypeptide; B2 polypeptide; HC-Pro polypeptide;
   p38 polypeptide; p122 polypeptide; p130 polypeptide; p21 polypeptide; p1b polypeptide; and NS3 polypeptide.
28. The vector of any of paragraphs 24-27, wherein the vector is a plasmid.
29. The vector of paragraph 28, wherein the plasmid further comprises a bacterial origin of replication.
30. A library of siRNA species, the library comprising:
   a plurality of clonal bacterial cell populations;
   wherein each clonal population is comprises bacterial cells of any of paragraphs 1-13.
31. A library of siRNA species, the library comprising:
   a plurality of populations of siRNAs;
   wherein each population of siRNAs is obtained according to the methods of any of paragraphs 14-17.
32. The library of paragraph 31, wherein each population of siRNAs binds to a single target RNA.
33. A kit comprising a bacterial cell of any of paragraphs 1-13.
34. A kit for the production of one or more species of siRNA, the kit comprising;
   a bacterial cell comprising an siRNA-binding polypeptide; and
   at least one vector comprising a dsRNA cloning site.
35. A kit for the production of one or more species of siRNA, the kit comprising:
   a bacterial cell comprising an siRNA-binding polypeptide; and
   at least one vector comprising a dsRNA comprising a nucleic acid sequence substantially complementary to a target RNA.
36. A kit comprising the vector of any of paragraphs 24-29.
37. A kit for the production of one or more species of siRNA, the kit comprising two vectors;
   wherein the first vector comprises a nucleic acid encoding a siRNA-binding polypeptide; and
   wherein the second vector comprises a dsRNA cloning site.
38. A kit for the production of one or more species of siRNA, the kit comprising two plasmids;
   wherein the first vector comprises a nucleic acid encoding a siRNA-binding polypeptide; and
   wherein the second vector comprises a dsRNA comprising a nucleic acid sequence substantially complementary to a target RNA.
39. The kit of any of paragraphs 33-38, wherein at least one vector is a plasmid.
40. The kit of paragraph 39, wherein the plasmid further comprises a bacterial origin of replication.
41. The kit of any of paragraphs 33-40, wherein the kit further comprises a bacterial cell.
42. A kit for the production of one or more species of siRNA, the kit comprising;

a bacterial cell comprising a nucleic acid encoding a siRNA-binding polypeptide; and a vector comprising a dsRNA cloning site.

43. A kit for the production of one or more species of siRNA, the kit comprising;

a bacterial cell comprising a nucleic acid encoding a siRNA-binding polypeptide; and a vector comprising a dsRNA comprising a nucleic acid sequence substantially complementary to a target RNA.

44. The kit of any of paragraphs 33-43, wherein the siRNA-binding polypeptide comprises a purification tag.

45. The kit of any of paragraphs 33-44, wherein the siRNA-binding polypeptide is encoded by a nucleic acid.

46. The kit of any of paragraphs 41-45, wherein the bacterial cell expresses an RNase III polypeptide.

47. The kit of any of paragraphs 41-46, wherein the cell is an *Escherichia coli* cell.

48. The kit of any of paragraphs 33-47, wherein at least one of the siRNA-binding polypeptide and the dsRNA are operably linked to a constitutive promoter.

49. The kit of any of paragraphs 33-48, wherein at least one of the siRNA-binding polypeptide and the dsRNA are operably linked to an inducible promoter.

50. The kit of any of paragraphs 33-49, wherein the DNA encoding at least one of the siRNA-binding polypeptide or the dsRNA is part of a plasmid.

51. A kit comprising the library of any of paragraphs 30-32.

EXAMPLES

RNA interference (RNAi) by double-stranded (ds) small interfering RNAs (siRNA) suppresses gene expression by inducing the degradation of mRNAs bearing complementary sequences[1,2]. Endogenous siRNAs (perfectly paired dsRNAs ~21-25 nt in length) play an important role in host defense against RNA viruses and in transcriptional gene silencing in plants and may have similar functions in other eukaryotes[3]. Transfection of synthetic siRNAs into eukaryotic cells[4,5] to silence genes has become an indispensable tool to investigate gene function, and siRNA-based therapy is being developed to knockdown genes implicated in disease[6]. Although bacteria expressing sense and antisense sequences can be fed to worms to knock down individual genes[7], no one has used living organisms to produce highly active, purified siRNAs. Described herein is a method to produce highly potent siRNAs from *E. coli* ectopically expressing p19, a siRNA binding protein, which stabilizes siRNA-like species generated by bacterial RNase III.

Figure 1B:
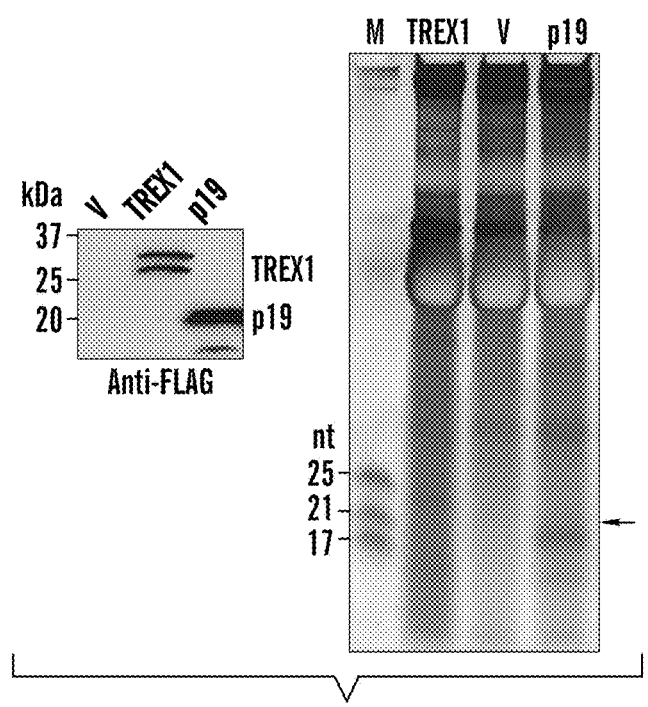
Figure 5A:
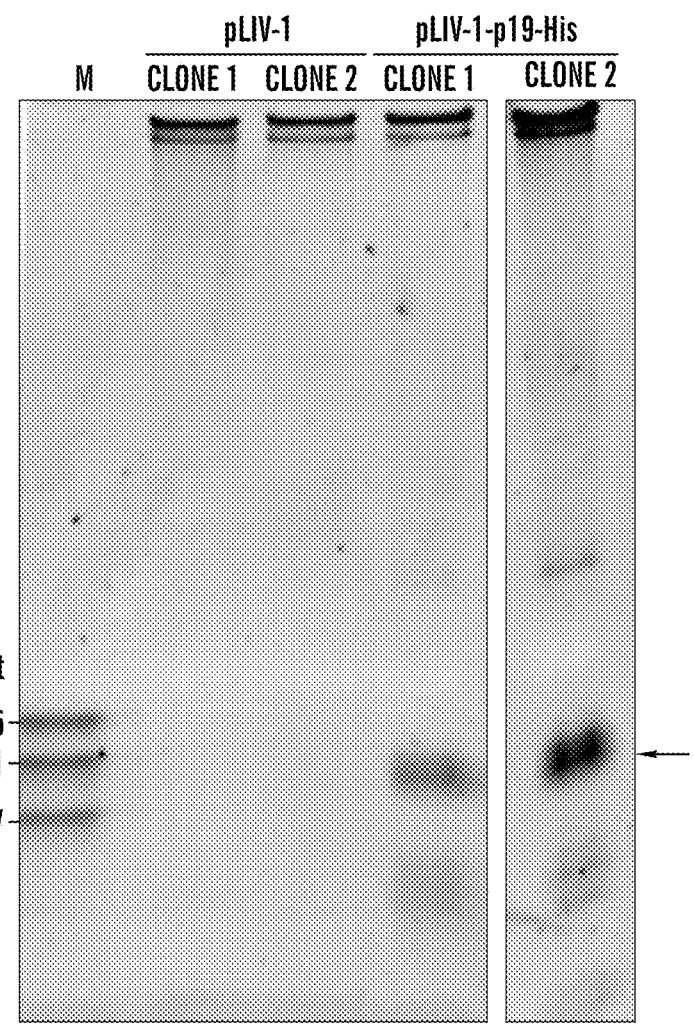
FIGS. 5A-5B demonstrate that ectopic expression of p19 stabilizes ~21 nt small RNA species in *Listeria monocytogenes*.
Figure 5B:
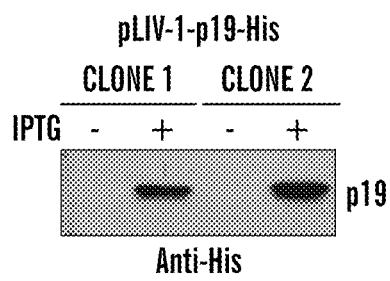
Figure 6A:
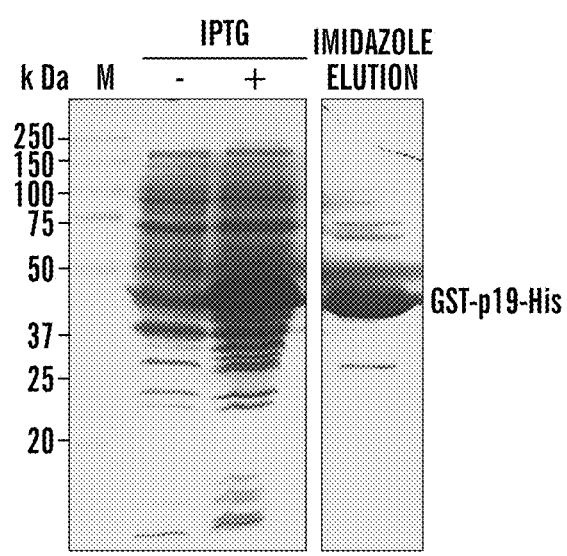
FIGS. 6A-6D demonstrate that SDS efficiently elutes GST-p19-His-bound small RNAs but not GST-p19-His protein.
Figure 6B:
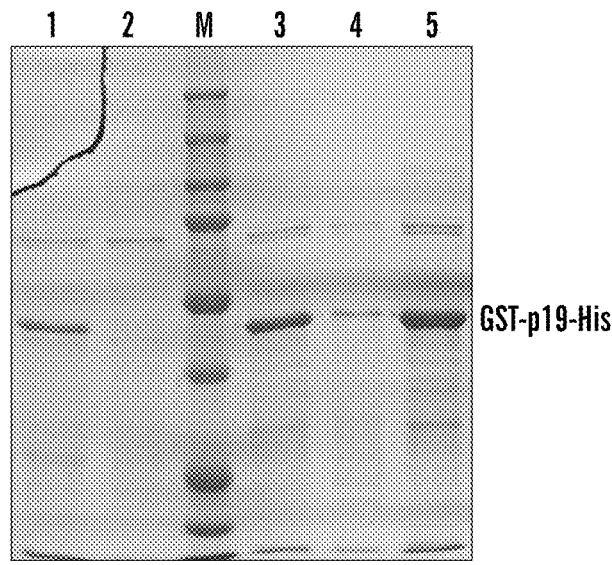
Figure 6C:
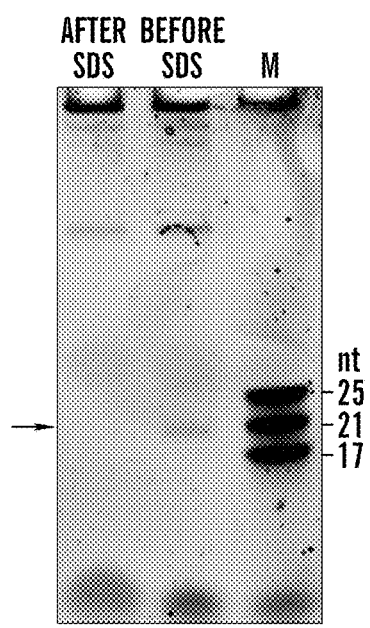
Figure 6D:
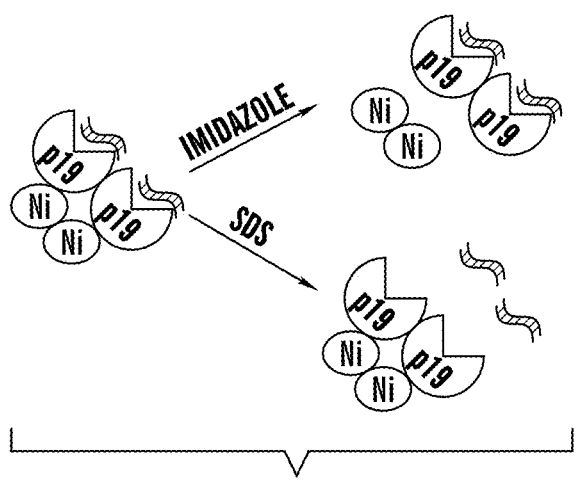

The most common method to make siRNA is chemical synthesis[4,5]. Effective siRNA sequences are predicted using computer algorithms. siRNAs can also be made from transcribed longer dsRNAs by in vitro biochemical processing by RNase III family enzymes[8,9]. In the latter case, the resulting siRNAs contain many sequences against one target, which sometimes can be more effective than any one sequence[10], and pools of siRNAs often have fewer off-target effects on genes bearing partially complementary sequences[11]. While gene knockdown by transfection of siRNAs is usually transient, short hairpin RNA construct, delivered by plasmid or lentivirus, is commonly used to achieve stable gene silencing.

p19, an RNAi suppressor protein encoded by the plant RNA virus tombusvirus[12], selectively binds to ~21 nt siRNAs, including those targeting the virus[13]. The p19 dimer binds to the 19 nt duplex region of an siRNA in a sequence-independent manner[14,15]. It was originally planned to enrich for endogenous siRNAs in mammalian cells using p19 coupled to magnetic beads[15]. As a negative control, p19 beads were incubated with total RNA isolated from *E. coli*, an organism that supposedly lacks the RNAi machinery, that was transformed or not with a pcDNA3.1+ plasmid in which p19 was cloned after the CMV immediate-early promoter. Surprisingly p19 beads pulled down ~21 nt dsRNAs from RNA of both human T-cells (ACH2 cell line) and the transformed *E. coli* cells (FIG. 1A). Although the CMV promoter is mostly used for efficient expression of genes in mammalian cells, *E. coli* harboring pcDNA3.1+ plasmids encoding FLAG-tagged TREX1 or p19 gene expressed their respective proteins (FIG. 1B). When total RNA isolated from *E. coli* transformed with empty vector or vectors encoding p19 or TREX1 was separated on SYBR Gold-stained denaturing polyacrylamide gels, a distinctive ~21 nt band was evident only in p19-expressing *E. coli* (FIG. 1B). These data indicate that p19 protein expression may have stabilized a cryptic siRNA-like RNA species in *E. coli*. In *Listeria monocytogenes*, a Gram-positive bacterium, expression of p19 also allowed the detection of ~21 nt small RNAs (FIGS. 5A-5B).

Figure 1C:
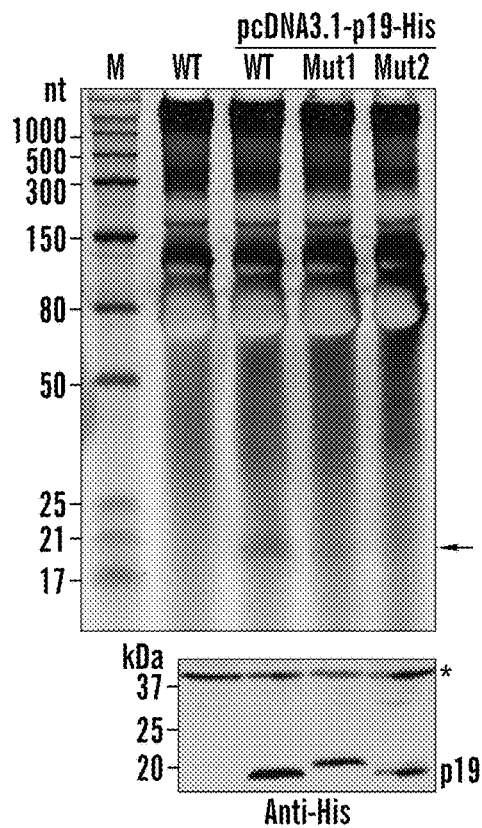
Figure 1E:
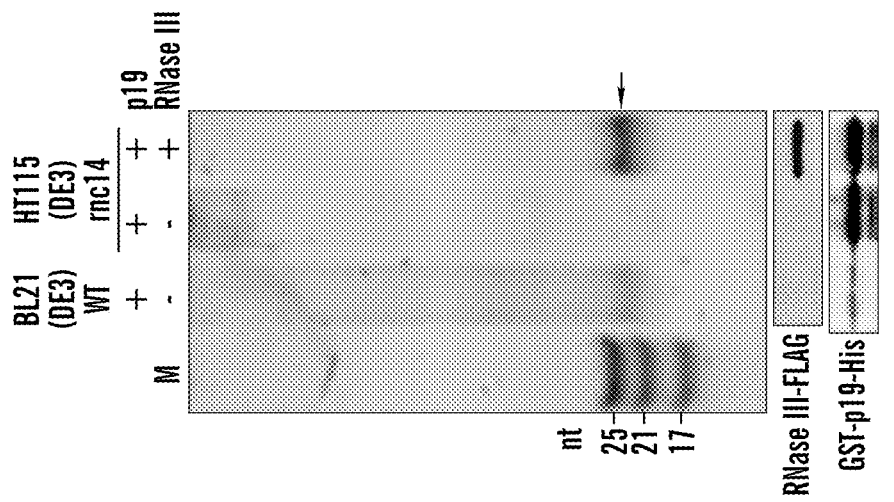
Figure 1D:
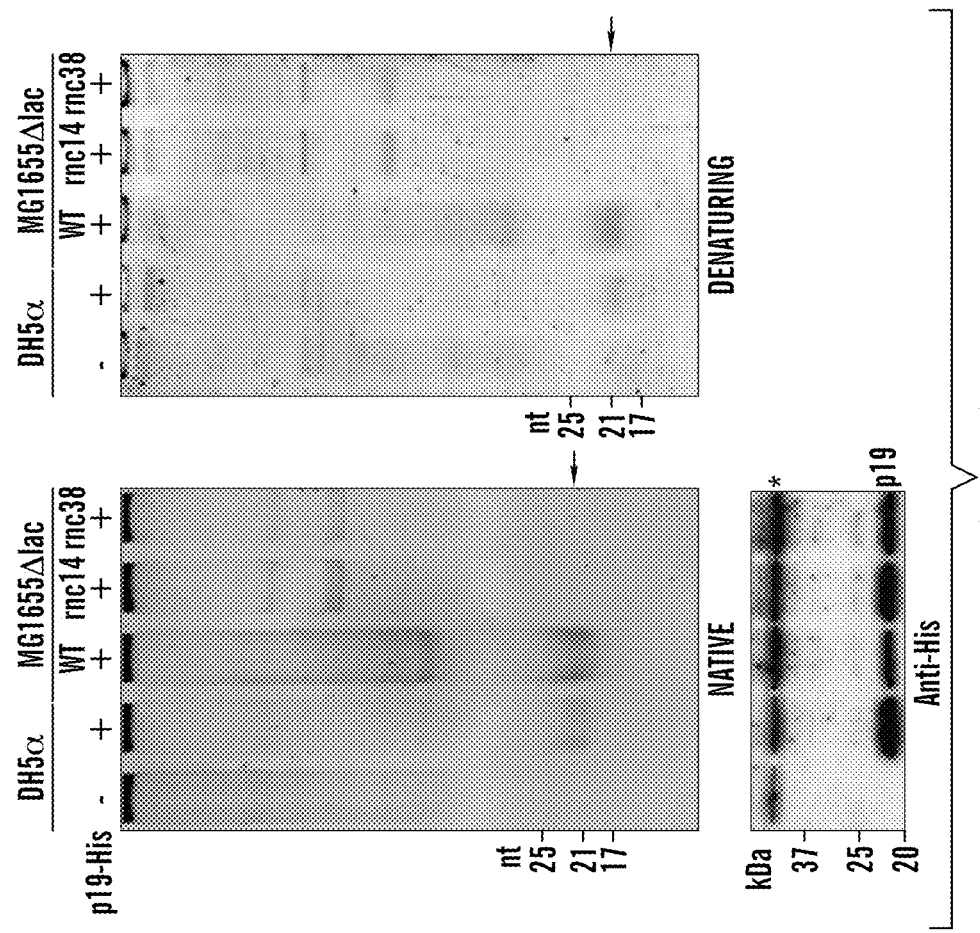

To determine if the small RNAs detected in *E. coli* depended on functional p19, RNA was isolated from *E. coli* expressing WT p19, or p19 mutants that disrupted siRNA binding[14,16] (FIG. 1C). The ~21 nt dsRNA band was more prominent in bacteria expressing WT p19. Thus siRNA-binding to p19 promotes the accumulation of siRNA-like RNAs in *E. coli*. Next the nuclease responsible for making small RNAs was sought. The most likely candidate was RNase III, an ancestor of eukaryotic Dicer, responsible for the final step of siRNA biogenesis[17]. *E. coli* RNase III is known to generate siRNA-sized dsRNAs from longer dsRNAs in vitro[9]. p19-expressing plasmids were used to transform two RNase III mutant strains, rnc14[18] and rnc38[19] (FIG. 1D). In both mutant strains, p19 beads failed to pull down any visible small RNAs. Furthermore restoration of RNase III expression in HT115(DE3), a rnc14 strain, also restored the p19-dependent small RNAs (FIG. 1E), providing support for the hypothesis that RNase III is responsible for generating these small RNAs in *E. coli*. Thus, accumulation of these bacterial small RNAs depends on ectopic p19 and bacterial RNase III.

Figure 2B:
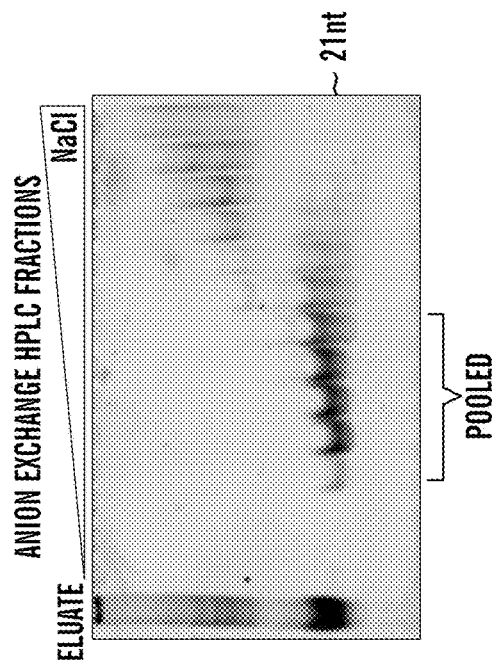
FIGS. 2A-2F demonstrate pro-siRNAs knockdown EGFP expression.
Figure 2A:
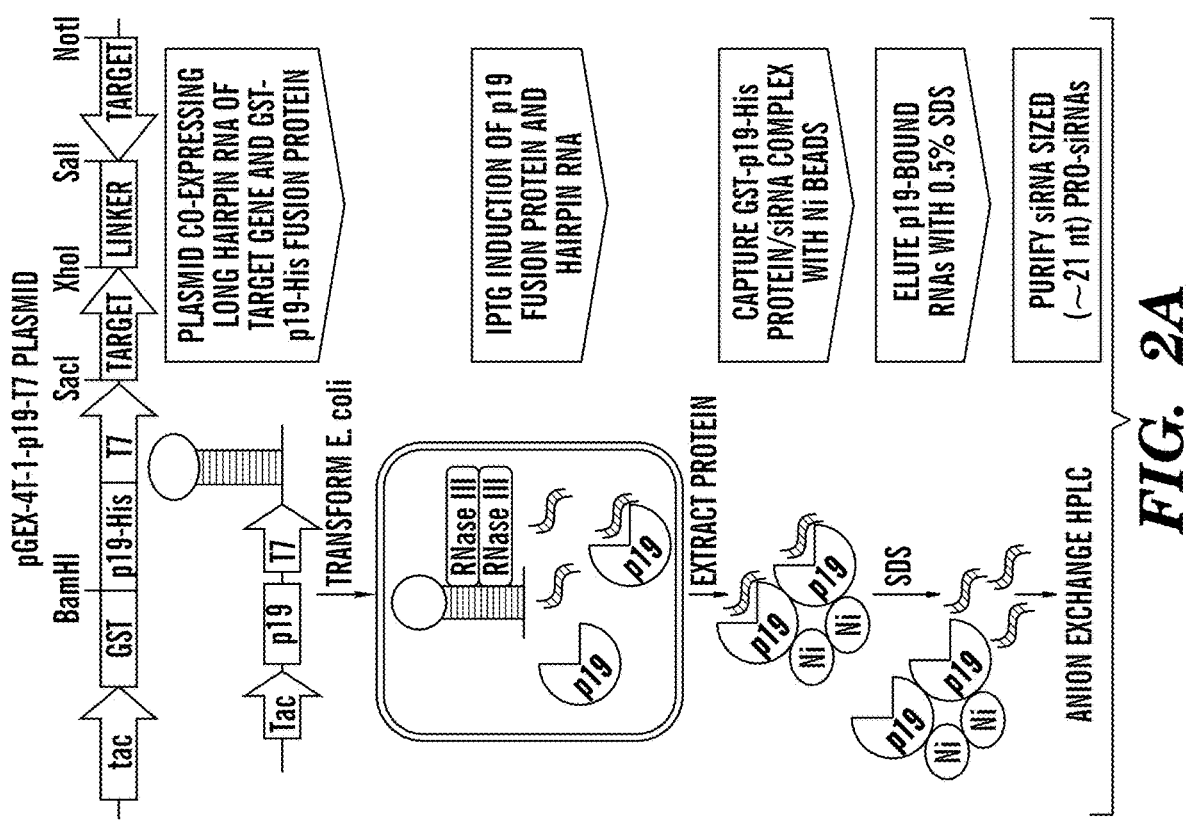
Figure 2C:
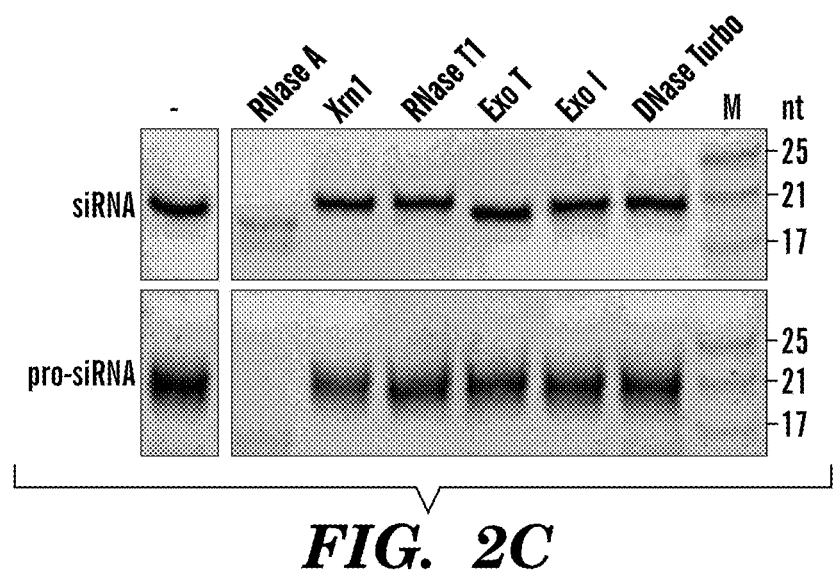

It was next asked whether small RNAs generated in p19-expressing *E. coli* behave like siRNAs and can be used for gene knockdown in mammalian cells. p19 was cloned into the pGEX-4T-1 plasmid to express a GST-p19 fusion protein with a C-terminal His tag (FIG. 2A). A T7 promoter driving expression of a hairpin RNA that contains a target sequence was inserted immediately after. To develop the method, a hairpin was designed that encoded full-length EGFP (EGFPFL). The expression of the GST-p19-His fusion protein and hairpin RNA were both induced by IPTG. The GST-p19-His protein was captured by Nickel (Ni) affinity chromatography and 0.5% SDS was used to selectively elute p19-bound RNAs that were predominantly ~21 nt long (FIGS. 2B and 6A-6D). Small RNAs were further purified from other longer RNAs by anion exchange HPLC. To verify that these bacterial small RNAs are double-stranded, they were treated with a variety of nucleases. Like chemically synthesized siRNAs, bacterial small RNAs were sensitive to RNase A, but were insensitive to enzymes that digest ssRNA or DNA (Xrn1, RNase T1, exonuclease T (Exo T), exonuclease I (Exo I), or DNase Turbo (FIG. 2C).

Figure 2D:
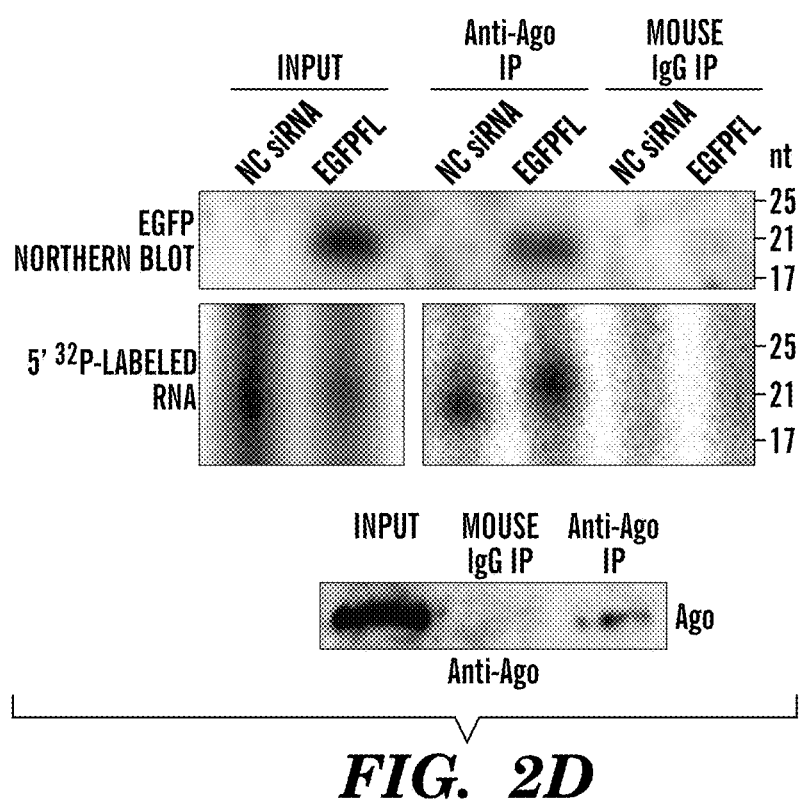

Next bacterial small RNAs, purified from *E. coli* expressing p19 and the EGFPFL hairpin and transfected into HeLa cells stably expressing d1EGFP (HeLa-d1EGFP), were loaded into the RNA-induced silencing complex (RISC) by immunoprecipitation with a pan-Argonaute (Ago) antibody (FIG. 2D). RNAs that precipitated with anti-Ago were ~21 nt long and hybridized to an EGFP probe, but no small RNA precipitated with control mouse IgG. Thus bacterial small RNAs were similar to synthetic siRNA in chemical composition and were incorporated into the RISC. These small RNAs were named 'pro-siRNAs' for prokaryotic siRNAs.

Figure 2E:
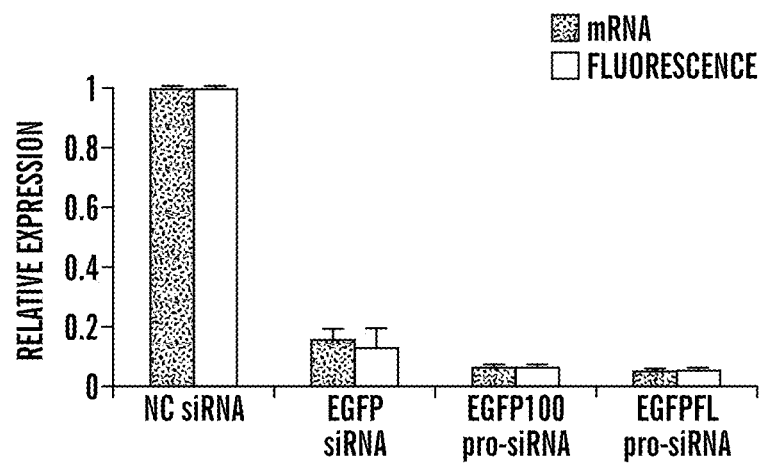
Figure 7A:
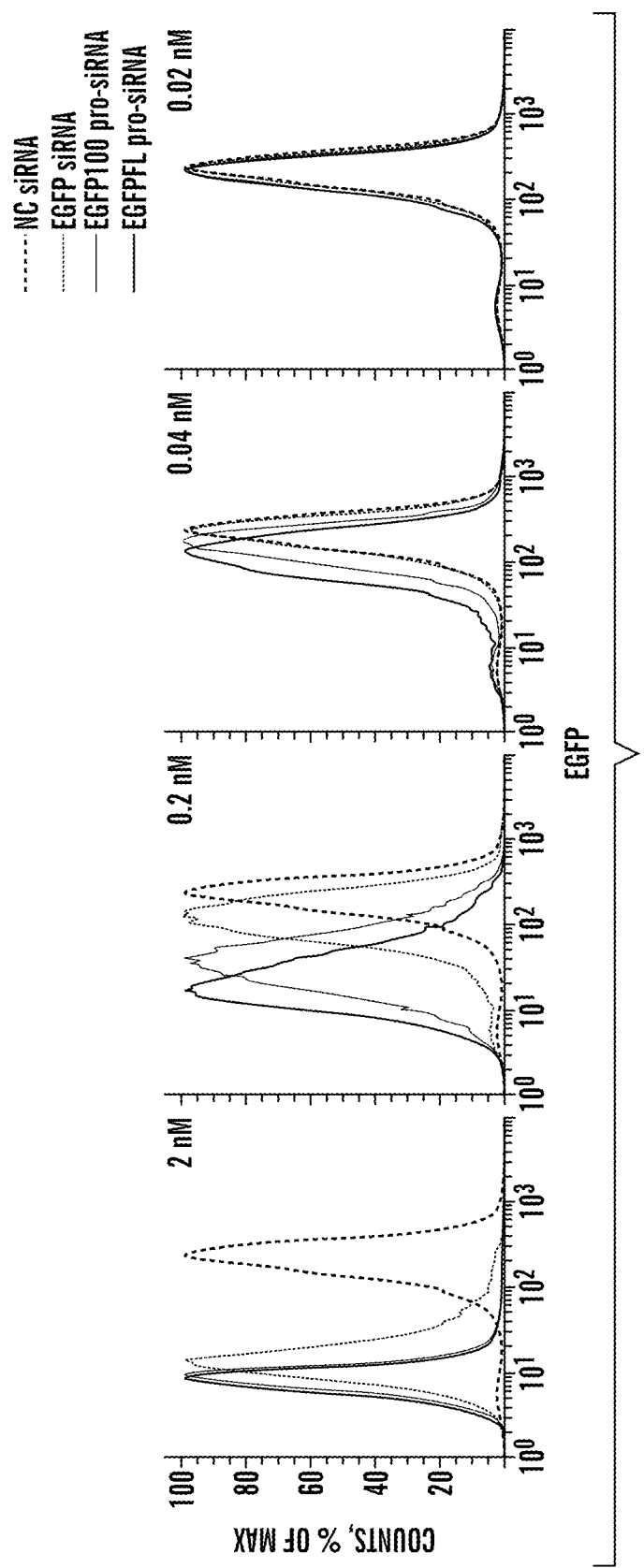
FIGS. 7A-7B demonstrate the dose response comparison of gene silencing by EGFP siRNAs and pro-siRNAs and test of antisense EGFP construct.
Figure 7B:
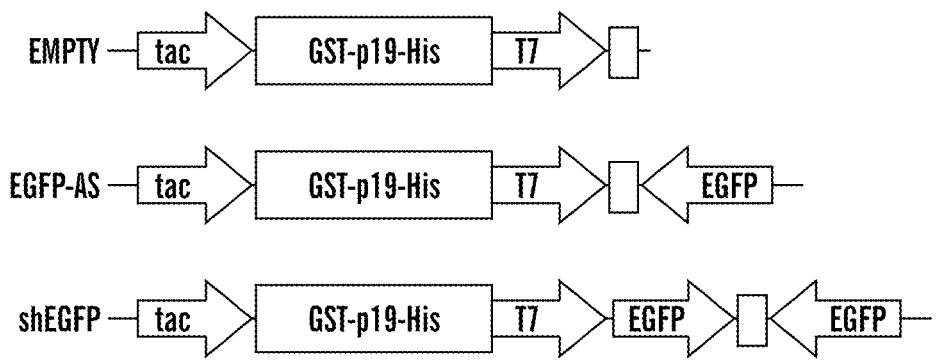
Figure 7B:
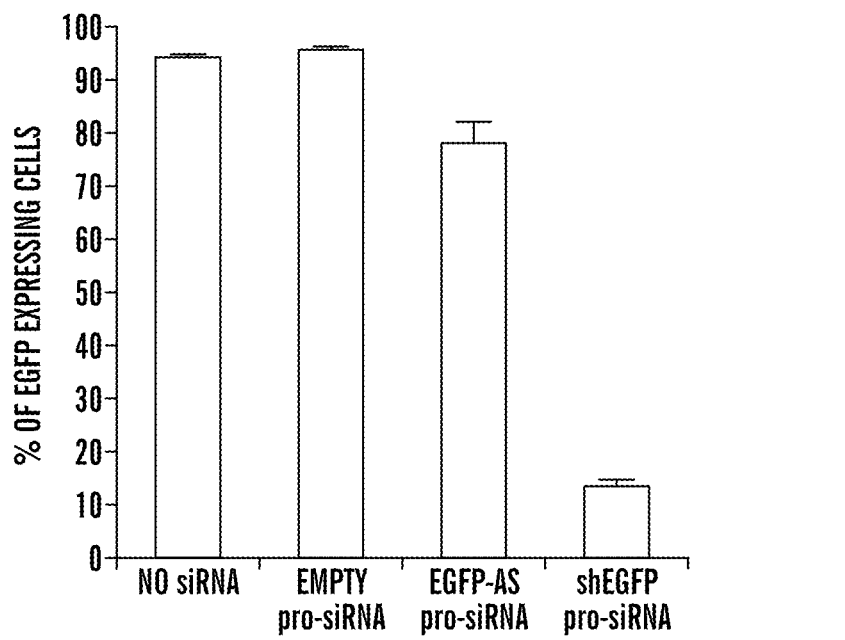
Figure 8A:
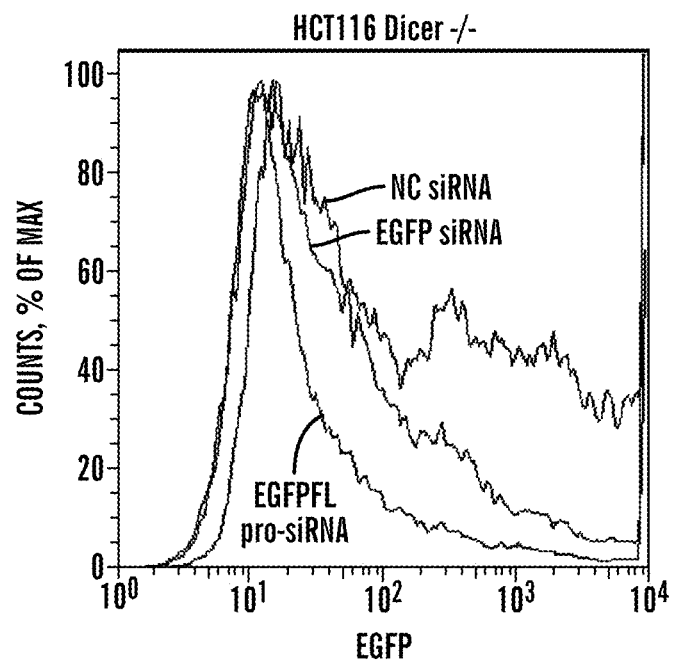
FIGS. 8A-8B demonstrate that pro-siRNA knockdown of gene expression is independent of Dicer.
Figure 8B:
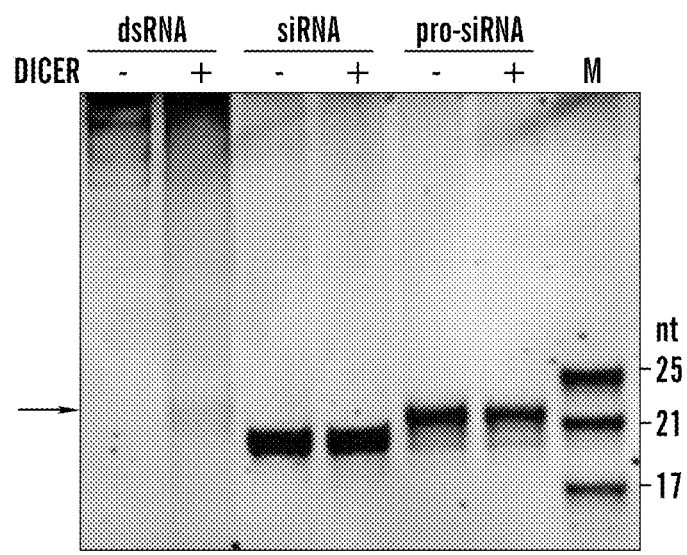

Since pro-siRNAs had properties of siRNAs, whether p19-captured EGFP pro-siRNAs induce gene knockdown was tested. qRT-PCR and flow cytometry were used to compare mRNA and protein knockdown, respectively, of d1EGFP in HeLa-d1EGFP cells transfected with a synthetic EGFP siRNA or pro-siRNAs purified from *E. coli* expressing p19 and hairpins of either full length EGFP (EGFPFL) or a 100 nt fragment that overlapped with the EGFP siRNA sequence (EGFP100). Both EGFPFL and EGFP100 pro-siRNAs knocked down EGFP expression more effectively than equimolar concentrations of siRNA (FIGS. 2E and 7A). pro-siRNAs made from the plasmid without or with only half of the EGFP hairpin could not silence EGFP effectively (FIG. 7B). As expected, silencing by pro-siRNA was Dicer-independent because EGFPFL pro-siRNA still functioned in Dicer-deficient HCT116 cells[20] and recombinant Dicer protein did not further process pro-siRNAs in vitro (FIGS. 8A-8B).

Figure 2F:
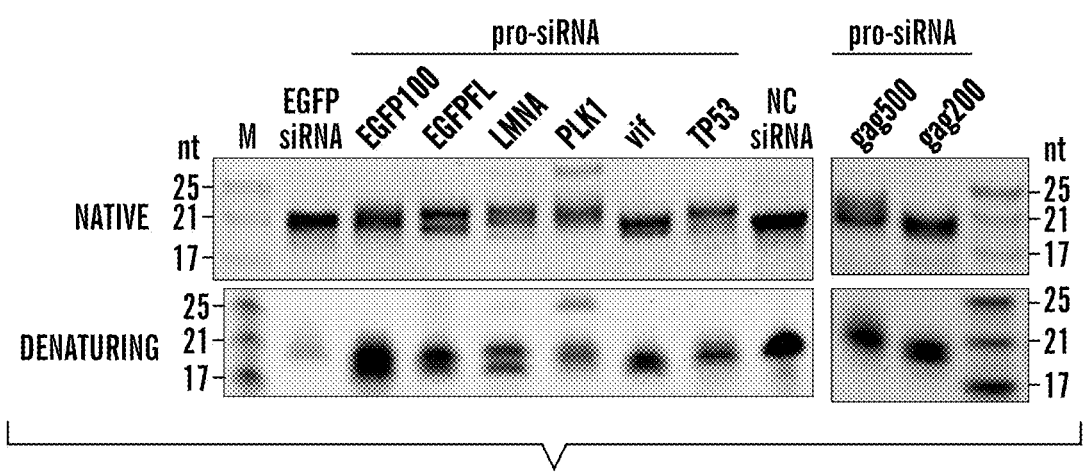
Figure 3A:
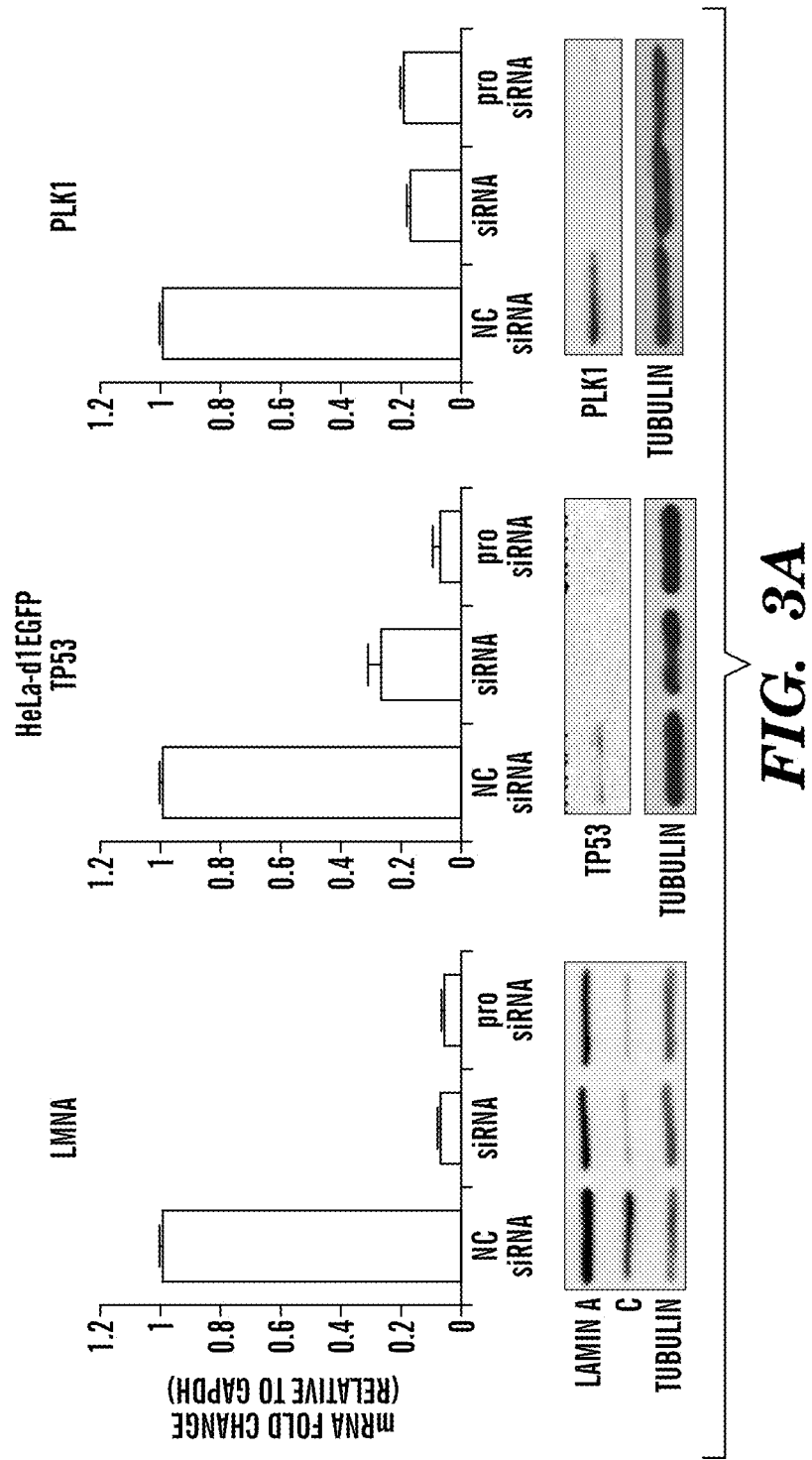
FIGS. 3A-3D demonstrate that pro-siRNA-mediated knockdown of endogenous and viral gene expression in human cells.
Figure 3A:
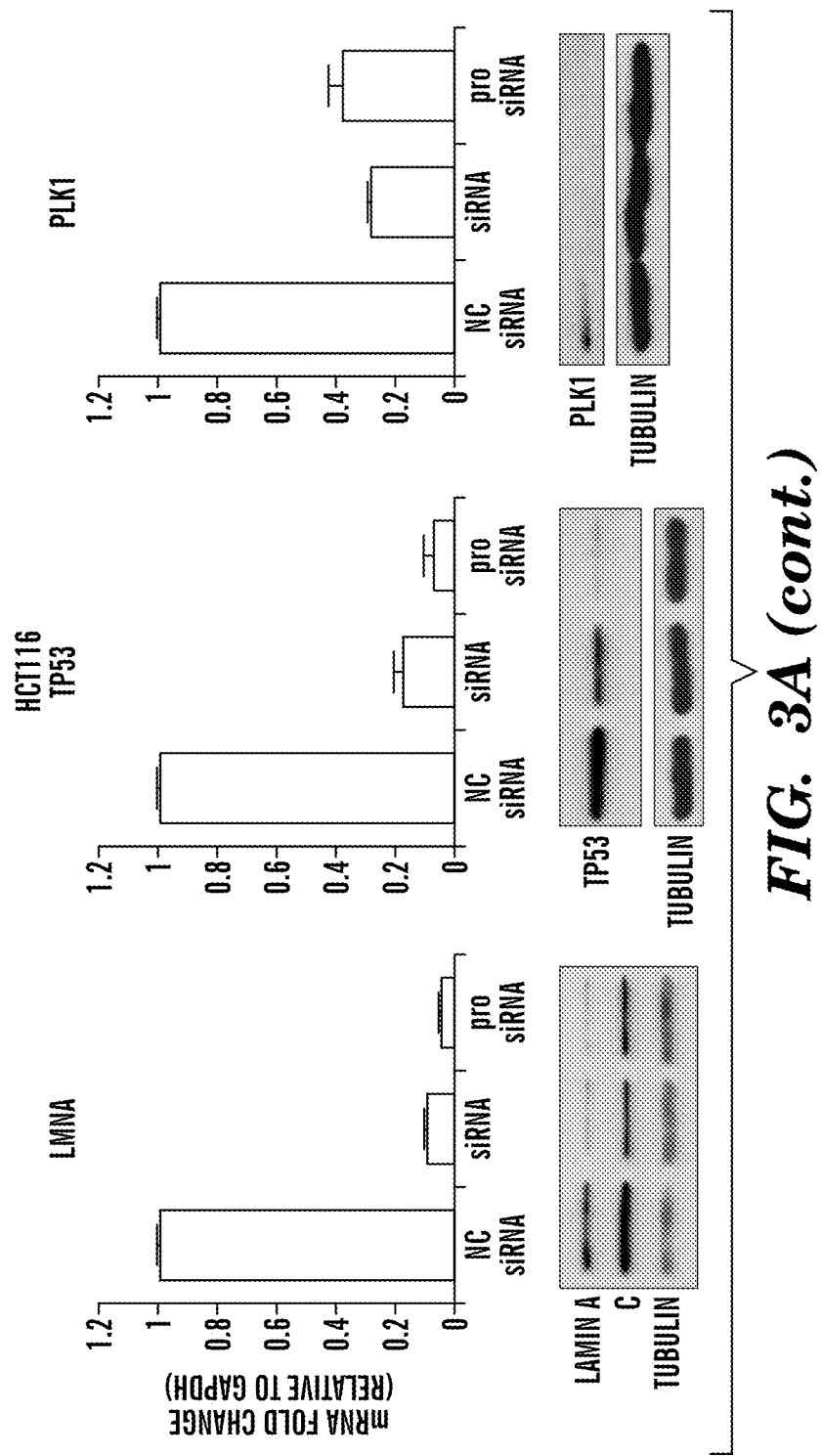
Figure 3B:
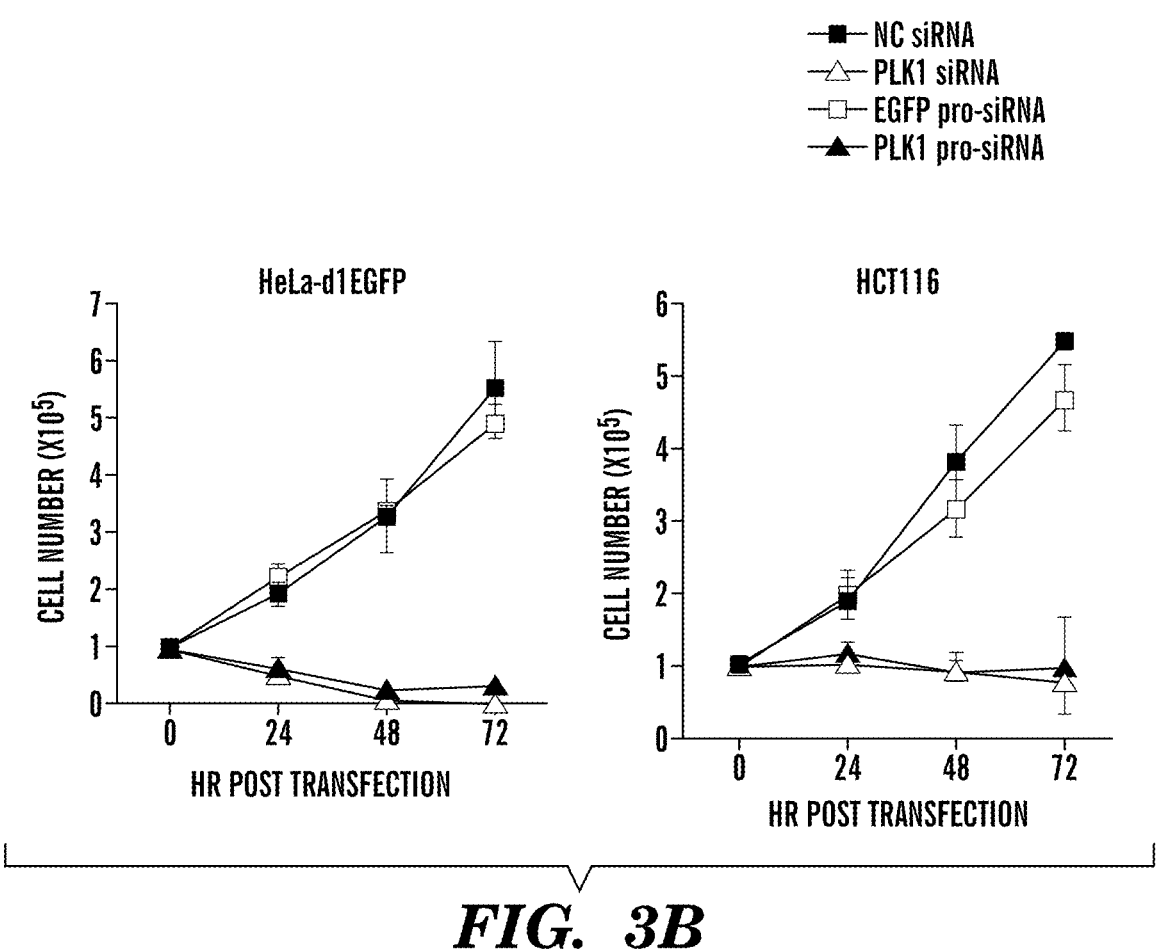
Figure 3C:
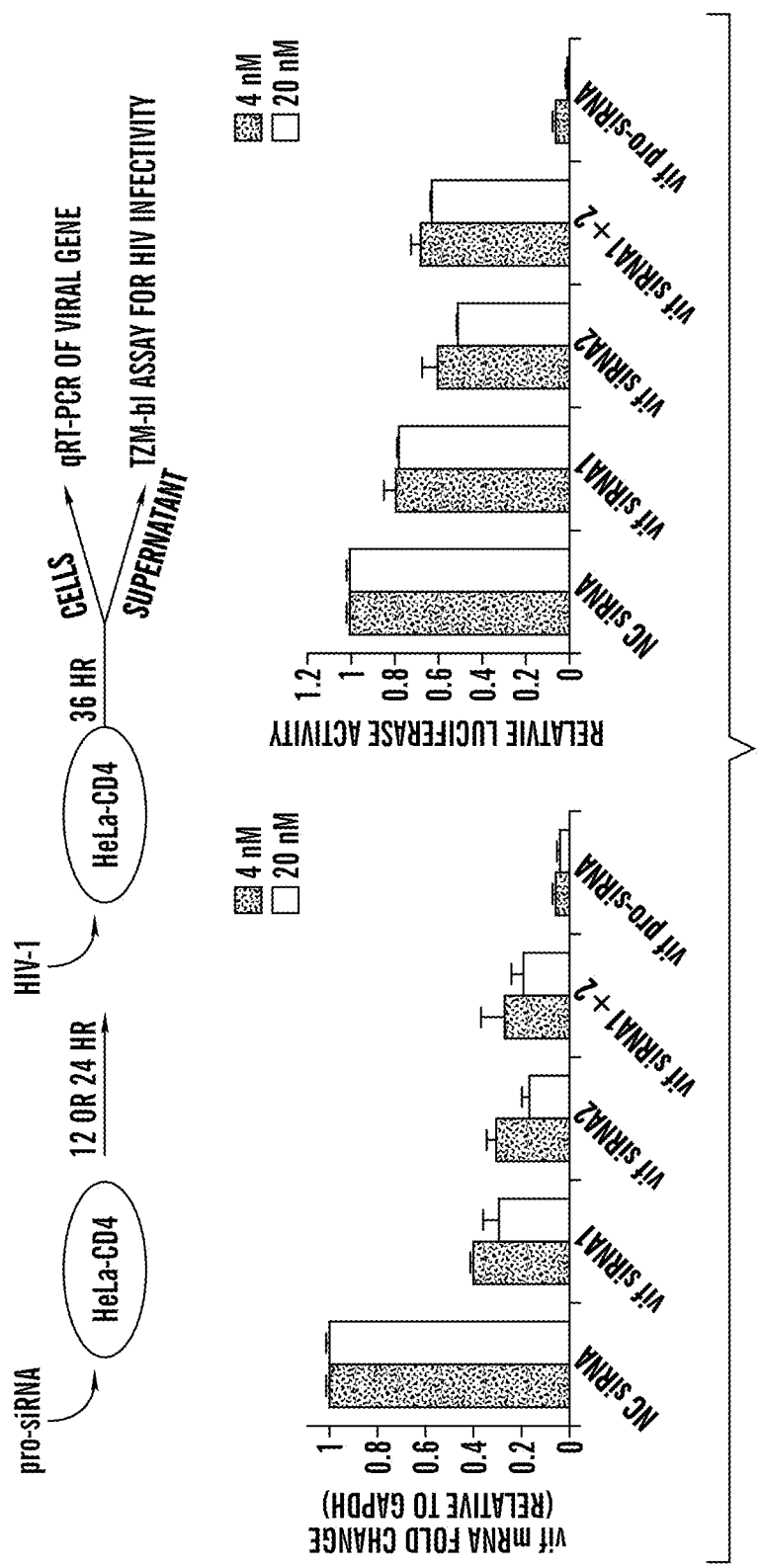
Figure 9:
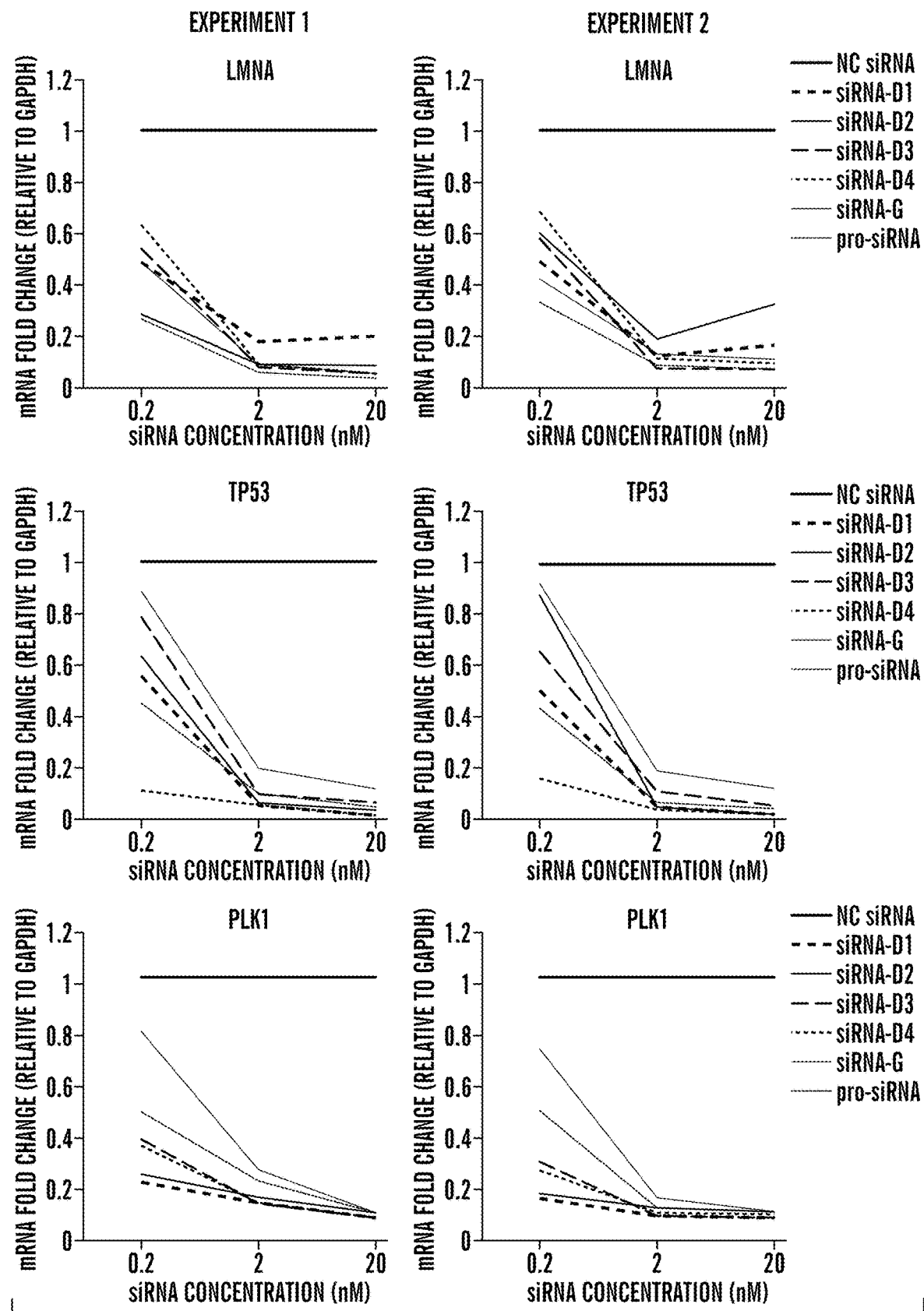
FIG. 9 depicts graphs demonstrating dose response comparison of gene silencing by pro-siRNAs and commercial siRNAs. Total RNAs were extracted from HeLa-d1EGFP cells 24 hrs after transfection. mRNA levels were normalized to negative control siRNA transfected cells. Two independent experiments were shown. Damachon siRNAs: siRNA-D1-D4. siRNA of published sequence: siRNA-G.

To test the effectiveness of pro-siRNA knockdown of endogenous and viral genes, we used convenient restriction sites to clone and express hairpins from the coding regions of LMNA (which encodes two splice variant products, lamin A and lamin C), PLK1, TP53 and HIV vif (viral infectivity factor) and gag (capsid antigen) to purify pro-siRNAs. The resulting hairpins contained 200-579 nt of each sense and antisense sequence (523 nt for LMNA, 299 nt for PLK1, 300 nt for TP53, 579 nt for vif200 and 500 nt for gag). The HPLC-purified pro-siRNAs for each gene contained a few different sized species that migrated close to the 21 nt marker on both native and denaturing polyacrylamide gels (FIG. 2F). For LMNA and PLK1 pro-siRNAs, a minor RNA band migrated at ~25 nt. Next the extent of knockdown of endogenous genes (LMNA, TP53, PLK1) by pro-siRNAs and commercially available siRNAs (LMNA and TP53 siRNAs were from a single sequence; PLK1 siRNAs were a pool of 4 siRNAs and were chemically modified by proprietary methods for enhanced stability and reduced off-target effects[21]) in HeLa-d1EGFP and HCT116 cells were compared. The extent of gene knockdown was similar between siRNA and pro-siRNA transfected at 4 nM (FIG. 3A). Since knocking down PLK1 causes death of dividing cells[22], viable cells were counted for 3 d following transfection with PLK1 or control siRNAs and pro-siRNAs (FIG. 3B). To more closely evaluate the potency of pro-siRNAs, dose response experiments comparing transfection of pro-siRNAs (0.2, 2, 20 nM) targeting LMNA, TP53 and PLK1 with five commercial siRNAs for each gene (four siRNAs from Dharmacon, of which the PLK1 siRNAs were chemically modified for enhanced RISC uptake or stability by proprietary methods, and one siRNA sequence chosen based on published effectiveness) were performed (FIG. 9). The potency of the commercial siRNAs varied, as best evaluated at the lowest concentration. The pro-siRNAs, whose sequences were not optimized, achieved similar gene knockdown as the commercially optimized siRNAs. At a concentration of 2 nM, each pro-siRNA achieved knockdown of ~90%. Because siRNA design algorithms are imperfect, identifying a potent siRNA usually requires test of several sequences which could be costly and time consuming. pro-siRNAs might circumvent the need to test multiple sequences to identify a single potent siRNA.

To examine potential toxicity of pro-siRNAs, growth was compared over 3 d in HeLa-d1GFP and HCT116 cells after transfection with either a negative control siRNA or EGFP pro-siRNA (FIG. 3B). Their growth curves were not significantly different. To compare the effectiveness of gene knockdown by pro-siRNAs and siRNAs, cell proliferation was examined after knocking down PLK1, which kills dividing cells[23]. PLK1 siRNAs and pro-siRNAs both dramatically reduced viability with indistinguishable kinetics.

Figure 3D:
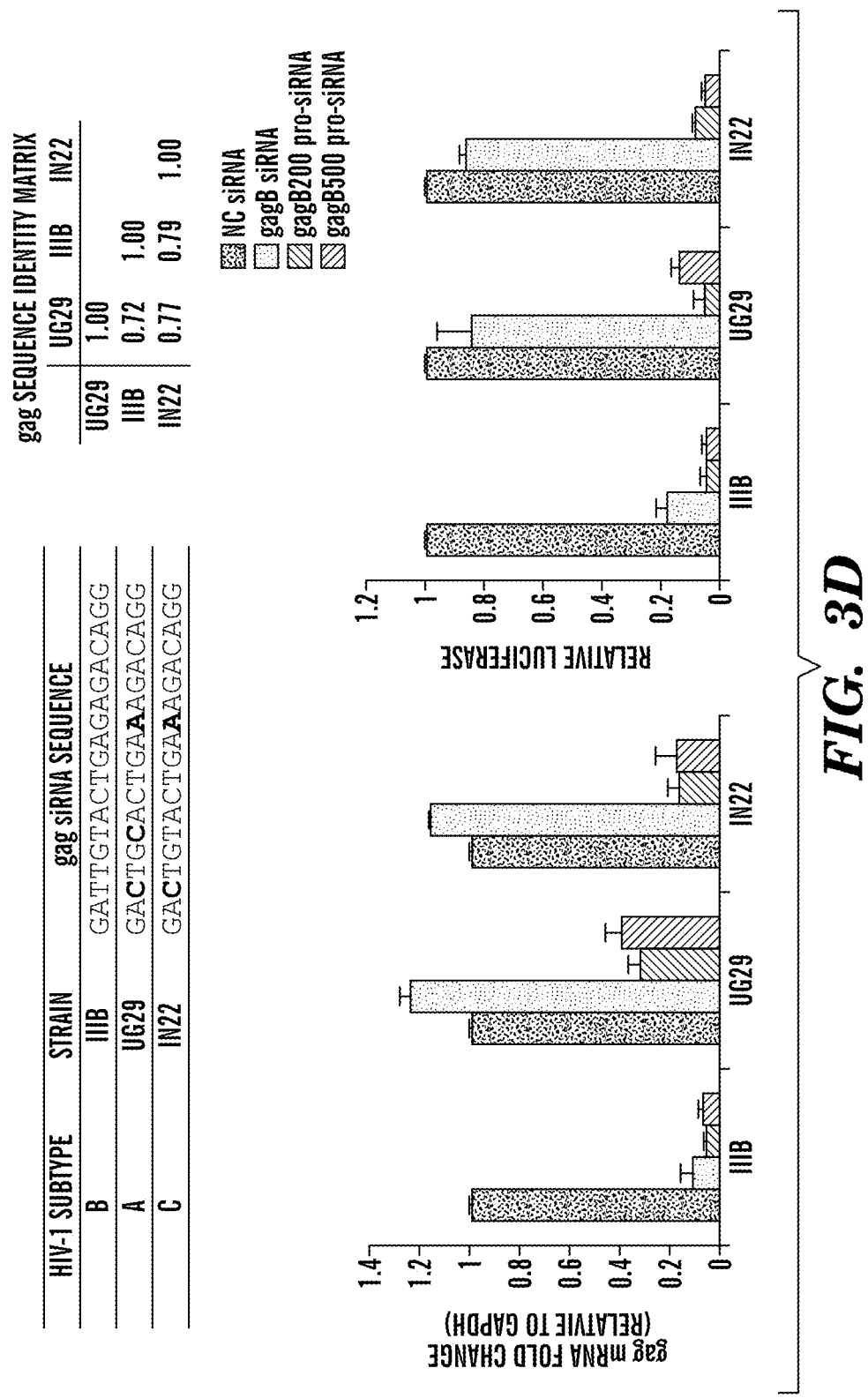

As another test of pro-siRNA function, the effect of knocking down the HIV accessory gene vif on in vitro propagation of HIV infection[23] was examined. vif, which targets the host restriction factor APOBEC3G for ubiquitylation and degradation, is not needed for the initial round of HIV replication, but is required to spread the infection to new cells by preventing APOBEC3G packaging into budding virions. The efficacy of the pro-siRNAs was compared with two validated siRNAs[23,24]. As expected, siRNAs and pro-siRNAs targeting vif did not alter the percentage of initially infected HeLa-CD4 cells (data not shown), but did suppress vif gene expression and inhibit subsequent rounds of infection, assessed in the TZM-bl luciferase reporter cell line (FIG. 3D). Transfection of vif pro-siRNAs resulted in much lower levels of vif mRNA in HeLa-CD4 cells and HIV tat-driven luciferase activity, compared to transfection with either or both vif siRNAs. Thus vif pro-siRNAs were superior to previously used siRNAs in inhibiting HIV spread in vitro.

One major obstacle to using RNAi to suppress HIV or other viruses is sequence diversity. Because pro-siRNAs target many sequences within a gene, pro-siRNAs directed against a viral gene can have broader activity against diverse viral strains than siRNAs and can also be less likely to generate siRNA-resistant mutants. Previous attempts to identify an siRNA against HIV-1 clade B gag that could inhibit viral isolates from other clades were unsuccessful[24]. A sequence that protected against infection with all clade B viruses was tested, but no single sequences which were well enough conserved were found that also protected against other clades. To investigate whether pro-siRNAs might have broader activity than the best clade B sequence, gag pro-siRNAs were engineered using hairpins with 200 and 500 nt long stems from the gag coding region of clade B HIV-III$_B$ virus. The gagB200 and gagB500 pro-siRNAs more potently suppressed HIV-III$_B$, than the previous gag siRNA (FIG. 2D). More importantly, unlike the gag siRNA, both gag pro-siRNAs knocked down gag mRNA and inhibited viral spread in vitro for UG29 (clade A) and IN22 (clade C) viruses, although they worked slightly less effectively than against III$_B$ virus. These data indicate that pro-siRNAs could be particularly beneficial for targeting heterogeneous and rapidly evolving viral genes.

Figure 10A:
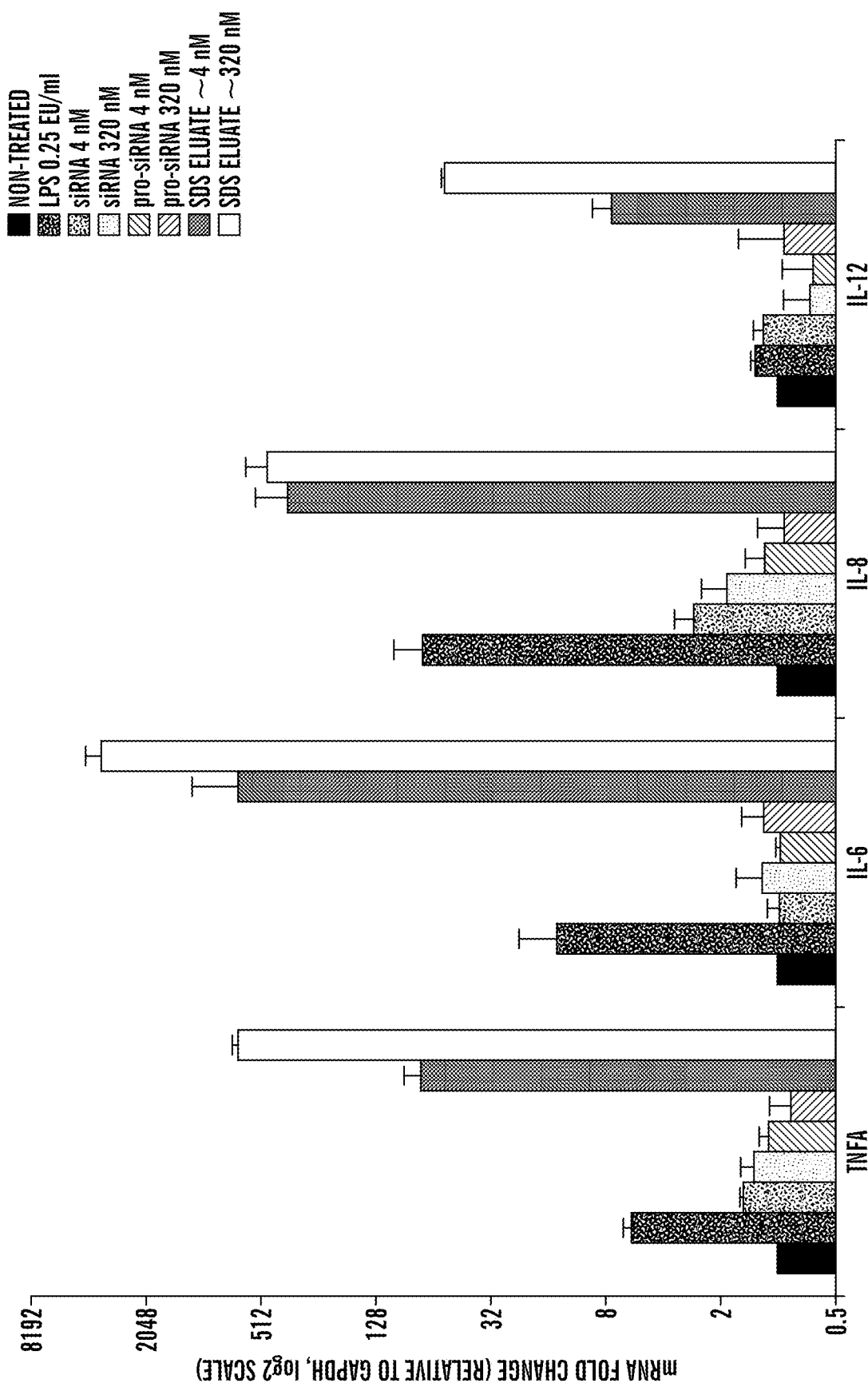
FIGS. 10A-10B demonstrate that pro-siRNAs induce little expression of proinflammatory cytokines in primary monocyte-derived human macrophages.
Figure 10B:
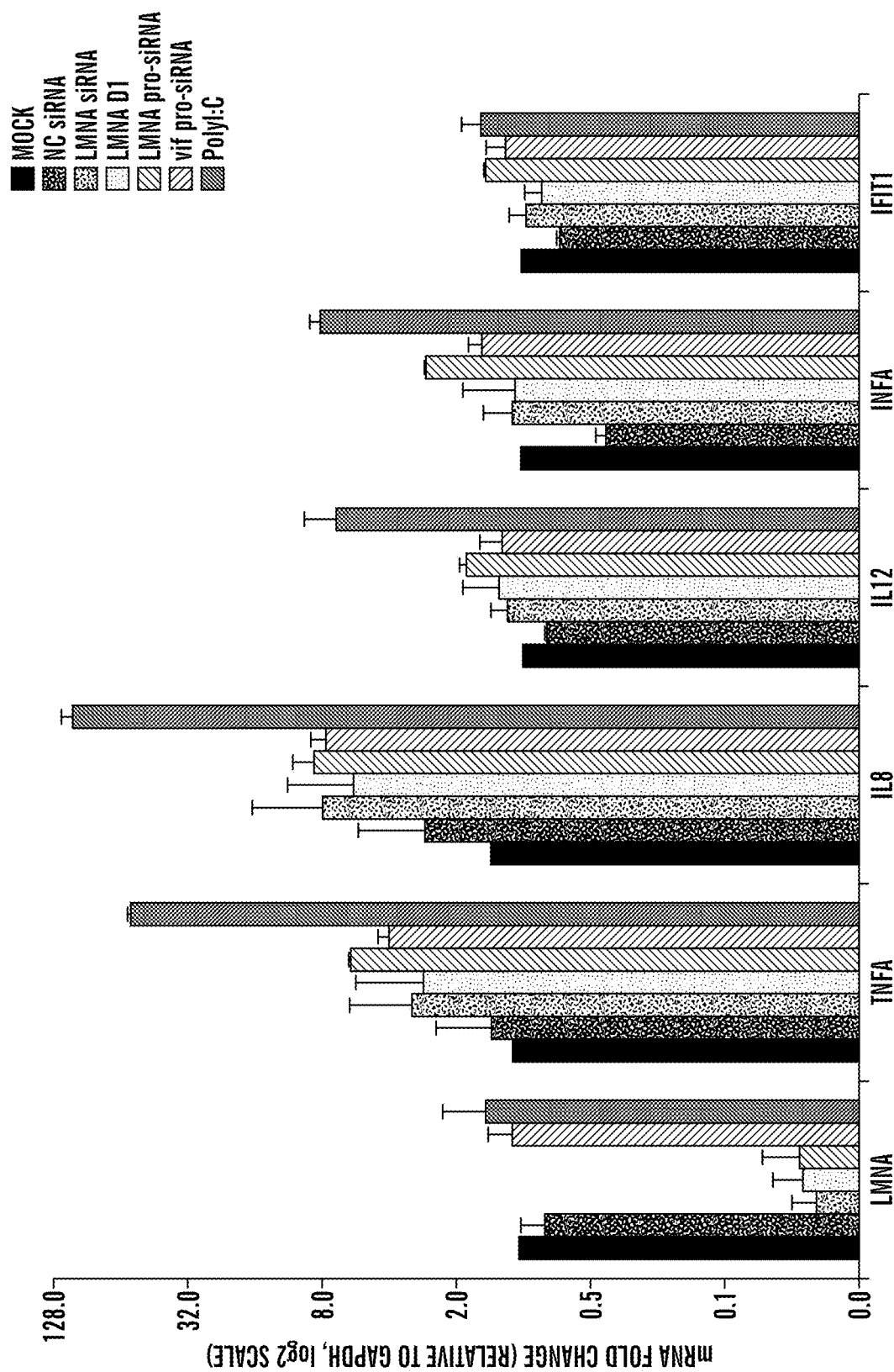

Because mammalian cells are sensitive to bacterial endotoxin, which stimulates off-target innate immunity via Toll-like receptor signaling, whether purified pro-siRNAs are contaminated with endotoxin was assessed. Although SDS-eluted pro-siRNAs contained significant amounts of endotoxin, assayed by Limulus amoebocyte lysate (LAL) assay, HPLC purified pro-siRNAs, even at concentrations as high as 320 nM, were below the limit of detection (0.25 EU/ml) (Table 1). Endotoxin contamination was tested for by assaying for induction of mRNA expression of the proinflammatory cytokines TNFA, IL6, IL8 and IL12, measured 4 hr later by qRT-PCR in highly endotoxin-sensitive monocyte-derived human macrophages (FIG. 10A). Incubation with HPLC-purified vif pro-siRNAs (320 nM) did not trigger cytokine gene expression. Thus purified pro-siRNAs did not contain significant amounts of immunostimulatory endotoxin. Next MDMs were transfected with a few siRNAs and pro-siRNAs (at 20 nM) to test immune response mediated by endogenous immune sensors (FIG. 10B). siRNA and pro-siRNA against LMNA efficiently down regulated LMNA mRNA, indicating these siRNAs were successfully transfected into MDMs. Comparing to siRNAs, pro-siRNAs did not trigger excessive activation of immune genes.

Figure 4A:
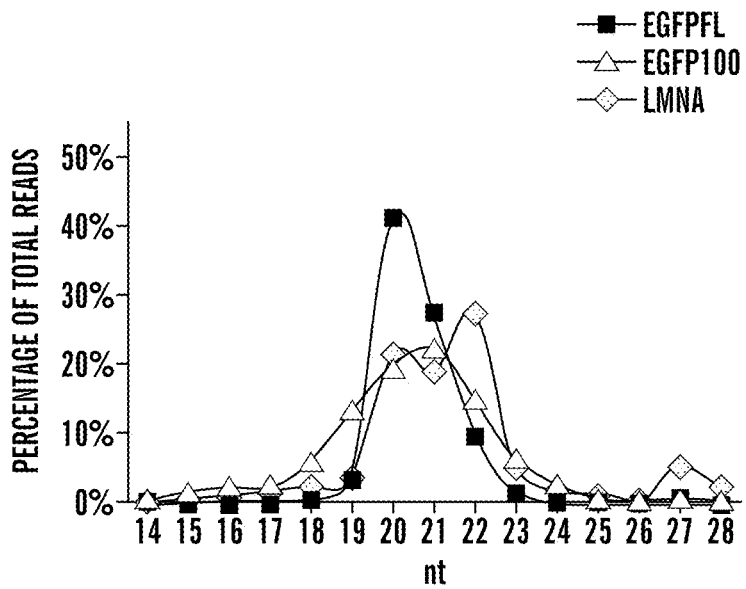
FIGS. 4A-4F demonstrating pro-siRNA sequences and tests of off-target effects.
Figure 4B:
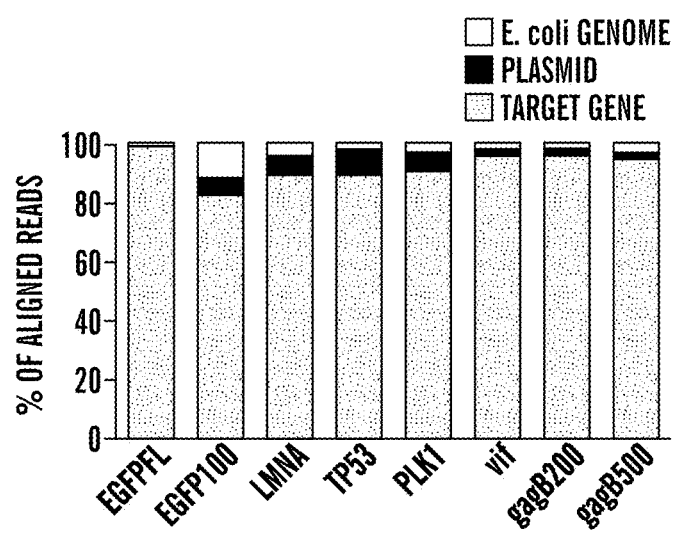
Figure 4C:
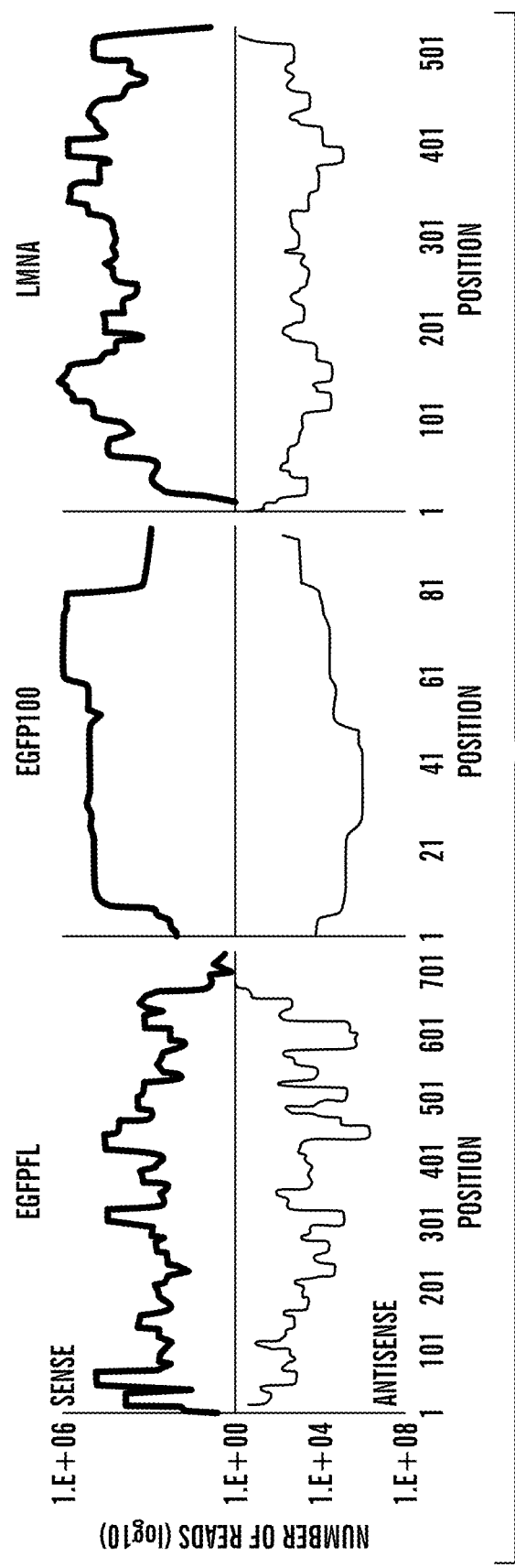
Figure 11:
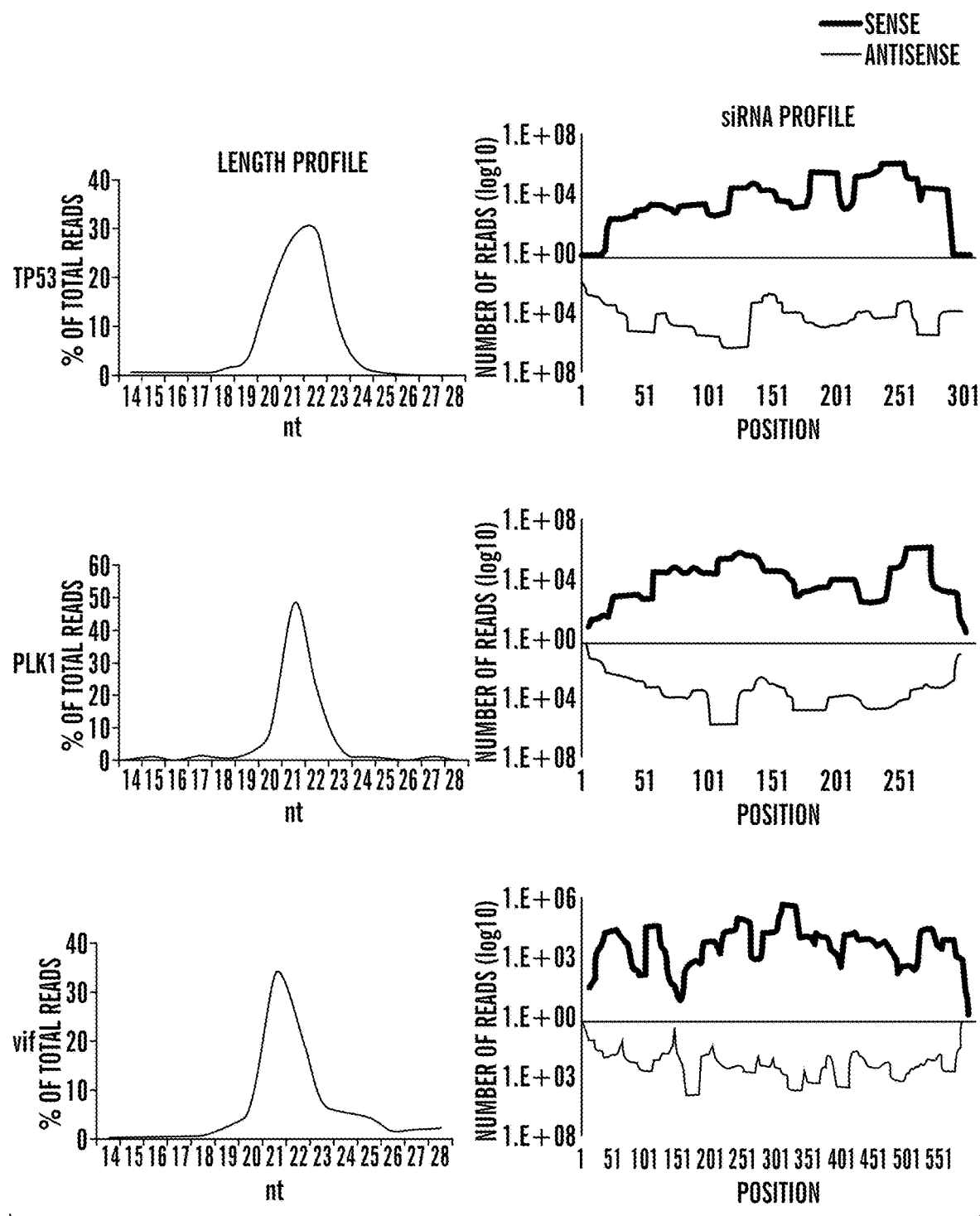
FIG. 11 depicts length profile and distribution of deep sequencing reads aligned to the pro-siRNA target sequences.
Figure 12A:
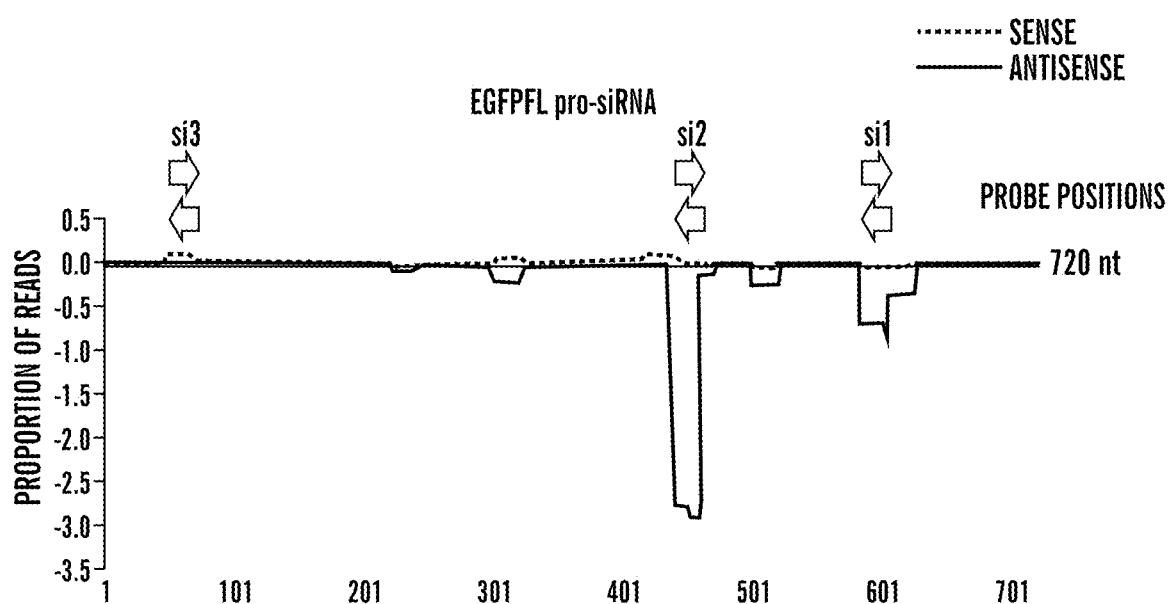
FIGS. 12A-12E demonstrate a test of strand bias and validation of pro-siRNA 'hot spots' for EGFPFL pro-siRNA.
Figure 12B:
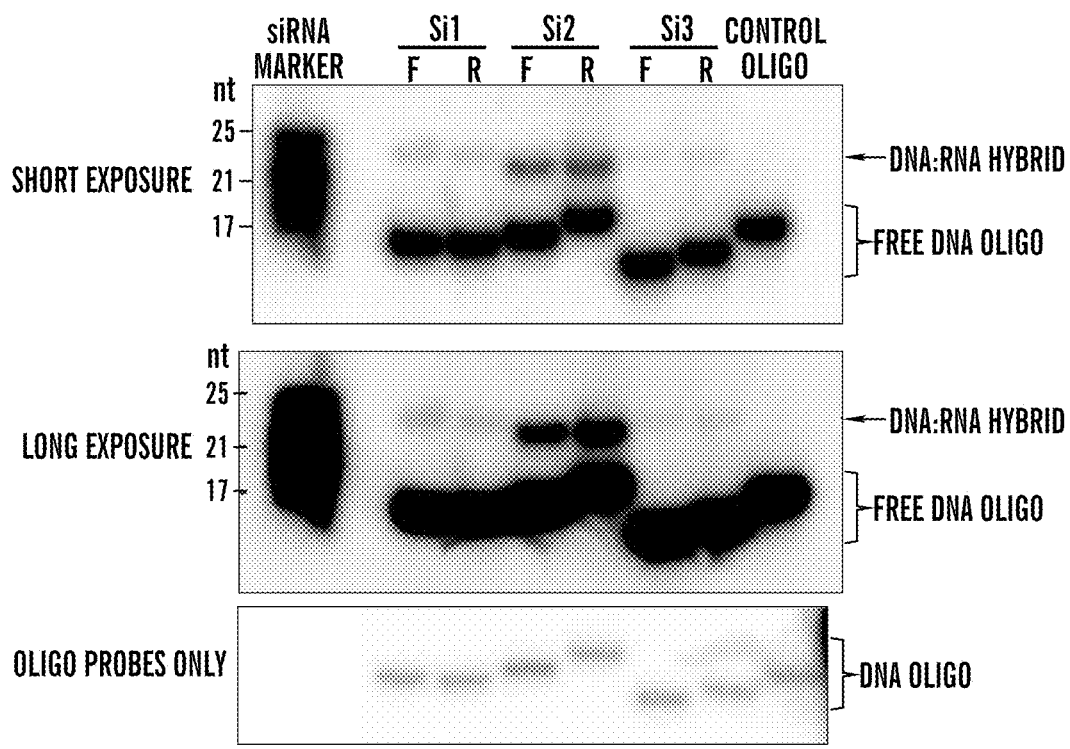
Figure 12C:
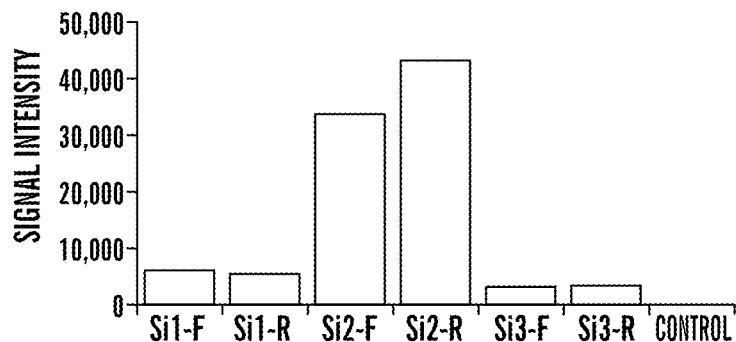
Figure 12D:
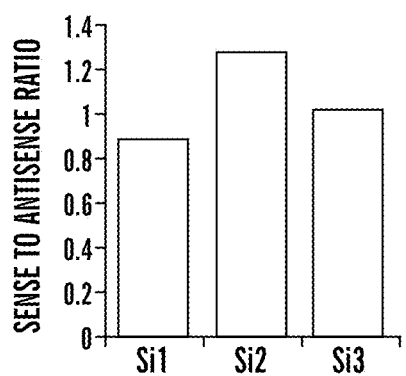
Figure 12E:
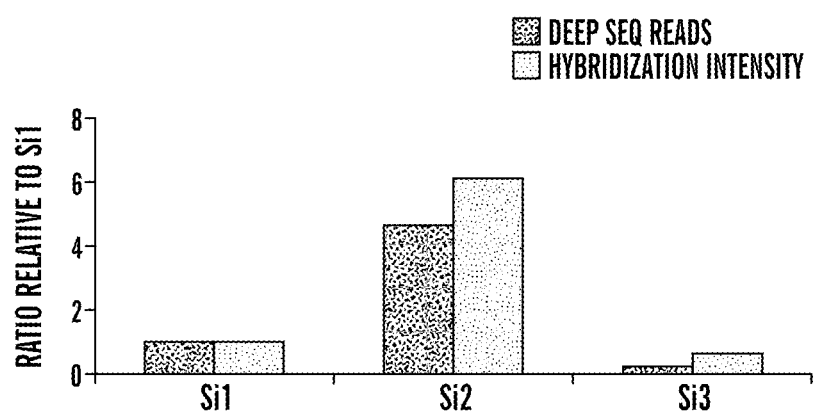

To ascertain the sequence composition of pro-siRNAs, pro-siRNAs were cloned and deep sequenced using a cloning method established for eukaryotic siRNAs (sequencing reads and alignment summary in Table 2). Most reads were concentrated between 20 and 22 nt (FIGS. 4A and 11). The majority of reads (on average ~75%) aligned to the target sequence, plasmid backbone or the E. coli genome. The vast majority of aligned sequences (82-99%) originated from the target sequence (FIG. 4B); consistent with the efficient gene knockdown they induced. Reads were generated from the entire target sequence, but were also concentrated at specific sites ('hot spots') (FIGS. 4C, 11, and 12A-E). There was some sequence strand bias for most of the hot spots (FIG. 12A). Because the data (FIGS. 2C and 2F) strongly suggested that pro-siRNAs are double stranded, it was possible that strand bias may have been due to differences in ligation efficiency during cloning, a well-known problem[25], rather than the presence of many single-stranded RNAs. To evaluate this further, forward and reverse DNA oligonucleotide probes (26-27 nt) were designed for three EGFPFL pro-siRNA hot spots and performed solution hybridization and native gel electrophoresis (Table 3 and FIG. 12B). The relative intensity of hybridized bands was approximately equal for sense and antisense probes for each hot spot and were generally correlated with the number of reads from each hot spot (FIGS. 12C-12E). Thus, pro-siRNAs are mostly dsRNAs and the strand bias in the deep sequencing data likely reflects ligation bias during cloning.

Figure 13A:
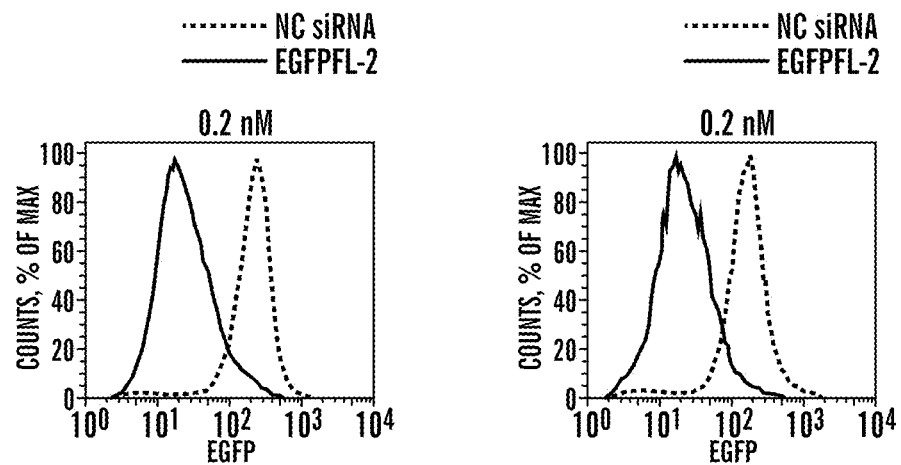
FIGS. 13A-13E demonstrate the similarity of EGFPFL pro-siRNA sequence contents and hot spot patterns obtained in two independent pro-siRNA preparations. Graphs are depicted, comparing gene knockdown of EGFP measured by flow cytometry (FIG. 13A) sequence content (FIG. 13B), length profile (FIG. 13C) and distribution (FIG. 13D) of deep sequencing reads of two independent EGFPFL pro-siRNAs (EGFPFL-1 and EGFPFL-2).
Figure 13B:
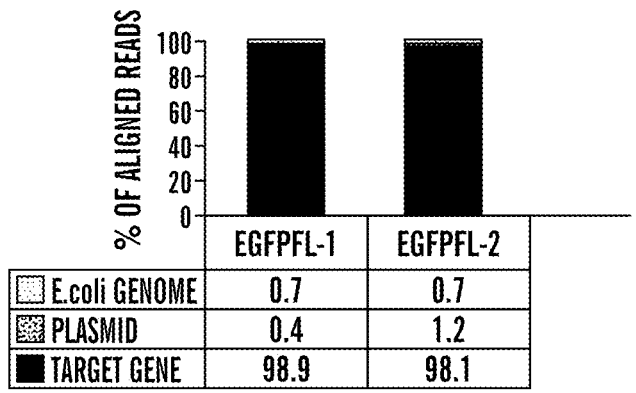
Figure 13C:
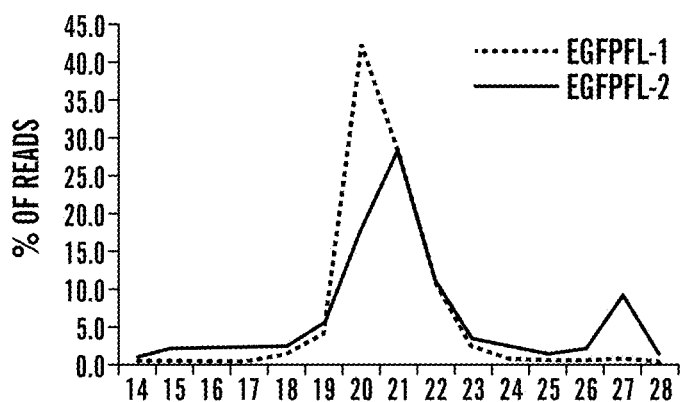
Figure 13D:
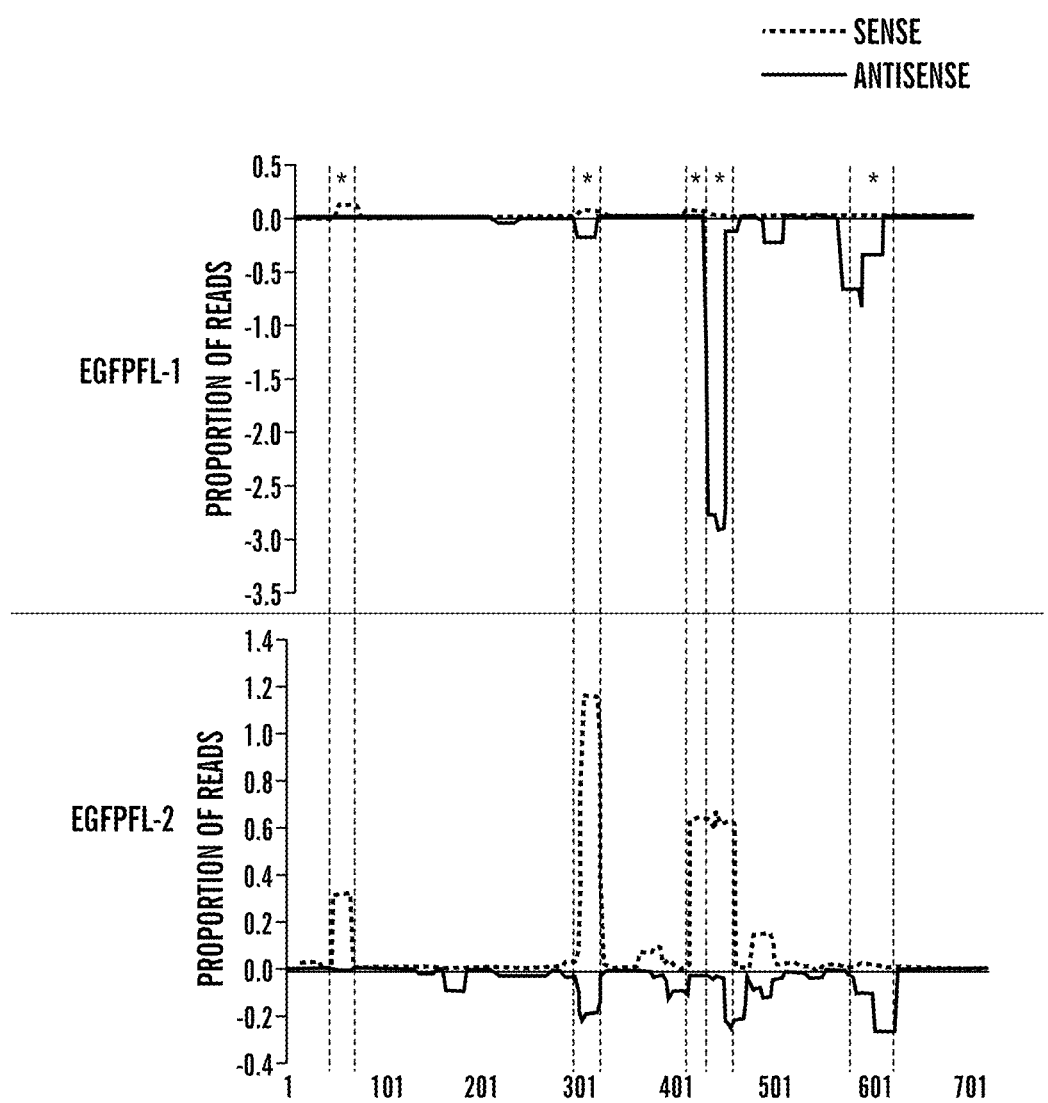
Figure 13E:
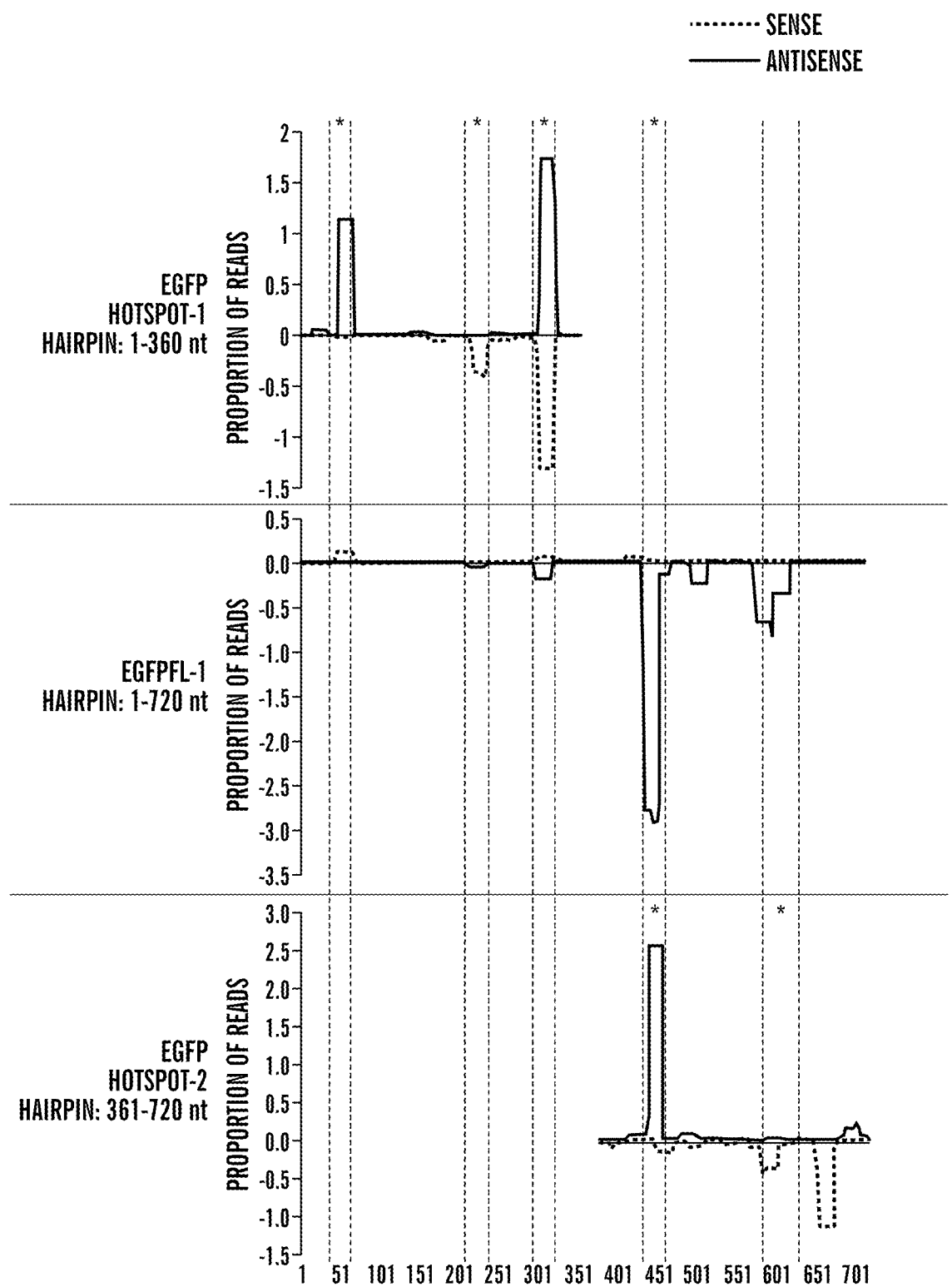

To further investigate the hot spot pattern, siRNA profiles of two independent preparations of EGFPFL pro-siRNAs cloned using different sets of adapters were compared. The potency, size profile and sequence content of two EGFPFL pro-siRNAs were similar, but not identical. The most abundant hot spots were consistent in the 2 samples, but the strand bias changed with the adapters, consistent with cloning bias (FIG. 13A-D). Without wishing to be bound by theory, hot spots could be due to intrinsic sequence preferences for RNase III cleavage or differences in stability or p19 binding after cleavage. To determine whether 'hot spots' are determined by sequence differences at or close to the hot spot, hairpins of equal sizes were constructed from the 5' and 3' ends of the full length EGFP sequence. The pro-siRNAs generated from the two halves yielded mostly identical hot spots to the corresponding hot spots in EGFPFL pro-siRNAs (FIG. 13E). Thus hot spots seem to be determined by local sequence differences. However a basic bioinformatic analysis of sequence motif or preferred base for the hot spots was inconclusive (data not shown). E. coli RNase III might process dsRNA into siRNA-sized small RNAs in vivo through a mechanism that differs from Dicer[27], whose cleavage of a long dsRNA results in phased and evenly distributed sequences along a target gene.

Figure 4D:
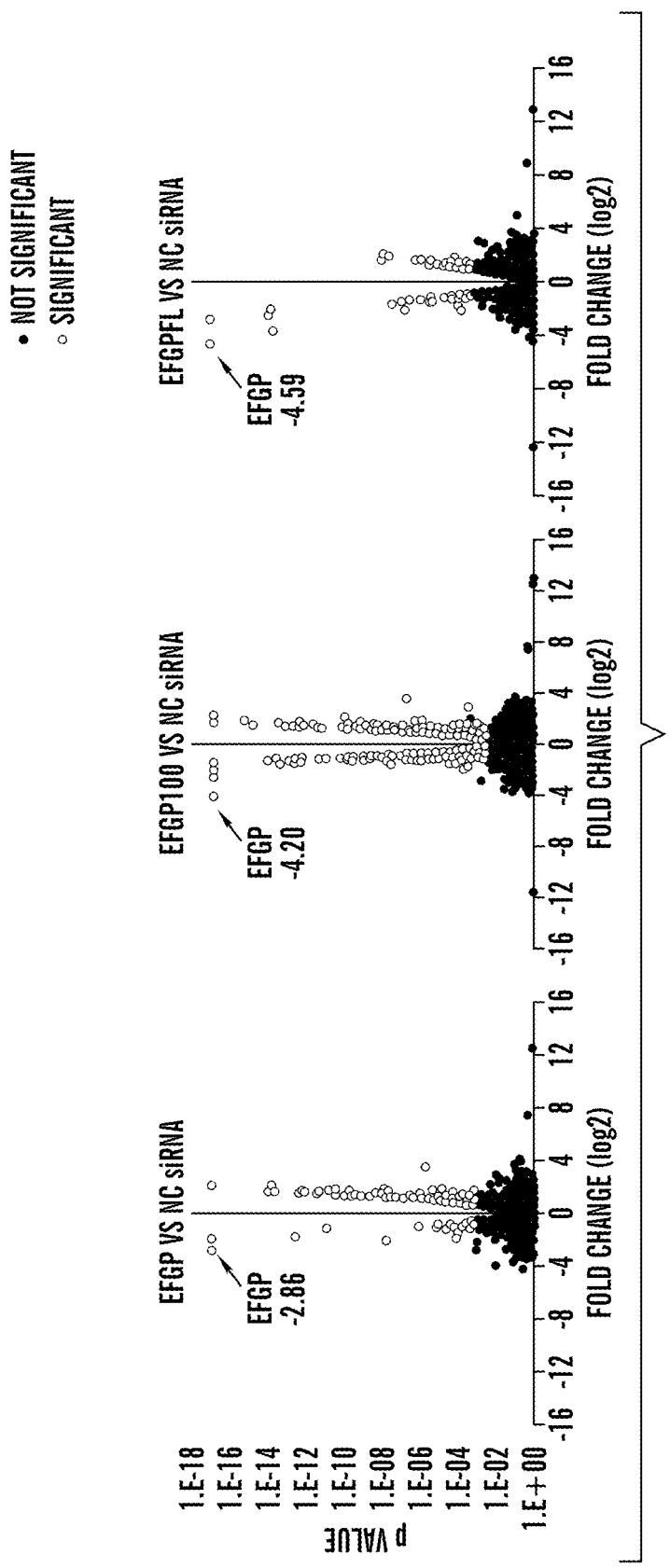
Figure 4E:
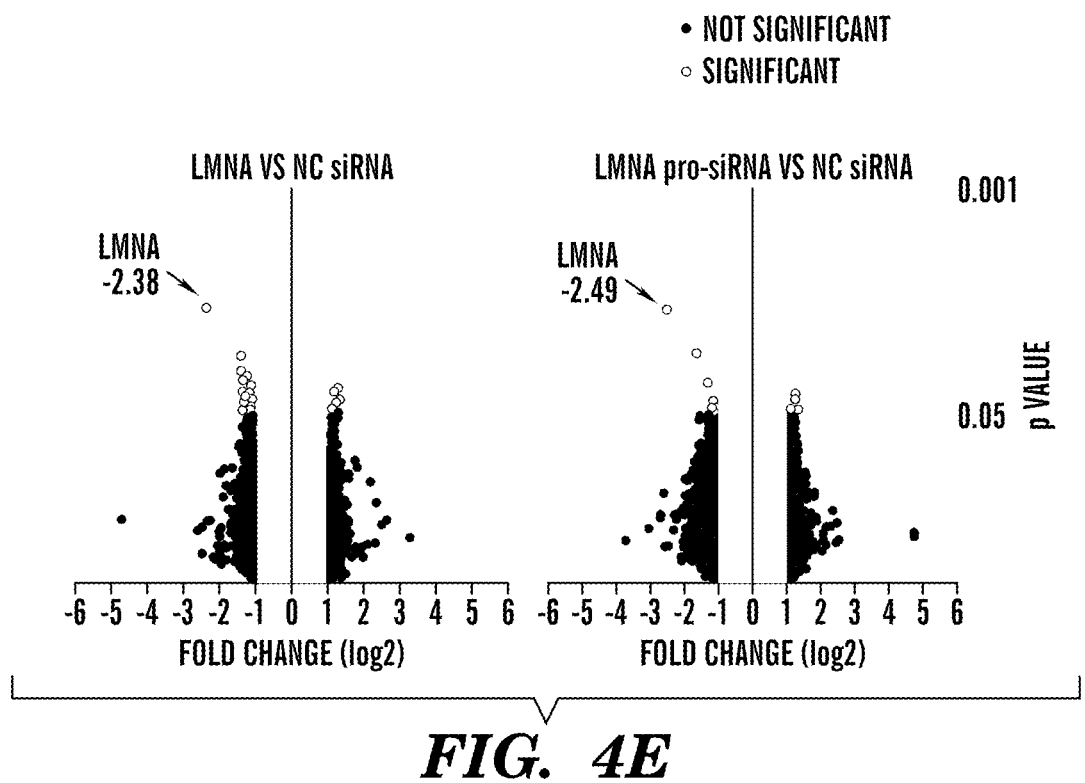
Figure 4F:
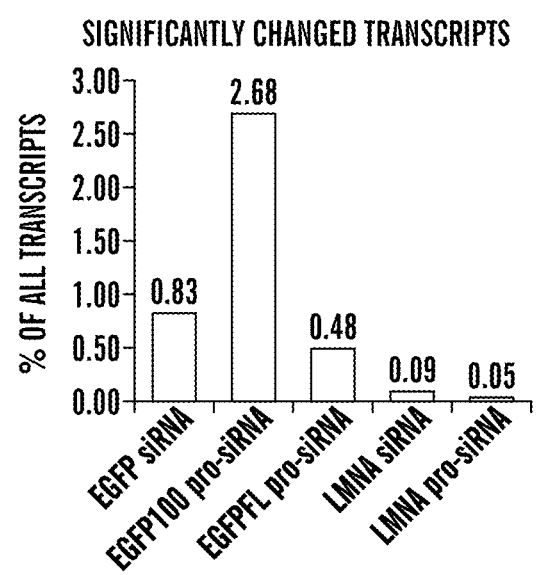
Figure 14A:
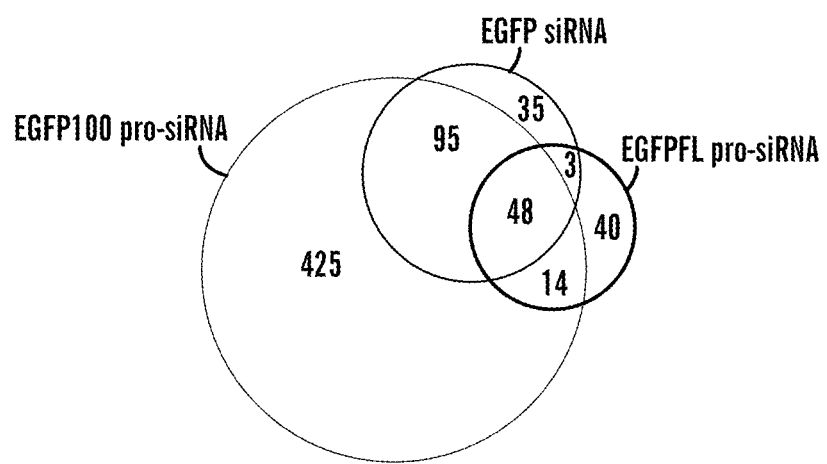
FIG. 14D depicts Venn diagrams for significantly changed genes in HeLa-d1EGFP cells transfected with EGFP siRNAs or pro-siRNAs.
FIG. 14B depicts volcano plots of expression changes versus p value of all annotated lincRNA by RNA deep sequencing in HeLa-d1EGFP cells transfected with EGFP siRNAs or pro-siRNAs relative to expression in cells transfected with a negative control (NC) siRNA. Cut-off of significance is q_value<0.05 (default in Cufflinks).
FIG. 14C depicts graphs of the number of significantly changed lincRNAs.
Figure 14B:
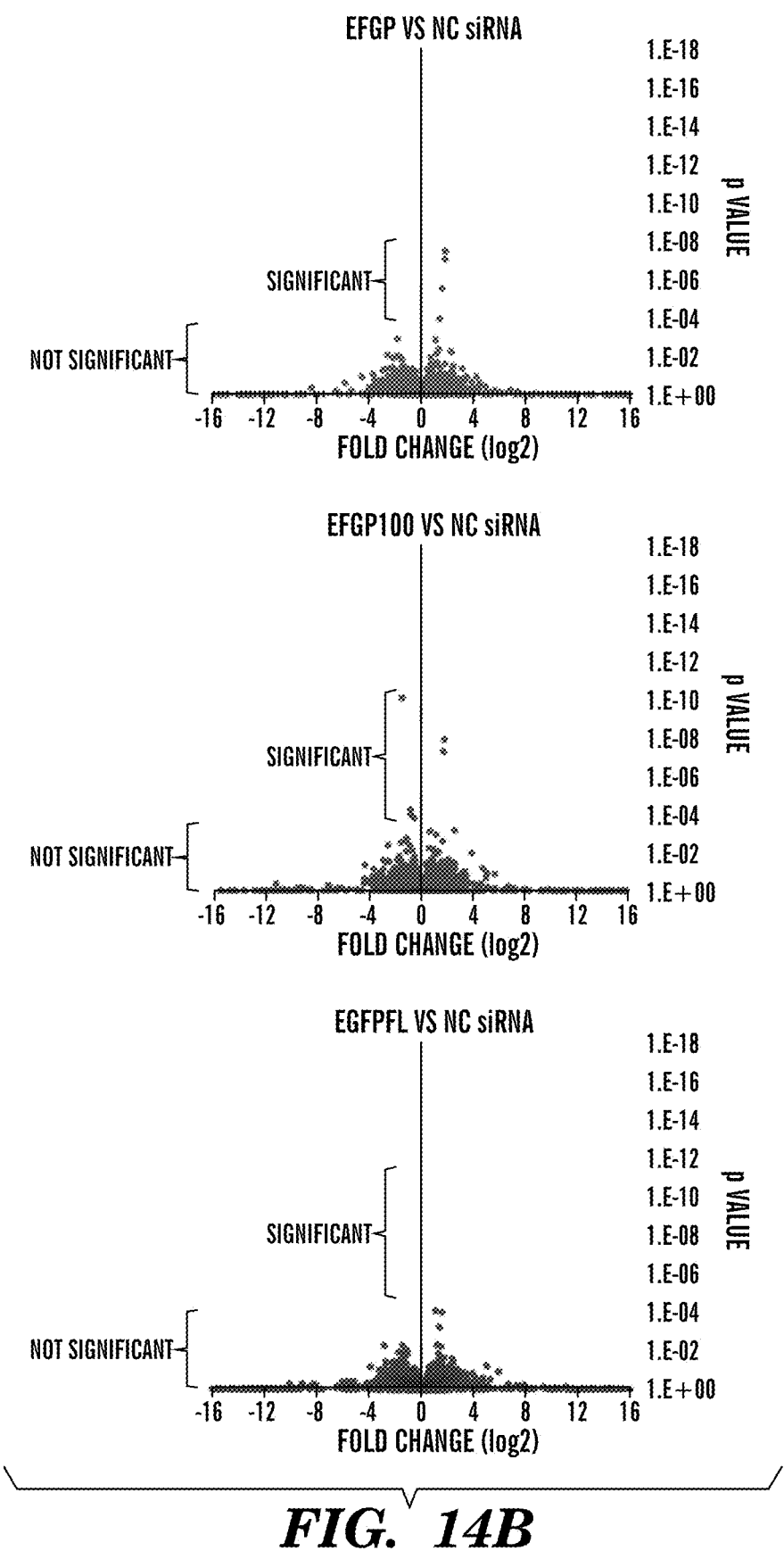
Figure 14C:
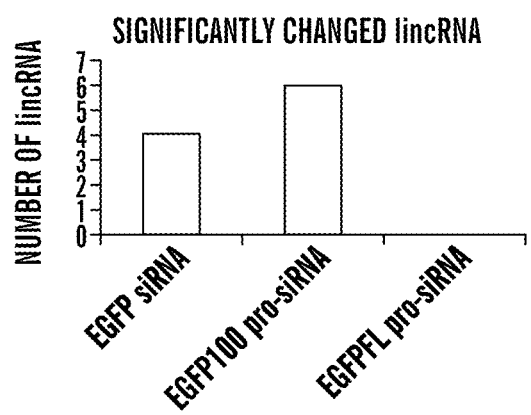
Figure 14D:
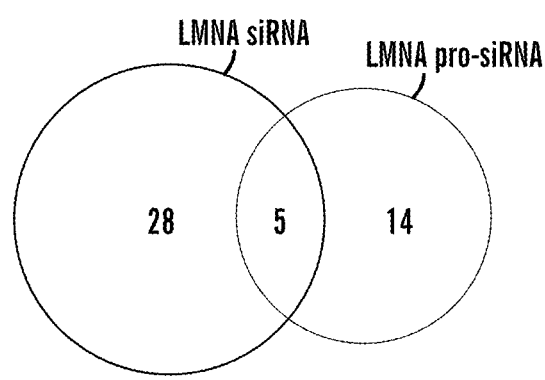

Because pro-siRNAs contained non-targeting sequences derived from the plasmid or E. coli genome, possible off-targeting effects[26] were investigated. To evaluate off-targeting, RNA expression profiles were compared by RNA deep sequencing of HeLa-d1EGFP cells transfected with 4 nM of negative control or EGFP siRNA or EGFPFL or EGFP100 pro-siRNAs (sequencing reads and alignment summary in Table 2). Tophat and Cufflinks were used to analyze the data and plotted volcano plots of all annotated transcripts (fold change versus p value, FIG. 4D). Comparing to EGFP siRNA, EGFP100 pro-siRNA had higher number of significantly changed genes while EGFPFL pro-siRNA had less (FIGS. 4F and 14A). EGFPFL pro-siRNA also produced the least changes in long non-coding RNAs, a group of newly discovered gene regulators (FIGS. 14B-14C). EGFP100 pro-siRNAs, made from a shorter hairpin (100 bp), contained higher proportion of plasmid and genomic sequences compared to other pro-siRNAs made from longer hairpins (200 to 720 bp, FIG. 4B), which is likely the cause of higher off-target effect. These data indicate a plasmid containing longer sequences of the target gene could have fewer off-target effects. Gene expression profiles of cells transfected with LMNA siRNAs and pro-siRNAs were also compared by microarray. Consistent with the EGFP data, LMNA pro-siRNAs, made from a longer hairpin (523 bp), produced fewer number of significantly changed genes comparing to LMNA siRNA (FIGS. 4E, 4F, and 14D). The RNA profiling data also showed the target gene was always the most down regulated gene and pro-siRNAs consistently produced better knockdown than siRNA. Thus pro-siRNAs could be engineered to offer better knockdown and lower off-target effects compared to synthetic siRNAs. The significantly changed genes in each of these experiments were not enriched for innate immune genes[30], confirming that the pro-siRNAs did not stimulate an innate immune response. Thus pro-siRNAs offer highly specific knockdown that is at least as good as synthetic siRNAs without the need to test multiple sequences.

Figure 15A:
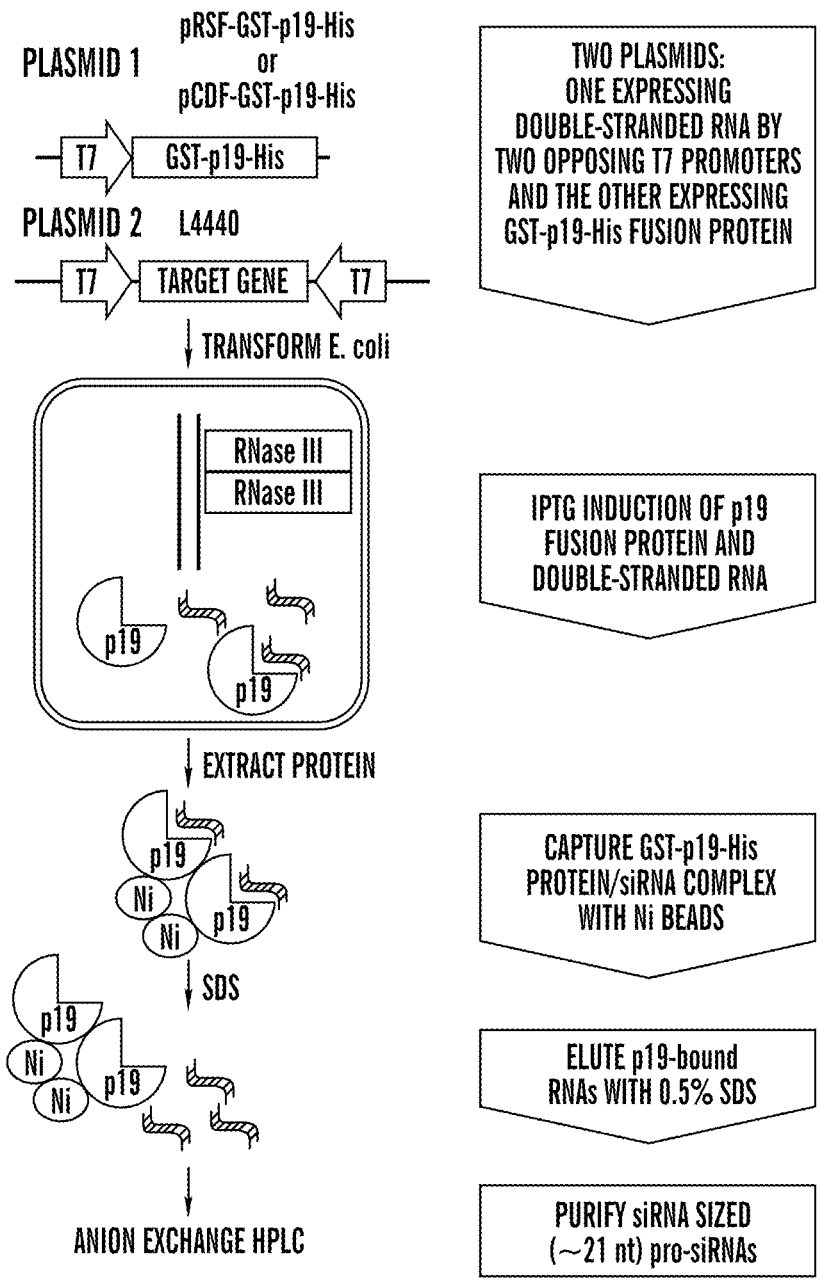
FIGS. 15A-15C demonstrate a two-plasmid alternate method for generating pro-siRNAs in E. coli.
Figure 15B:
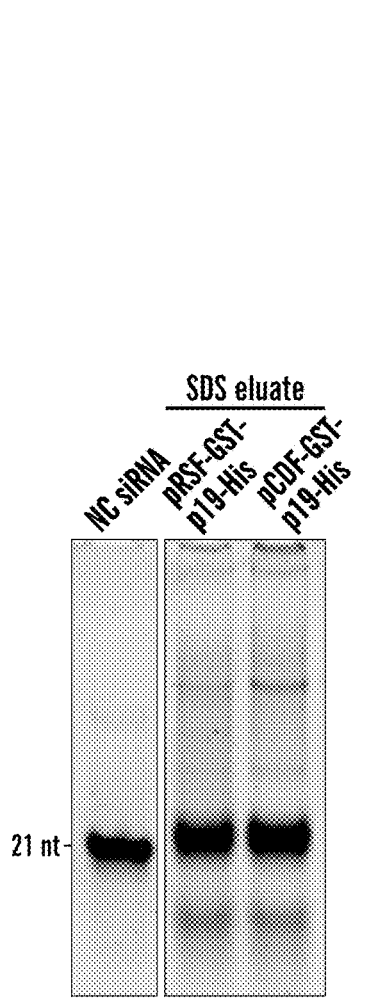
Figure 15C:
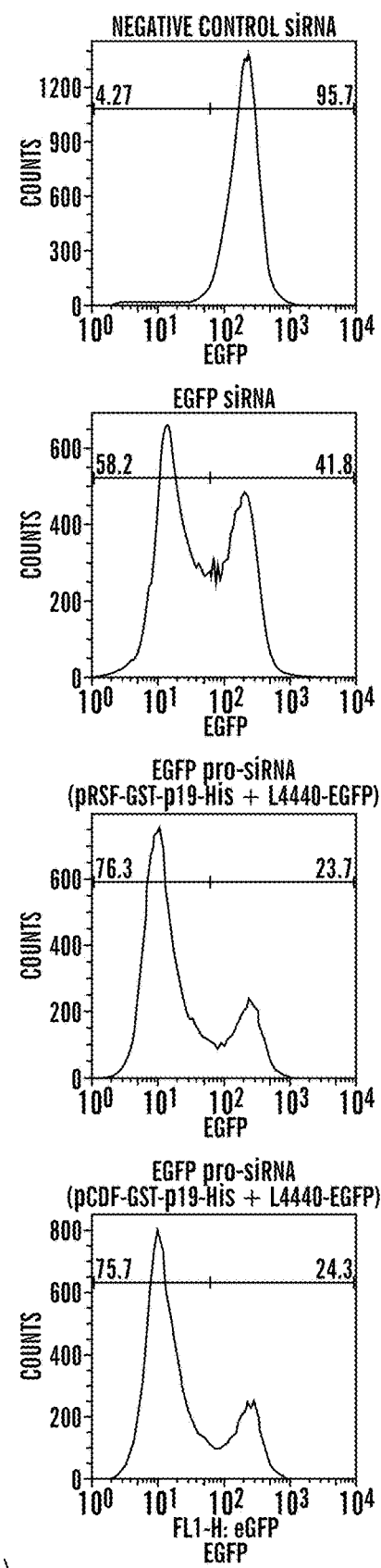

It is demonstrated herein that bacteria can be genetically engineered to produce siRNAs that are highly effective and not toxic to mammalian cells. Specifically, it demonstrated herein is efficient knockdown of one exogenous gene (EGFP), two viral genes (vif and gag) and 3 host genes (PLK1, TP53, LMNA). Without wishing to be bound by theory, because pro-siRNAs are natural products of RNase III, they likely have favorable ends (e. g., 5'-phosphate, 3'-hydroxyl and 3' overhangs) for efficient loading by Ago into the RISC and do not activate cytosolic innate immune RNA sensors. An alternative strategy of producing pro-siRNAs that uses two plasmids—one to express p19 and the other to transcribe both sense and antisense strands of a target sequence—facilitates cloning and can also be used to produce efficient gene silencing (FIGS. 15A-15C).

Figure 16:
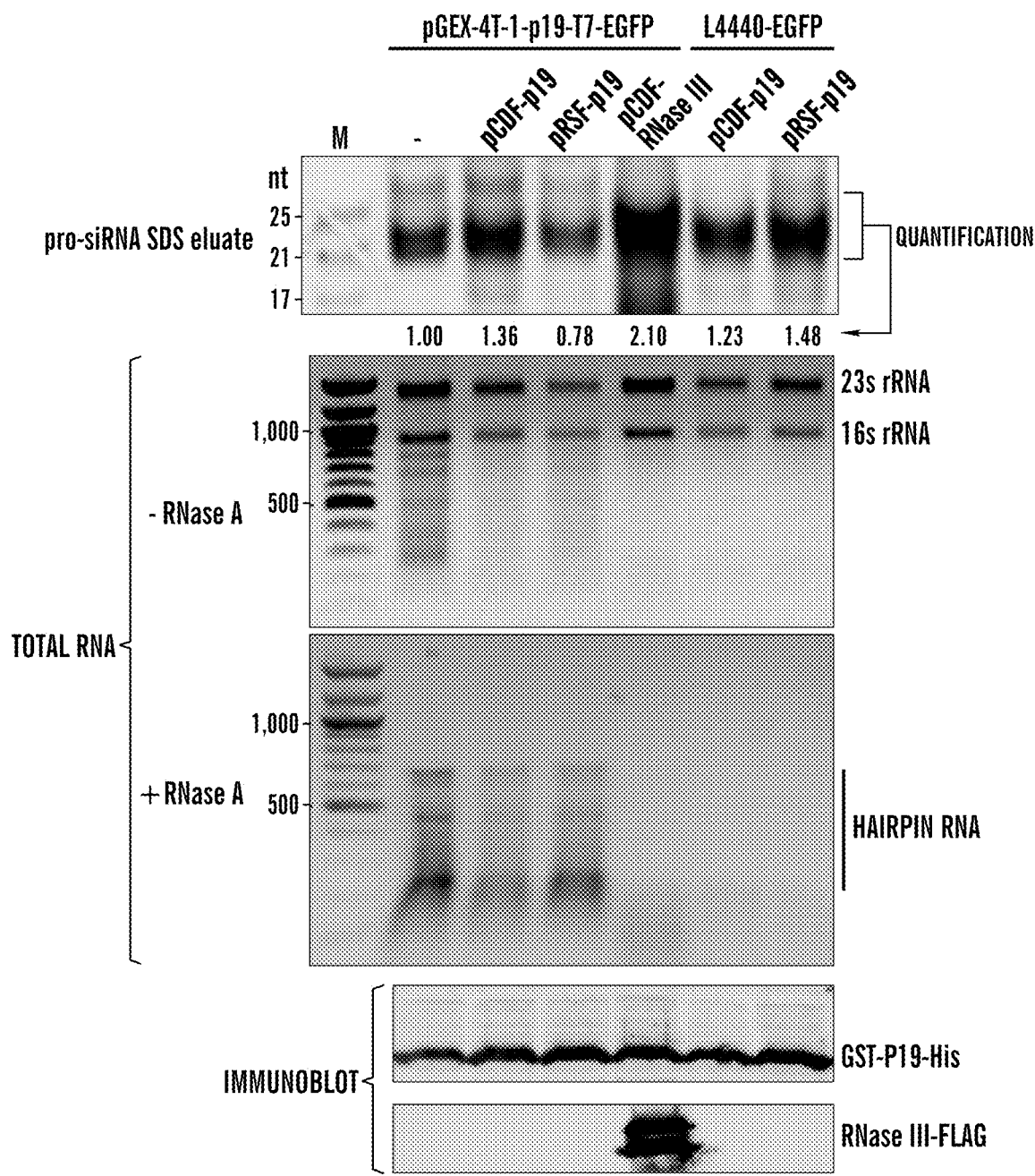
FIG. 16 demonstrates an exemplary method to improve yield of pro-siRNAs. pGEX-4T-1-p19-T7 plasmid containing EGFP hairpin (used to make EGFPFL pro-siRNA) was co-transfected with p19 overexpressing plasmids (pCDF-p19 or pRSF-p19) or E. coli RNase III overexpressing plasmid (pCDF-RNase III). The two-plasmid system (FIGS. 15A-15C) of co-transfecting L4440-EGFP with pCDF-p19 or pRSF-p19 was also tested. All E. coli cells were cultured under the same conditions. pro-siRNAs were produced as in FIG. 2A and equal proportions of SDS eluate were separated on a native polyacrylamide gel and stained with SYBR Gold. ~21 nt small RNA band was quantified using Gel Logic software and signals were normalized to the band in the first sample lane. Total RNA samples extracted from E. coli cells of each condition, treated with or without RNase A, were separated on a 0.8% agarose gel containing EtBr. Immunoblots were performed to confirm expressing of p19 and RNase III. M, molecular weight marker.

Without much optimization an average yield of ~4 nmol (~42 μg) pro-siRNA per liter of E. coli culture was achieved. It is contemplated that the engineered plasmid or E. coli genome could potentially be further optimized to maximize yield and improve effectiveness. By way of non-limiting example, the yield of EGFPFL pro-siRNA could be doubled by overexpressing E. coli RNase III (FIG. 16).

Generating pro-siRNAs for research purposes might be more cost effective than purchasing and testing multiple individual chemically synthesized siRNAs. pro-siRNAs, containing multiple sequences, might offer fewer off-target effects than individual siRNAs and could be harder for the target gene to escape silencing by mutation. On the other hand, chemical synthesis provides the opportunity for chemical modifications to increase potency, enhance stability and reduce off-target effects or couple fluorophores or targeting moieties. Such modifications might also be possible for pro-siRNAs, either by adding modified ribonucleotides to bacterial cultures during IPTG induction or by performing the same coupling reactions with purified pro-siRNAs as are used to modify siRNAs, respectively.

RNase III-deficient E. coli expressing dsRNAs can be fed to C. elegans[18] and bacteria-derived dsRNAs can be applied to plants to induce specific gene knockdown[28]. However, gene silencing requires host Dicer and, unlike for mammalian cells, is enhanced in these organisms by RNA-dependent RNA polymerases that can amplify small amounts of RNA. More recently, genetically engineered E. coli, designed to express an invasin to induce bacterial uptake and listeriolysin, to allow bacterial RNAs to escape from phagolysosomes, delivered dsRNAs into the cytoplasm of human cells through "trans-kingdom RNAi" technology[29].

pro-siRNAs, described here, could become a valuable cost effective addition to existing RNAi techniques for both research and therapeutics. The method described herein for producing pro-siRNAs can easily be adopted and scaled-up in an industrial setting. It is contemplated that mammalian cDNA libraries could be used to generate pro-siRNA libraries, e.g. for siRNA screening pro-siRNAs, generated from longer hairpins containing multiple sequences, might offer fewer off-target effects than individual siRNAs and in the cases of virus infection or cancer might be harder for the target gene to escape from by mutation. On the other hand, chemical synthesis provides the opportunity for chemical modifications to increase potency, enhance stability and reduce off-target effects or to couple fluorophores or targeting moieties. Such modifications can be applied to pro-siRNAs, e.g. either by adding modified ribonucleotides to bacterial cultures during IPTG induction or by performing the same coupling reactions with purified pro-siRNAs as are used to modify siRNAs, respectively.

Methods

Bacterial strains and culture conditions. All E. coli strains used in this study are listed in Table 4. E. coli strain DH5α was used for cloning and for initial characterization of the siRNA-like RNA species. For recombinant protein expression and pro-siRNA production, T7 Express Iq (NEB), a BL21-derived E. coli strain was used. Two mutants of RNase III, rnc-14::DTn10 (Tet$^R$) and Drnc-38 (Kan$^R$) were utilized. These were moved by P1 transduction from parent strains HT115(DE3)[18] and SK7622[19] into E. coli strain MG1655 ΔlacZYA (also referred as MG1655 Δlac). All E. coli strains were cultured in LB broth, Lennox (BD) at 37° C. with shaking at 250 rpm and antibiotics when required were used at the following concentrations; carbenicillin (100 μg/ml), kanamycin (50 μg/ml), spectinomycin (50 μg/ml), tetracycline (12.5 μg/ml).

Listeria monocytogenes strain 10403S was cultured in brain-heart infusion medium (BD Biosciences) at 30° C. Transformation of bacterial cells was performed as previously described[32].

Genes and plasmids. The p19 gene used in this study was cloned from Tomato bushy stunt virus. All plasmids are listed in Table 5. To produce p19 in E. coli, pcDNA3.1+ (Invitrogen) was used to express the p19 protein with a C-terminal FLAG tag (pcDNA3.1-p19-FLAG) or an N-terminal His tag (pcDNA3.1-His-p19). Plasmid pcDNA3.1-TREX1-FLAG encodes a C-terminal FLAG-tagged TREX-protein. To express p19 in L. monocytogenes, pLIV-1-His-p19 plasmid was used, which encodes p19 with an N-terminal His tag cloned in pLIV-1 plasmid (gift of Darren Higgins, Harvard Medical School). E. coli RNase III with an N-terminal FLAG was cloned in pcDNA3.1+ and pCDF-1b (Novagen) plasmids.

Two strategies were used for pro-siRNA production in E. coli. In one approach p19-His was fused to GST in pGEX-4T-1 (to express GST-p19-His fusion protein). On the same plasmid we cloned a hairpin RNA expressing cassette consisting of inverted repeat separated by a 32 bp linker downstream of a T7 promoter. A scheme of the resulting plasmid, pGEX-4T-1-p19-T7, is showed in FIG. 13A-13D. The hairpin RNA sequences were: EGFPFL, the entire 720-bp EGFP coding sequence (from pEGFP-N1, Clontech); EGFP100, a 100 bp from nt 219 to 318; EGFP Hotspot-1 360 bp from nt 1 to 360; EGFP Hotspot-2 360 bp from nt 361 to 720; LMNA (NM_005572.3), 523 bp from nt 267 to 789; TP53 (NM_000546.5), 301 bp from nt 376 to 676; PLK1 (NM_005030.3), 299 bp from nt 92 to 390; vif (K03455), the entire 579-bp; gag (K03455), gagB200: 200 bp from nt 1183 to 1382, gagB500: 500 bp from nt 1004 to 1503. (Genbank entries listed; numbers refer to position with respect to the translation start site).

In another approach two compatible plasmids were used for pro-siRNA production. The GST-p19-His protein was cloned under the control of the T7 promoter in pRSF-1b (Novagen) or pCDF-1b to generate pRSF-GST-p19-His and pCDF-GST-p19-His. The second plasmid is a L4440 plasmid encoding the entire EGFP coding sequence (L4440-EGFP).

All cloning was performed using PCR and standard techniques. All primers (with information for restriction enzyme sites) are listed in Table 6.

Cells. HeLa-d1EGFP, HCT116, HCT116 Dicer$^{-/-}$, HeLa-CD4 TZM-bl, U87.CD4.CXCR4 and U87.CD4.CCR5 cells were cultured in DMEM medium (Invitrogen) supplemented with 10% heat-inactivated fetal bovine serum (FBS). ACH2 cells (human leukemia T cell line CEM latently infected with HIV-1) were cultured in RPMI medium (Invitrogen) supplemented with 10% heat-inactivated fetal bovine serum (FBS). For assays using primary monocyte-derived human macrophages (MDM), monocytes were isolated from blood of a healthy donor by Ficoll-Paque Plus (GE Healthcare) density separation. Monocytes were plated on PRIMARIA plates (FALCON) in RPMI medium (Invitrogen) supplemented with 10% heat-inactivated human serum and adherent cells were cultured for 5 d to allow differentiation into macrophages.

RNA isolation and qRT-PCR. Total RNA was isolated from 3 ml of E. coli stationary phase culture with 1 ml Trizol reagent (Invitrogen) following the manufacturer's protocol. RNA from human cells was collected in Trizol and extracted according to the manufacturer's protocol. Total RNA (1 μg) was converted to cDNA using SuperScript III Reverse Transcriptase (Invitrogen). For qRT-PCR, 10 μl reaction, containing SsoFast EvaGreen mastermix (Bio-Rad), appropriate primers (Table 4), and template cDNAs made from 10 ng RNA, was amplified on a Bio-Rad CFX 96 Thermal Cycler. All qRT-PCR data were normalized to the human GAPDH gene. qRT-PCR primers for human genes (Table 6) were selected from PrimerBank (available on the world wide web at pga.mgh.harvard.edu/primerbank/).

siRNA isolation from total RNA using p19 magnetic beads. p19 magnetic beads were prepared at NEB as previously described[15]. To pull down siRNAs, 50 μg of total RNA (isolated from human or E. coli cells) was used following the manufacturer's protocol[15].

His-tag purification of GST-p19-His and bound pro-siRNA. GST-p19-His was purified as follows. A fresh single transformant of T7 Express Iq containing pGEX-4T-1-p19-T7 was used to inoculate 300 ml LB medium in a 1.5 L flask. When the $OD_{600}$ reached 0.3-0.6, protein and pro-siRNA expression were induced by adding 0.5 mM IPTG for 1 hr. Cells were centrifuged and lysed in 10 ml lysis buffer (50 mM Phosphate buffer pH 7.0, 300 mM NaCl, 10 mM imidazole, 1% Triton X-100, 1 mg/ml lysozyme) at 4° C. for ~30 min followed by sonication (Misonix S-4000) until the lysate was non-viscous. Following centrifugation the lysate was incubated with rotation with 1 ml Ni-NTA resin (Thermo Scientific) overnight at 4° C. The resin was washed with lysis buffer 4 times, each time for 10 min at 4° C. with rotation. Bound GST-p19-His was eluted in lysis buffer containing 300 mM imidazole at room temperature.

To purify p19-bound pro-siRNA the procedure was as above until the final elution step when 500 µl 0.5% SDS was added for 10 min at room temperature with rotation. This step was repeated and both SDS eluates were combined and passed through a 0.22 µm centrifuge filter (Corning) before HPLC purification on a Bio WAX NP5 anion exchange column (Agilent Technologies). The HPLC buffers were: Buffer A, 25 mM Tris-HCl, 2 mM EDTA; Buffer B, 25 mM Tris-HCl, 2 mM EDTA, 5 M NaCl. HPLC was initiated with a flow rate of 1 ml/min at 25° C. Elution was performed using a linear gradient of 0-10% Buffer B over 4 min, followed by 10% Buffer B for 6 min, and a second linear gradient of 10-25% Buffer B over 15 min at a reduced flow rate of 0.5 ml/min. pro-siRNA eluted in the second gradient was collected by isopropanol precipitation.

Polyacrylamide gel electrophoresis (PAGE) of RNA. For denaturing electrophoresis of RNA, mini-sized pre-cast 15% polyacrylamide TBE-Urea gels (Invitrogen) were used. RNA samples were heated to 95° C. for 5 min in Gel Loading Buffer II (Ambion) and then immediately placed on ice until gel loading. Electrophoresis was performed in a 70° C. water bath (to ensure complete denaturation of siRNA) and gels were stained with SYBR Gold (Invitrogen). For analysis of E. coli total RNA, 20 µg samples of Trizol-isolated RNA were loaded. RNA size standards (miRNA marker, siRNA marker and Low Range ssRNA Ladder) were from NEB.

For native electrophoresis of RNA, mini-sized homemade 15% polyacrylamide TBE gels were used with the Bio-Rad Mini-PROTEAN Tetra Cell. RNA samples were prepared in Gel Loading Buffer II (Ambion) without heat denaturation and electrophoresis was performed at room temperature.

Nuclease sensitivity assay. The nucleases tested were: RNase A, RNase T1, and Turbo DNase (all from Ambion), Xrn1, exonuclease T, and exonuclease I (all from NEB). For each assay, 200 ng of an unmodified synthetic negative control siRNA (GenePharma) and vifpro-siRNA were used and assays were incubated in a 20 µl reaction volume using standard amounts of enzymes at 37° C. for 1 hr. Treated RNAs were purified by phenol/chloroform extraction followed by isopropanol precipitation.

Test for endotoxin activity and immune activation in primary human monocyte-derived macrophages (MDM)/RNA samples diluted in ddH$_2$O to the indicated concentration were analyzed by the single vial Gel Clot LAL assay (detection limit 0.25 EU/ml, Lonza) following the manufacturer's protocol. Lipopolysaccharide (LPS) from E. coli O111:B4 (Sigma-Aldrich) was used as a positive control.

To test for cytokine gene activation, MDM plated in 24 well plates (1×10$^5$ cells/well) were incubated with medium containing RNA or LPS at the indicated concentration for 4 hr before harvesting RNA. siRNAs and pro-siRNAs were also transfected to MDMs at 20 nM using Lipofectamine 2000 (Invitrogen) and total RNA were harvest at 24 hrs after transfection.

5' $^{32}$P labeling of RNA. RNA samples were dephosphorylated by Antarctic Phosphatase (NEB) for 30 min at 37° C. in the presence of Murine RNase Inhibitor (NEB). The Antarctic Phosphatase was deactivated by incubation at 65° C. for 5 min and the RNA was end-labeled with γ-$^{32}$P ATP (PerkinElmer) and T4 Polynucleotide Kinase (NEB). Gels were exposed using a phosphorimager screen and visualized using a FLA-9000 Image Scanner (Fujifilm).

Small RNA northern blot. Northern blot for small RNAs was performed as previously described[33]. The EGFP specific sense probe was a $^{32}$P-UTP-internally labeled RNA prepared by in vitro transcription using T7 RNA polymerase (NEB) and a PCR-generated DNA template of the full-length EGFP gene that incorporated a T7 promoter.

siRNA transfection for testing RNA silencing efficiency. All siRNA transfections were performed using Lipofectamine 2000 following the manufacturer's protocol. Briefly, cells were plated in 24 well plates (1×10$^5$ per well) and the transfection complex (containing 1.0 ml Lipofectamine 2000 and siRNAs) was added directly to the medium. RNA and protein samples were isolated from cells 24 hr post-transfection. For the PLK1 cell killing experiment, cells were counted using a TC-10 automatic cell counter (Bio-Rad). The following siRNAs were used: ON-TARGETplus Non-targeting siRNA #4 (D-001810-04-05, Dharmacon), siGENOME Lamin A/C Control siRNA (D-001050-01-20, Dharmacon), Set of 4: siGENOME LMNA siRNA (MQ-004978-01-0002, Dharmacon), ON-TARGETplus SMARTpool-Human PLK1 (L-003290-00-0005, Dharmacon), Set of 4 Upgrade: ON-TARGETplus PLK1 siRNA (LU-003290-00-0002, Dharmacon), Set of 4: siGENOME TP53 siRNA (MQ-003329-03-0002, Dharmacon), Negative control siRNA (NC siRNA, B01001, GenePharma), Positive control siRNA TP53 (B03001, GenePharma), custom EGFP siRNA (sense, GGCUACGUCCAGGAGCGCACC (SEQ ID NO: 114); antisense, UGCGCUCCUGGACGUAGCCUU (SEQ ID NO: 115)), custom vif siRNA-1[23] (sense, GUUCAGAAGUACACAUCCCT (SEQ ID NO: 116); antisense, GGGAUGUGUACUUCUGAACTT (SEQ ID NO: 117)) and custom siRNA-2[24] (sense, CAGAUGGCAGGUGAUGAUUGT (SEQ ID NO: 118); antisense, AAUCAGCACCUGCCAUCUGTT (SEQ ID NO: 119)), custom gag siRNA: (sense, GAUUGUACUGAGAGACAGGCU (SEQ ID NO: 120); antisense, CCUGUCUCUCAGUACAAUCUU (SEQ ID NO: 121)).

RISC Immunoprecipitation. Cells (3×10$^6$) were transfected with 4 nM NC siRNA or EGFPFL pro-siRNAs. After 24 hours cells were scraped from the plate in 2 ml lysis buffer (150 mM KCl, 25 mM Tris-HCl pH 7.5, 2 mM EDTA, 0.5 mM DTT, 1% NP-40 and Roche Complete Protease Inhibitor Cocktail). Cells were then mechanically disrupted for 1 min using a micro-MiniBeadbeater (BioSpec). The cell lysate was incubated at 4° C. with rotation for 1 hr to ensure complete lysis. IP was performed by adding anti-Ago (2A8) antibody (Millipore, MABE56) or mouse total IgG (Jackson Labs) at 1:100 dilution together with 30 µl protein G Dynabeads (Invitrogen) and samples were rotated at 4° C. overnight. After washing 4 times in lysis buffer, precipitated RNAs were isolated using Trizol reagent from 90% of the reaction mix, while 10% was saved for immunoblot input.

Western Immunoblot. Protein samples were prepared by heating cells to 95° C. for 5 min in 1×SDS loading buffer before SDS-PAGE. Immunoblot was performed using SNAP i.d. Protein Detection System (Millipore) following the manufacturer's protocol. Antibodies and their dilutions were: anti-FLAG (M2) 1:1,000 (Sigma-Aldrich, F1804), anti-His tag 1:500 (Covance, MMS-156P), anti-PLK1 1:100 (Santa Cruz, sc-17783), anti-LaminA/C 1:1,000 (Santa Cruz, sc-7292), anti-p53 (DO-1) 1:500, (Santa Cruz, sc-126), anti-beta-Tubulin 1:10,000 (Sigma-Aldrich, T5168), anti-Ago (2A8) 1:1,000 (Millipore, MABE56). Horseradish peroxidase conjugated anti-mouse or anti-rabbit IgG secondary antibodies were used at 1:5,000 dilution followed by incubating the membranes in SuperSignal West Pico Chemiluminescent Substrate (Thermo Scientific).

Solution hybridization and native gel electrophoresis assay. DNA oligonucleotides purchased from IDT were PAGE purified. Purified DNA oligonucleotides (10 pmol) were end-labeled with $\gamma$-$^{32}$P ATP by T4 Polynucleotide Kinase (NEB) and 2 pmol was then mixed with 5 ng of pro-siRNAs in buffer containing 20 mM Tris-HCl pH 7.9, 100 mM NaCl and 2 mM EDTA. Samples were heated to 80° C. for 10 min and allowed to cool to room temperature. A fraction of the sample was separated on a native 15% polyacrylamide gel. The gel was directly exposed to a phosphorimager screen. Multi-gauge software (Fujifilm) was used for image quantification.

siRNA library preparation, deep sequencing, and data analysis. siRNAs were cloned according to the Illumina small RNA sample preparation guide v1.5 with the following exceptions. Custom 5' RNA ligation adapters were synthesized with a 4 nt nucleotide barcode sequence (Table 7). Small RNA libraries were pooled and sequenced on one sequencing lane of an Illumina GAII sequencer (Genome Technology Core, Whitehead Institute or NEB). Novocraft software (www.novocraft.com) was used for sequence alignment. Reference genome was *E. coli* K12 substr. MG1655. We wrote Perl software scripts for data analysis. Original data and software scripts are available upon request.

mRNA profiling by microarray and deep sequencing. siRNAs and pro-siRNAs (4 nM) were transfected into HeLa-d1EGFP cells and RNA was isolated 24 hr post-transfection. Non-targeting siRNA #4 (Dharmacon) was used as negative control siRNA. Data from biological duplicates were analyzed at the Microarray Core, Dana Farber Cancer Institute for microarray analysis using GeneChip 1.0 ST (Affymetrix). Microarray data was analyzed using dChip software and p values of gene expression changes were calculated using paired T-test method[34]. Original data and analysis files are available upon request.

For RNA deep sequencing, Ribo-Zero rRNA Removal Kits (Epicentre) was used to remove large ribosomal RNAs from total RNA following the manufacturer's protocol. rRNA-depleted RNA (from 500 ng total RNA) was used to construct deep sequencing library using NEBNext Ultra RNA Library Prep Kit for Illumina (NEB #E7530) according to the manufacturer's protocol. Illumina GAII was used for sequencing (NEB). Tophat and Cufflinks software suites were used to analyzed the RNA deep sequencing data from biological duplicates. Reference genome was Human genome GRCh37/hg19 and annotations of lincRNA transcripts were downloaded from UCSD genome browser. Original data and analysis files are available upon request.

Flow cytometry. For EGFP, cells were removed from plates by trypsin digestion and re-suspended in FACS buffer, DPBS (Invitrogen) containing 2% heat-inactivated FBS. Intracellular staining of p24 antigen was performed using an Intracellular Staining Kit (Invitrogen) according to the manufacturer's protocol and fluorescein-labeled p24 antibody (1:200, Beckman Coulter, cat#KC57-FITC). Fluorescence was analyzed on a FACSCalibur (BD) using FlowJo software (Tree Star).

HIV infection and TZM-bl assay. HeLa-CD4 cells were transfected with 4 nM siRNA and pro-siRNA in 24 well plates ($1 \times 10^5$ cells/well). Cells were infected 12 hr post-transfection with HIV$_{IIIB}$ (~400 ng/ml p24) and culture medium was changed 12 hr post-infection. For HIV$_{UG29}$ U87.CD4.CXCR4 cells were used and for HIV$_{IN22}$ U87.CD4.CCR5 cells were used. Culture medium was collected for TZM-bl assay and RNA was extracted for qRT-PCR 24~36 hr post-infection. TZM-bl cells, plated in 24 well plates ($1 \times 10^5$ cells/well) 12 hr before, were analyzed 24 later by luciferase assay performed using a Luciferase Assay System kit (Promega) following the manufacturer's protocol.

RNase A digestion assay for *E. coli* total RNA. ~2 ug of total *E. coli* RNA were incubated with 1.0 unit of RNase A for 15 min at 37° C. in 1×DNase I reaction buffer (NBE) supplemented with 400 mM NaCl. The resulting products were analyzed on a 0.8% agarose gel containing EtBr.

REFERENCES

1. Fire, A. et al. Potent and specific genetic interference by double-stranded RNA in *Caenorhabditis elegans*. *Nature* 391, 806-811 (1998).
2. Hamilton, A. J. & Baulcombe, D. C. A species of small antisense RNA in posttranscriptional gene silencing in plants. *Science* 286, 950-952 (1999).
3. Lejeune, E. & Allshire, R. C. Common ground: small RNA programming and chromatin modifications. *Curr Opin Cell Biol* 23, 258-265 (2011).
4. Elbashir, S. M. et al. Duplexes of 21-nucleotide RNAs mediate RNA interference in cultured mammalian cells. *Nature* 411, 494-498 (2001).
5. Caplen, N. J., Parrish, S., Imani, F., Fire, A. & Morgan, R. A. Specific inhibition of gene expression by small double-stranded RNAs in invertebrate and vertebrate systems. *Proc Natl Acad Sci USA* 98, 9742-9747 (2001).
6. Rettig, G. R. & Behlke, M. A. Progress toward in vivo use of siRNAs-II. *Mol Ther* 20, 483-512 (2012).
7. Timmons, L. & Fire, A. Specific interference by ingested dsRNA. *Nature* 395, 854 (1998).
8. Myers, J. W., Jones, J. T., Meyer, T. & Ferrell, J. E., Jr. Recombinant Dicer efficiently converts large dsRNAs into siRNAs suitable for gene silencing. *Nat Biotechnol* 21, 324-328 (2003).
9. Yang, D. et al. Short RNA duplexes produced by hydrolysis with *Escherichia coli* RNase III mediate effective RNA interference in mammalian cells. *Proc Natl Acad Sci USA* 99, 9942-9947 (2002).
10. Morlighem, J. E., Petit, C. & Tzertzinis, G. Determination of silencing potency of synthetic and RNase III-generated siRNA using a secreted luciferase assay. *Biotechniques* 42, 599-605 (2007).
11. Semizarov, D. et al. Specificity of short interfering RNA determined through gene expression signatures. *Proc Natl Acad Sci USA* 100, 6347-6352 (2003).
12. Voinnet, O., Pinto, Y. M. & Baulcombe, D. C. Suppression of gene silencing: a general strategy used by diverse DNA and RNA viruses of plants. *Proc Natl Acad Sci USA* 96, 14147-14152 (1999).
13. Silhavy, D. et al. A viral protein suppresses RNA silencing and binds silencing-generated, 21- to 25-nucleotide double-stranded RNAs. *Embo J* 21, 3070-3080 (2002).

14. Vargason, J. M., Szittya, G., Burgyan, J. & Hall, T. M. Size selective recognition of siRNA by an RNA silencing suppressor. *Cell* 115, 799-811 (2003).
15. Jin, J., Cid, M., Poole, C. B. & McReynolds, L. A. Protein mediated miRNA detection and siRNA enrichment using p19. *Biotechniques* 48, xvii-xxiii (2010).
16. Chu, M., Desvoyes, B., Turina, M., Noad, R. & Scholthof, H. B. Genetic dissection of tomato bushy stunt virus p19-protein-mediated host-dependent symptom induction and systemic invasion. *Virology* 266, 79-87 (2000).
17. Knight, S. W. & Bass, B. L. A role for the RNase III enzyme DCR-1 in RNA interference and germ line development in Caenorhabditis elegans. *Science* 293, 2269-2271 (2001).
18. Timmons, L., Court, D. L. & Fire, A. Ingestion of bacterially expressed dsRNAs can produce specific and potent genetic interference in Caenorhabditis elegans. *Gene* 263, 103-112 (2001).
19. Babitzke, P., Granger, L., Olszewski, J. & Kushner, S. R. Analysis of mRNA decay and rRNA processing in *Escherichia coli* multiple mutants carrying a deletion in RNase III. *J Bacteriol* 175, 229-239 (1993).
20. Cummins, J. M. et al. The colorectal microRNAome. *Proc Natl Acad Sci USA* 103, 3687-3692 (2006).
21. Jackson, A. L. et al. Position-specific chemical modification of siRNAs reduces "off-target" transcript silencing. *Rna* 12, 1197-1205 (2006).
22. Spankuch, B. et al. Cancer inhibition in nude mice after systemic application of U6 promoter-driven short hairpin RNAs against PLK1. *J Natl Cancer Inst* 96, 862-872 (2004).
23. Lee, S. K. et al. Lentiviral delivery of short hairpin RNAs protects CD4 T cells from multiple clades and primary isolates of HIV. *Blood* 106, 818-826 (2005).
24. Sugiyama, R., Habu, Y., Ohnari, A., Miyano-Kurosaki, N. & Takaku, H. RNA interference targeted to the conserved dimerization initiation site (DIS) of HIV-1 restricts virus escape mutation. *J Biochem* 146, 481-489 (2009).
25. Jayaprakash, A. D., Jabado, O., Brown, B. D. & Sachidanandam, R. Identification and remediation of biases in the activity of RNA ligases in small-RNA deep sequencing. *Nucleic Acids Res* 39, e141 (2011).
26. Jackson, A. L. et al. Expression profiling reveals off-target gene regulation by RNAi. *Nat Biotechnol* 21, 635-637 (2003).
27. Weinberg, D. E., Nakanishi, K., Patel, D. J. & Bartel, D. P. The inside-out mechanism of Dicers from budding yeasts. *Cell* 146, 262-276 (2011).
28. Tenllado, F., Martinez-Garcia, B., Vargas, M. & Diaz-Ruiz, J. R. Crude extracts of bacterially expressed dsRNA can be used to protect plants against virus infections. *BMC Biotechnol* 3, 3 (2003).
29. Xiang, S., Fruehauf, J. & Li, C. J. Short hairpin RNA-expressing bacteria elicit RNA interference in mammals. *Nat Biotechnol* 24, 697-702 (2006).
30. Zhao, H. F. et al. High-throughput screening of effective siRNAs from RNAi libraries delivered via bacterial invasion. *Nat Methods* 2, 967-973 (2005).
31. Nakanishi, K., Weinberg, D. E., Bartel, D. P. & Patel, D. J. Structure of yeast Argonaute with guide RNA. *Nature* 486, 368-374 (2012).
32. Dancz, C. E., Haraga, A., Portnoy, D. A. & Higgins, D. E. Inducible control of virulence gene expression in *Listeria monocytogenes*: temporal requirement of listeriolysin O during intracellular infection. *J Bacteriol* 184, 5935-5945 (2002).
33. Pall, G. S. & Hamilton, A. J. Improved northern blot method for enhanced detection of small RNA. *Nat Protoc* 3, 1077-1084 (2008).
34. Li, C. & Wong, W. H. Model-based analysis of oligonucleotide arrays: expression index computation and outlier detection. *Proc Natl Acad Sci USA* 98, 31-36 (2001).

TABLE 1

Gel clot Limulus amoebocyte lysate (LAL) endotoxin assays of HPLC-purified pro-siRNA

| Sample | Gel clot LAL assay (limit of detection 0.25 EU/ml) |
|---|---|
| H2O | − |
| LPS (4 ng/ml) | + |
| P19 RNA SDS eluate (~100 nM) | + |
| HPLC pro-siRNA 16 nM | − |
| HPLC pro-siRNA 64 nM | − |
| HPLC pro-siRNA 160 nM | − |
| HPLC pro-siRNA 320 nM | − |

TABLE 2

Sequencing reads and alignment summary of RNA deep sequencing data

| Type | Sample name | Total reads | Aligned reads | Percentage aligned |
|---|---|---|---|---|
| Total RNA | NC siRNA-1 | 21,954,641 | 19,032,496 | 86.7% |
| Total RNA | NC siRNA-2 | 26,914,681 | 22,462,181 | 83.5% |
| Total RNA | EGFP siRNA-1 | 25,659,586 | 21,237,241 | 82.8% |
| Total RNA | EGFP siRNA-2 | 23,235,174 | 19,588,652 | 84.3% |
| Total RNA | EGFP100 pro-siRNA-1 | 27,110,365 | 23,381,006 | 86.2% |
| Total RNA | EGFP100 pro-siRNA-2 | 22,690,638 | 19,433,997 | 85.6% |
| Total RNA | EGFPFL pro-siRNA-1 | 27,914,511 | 23,335,378 | 83.6% |
| Total RNA | EGFPFL pro-siRNA-2 | 21,572,278 | 18,178,029 | 84.3% |
| small RNA | EGFPFL/EGFPFL-1 | 3,291,738 | 3,119,677 | 94.8% |
| small RNA | EGFP100 | 2,967,297 | 1,488,213 | 50.2% |
| small RNA | LMNA | 1,659,890 | 1,382,441 | 83.3% |
| small RNA | TP53 | 5,446,487 | 4,462,318 | 81.9% |
| small RNA | PLK1 | 2,938,903 | 2,309,515 | 78.6% |
| small RNA | vif | 1,869,202 | 1,493,137 | 79.9% |
| small RNA | gagB200 | 5,326,736 | 3,640,886 | 68.4% |
| small RNA | gagB500 | 7,168,829 | 5,017,221 | 70.0% |
| small RNA | EGFPFL-2 | 5,507,507 | 4,075,642 | 74.0% |
| small RNA | EGFP Hotspot-1 | 6,483,321 | 5,425,661 | 83.7% |
| small RNA | EGFP Hotspot-2 | 6,485,138 | 4,019,427 | 62.0% |

TABLE 3

EGFPFL pro-siRNAs for testing strand bias

| Name | Sequence (5'-3') | SEQ ID NO | Direction | Start | Number of Reads | Ranking |
|---|---|---|---|---|---|---|
| Si1 | UAGUGGUUGUCGGGCAGCAGC | 7 | Antisense | 602 | 279598 | 2 |
| Si2 | UAUAGACGUUGUGGCUGUUG | 8 | Antisense | 457 | 1305273 | 1 |
| Si3 | UGGUCGAGCUGGACGGCGACG | 9 | Sense | 47 | 55643 | 11 |

TABLE 4

List of E. coli strains

| Name | Genotype | Source/reference |
|---|---|---|
| DH5α | fhuA2Δ(argF-lacZ)U169 phoA glnV44 Φ80 Δ(lacZ)M15 gyrA96 recA1 relA1 endA1 thi-1 hsdR17 | NEB (C2987) |
| T7 Express Iq | MiniF lacI$^q$(Cam$^R$)/fhuA2 lacZ::T7 gene1 [lon] ompT gal sulA11 R(mcr-73::miniTn10--Tet$^S$)2 [dcm] R(zgb-210::Tn10--Tet$^S$) endA1 Δ(mcrC-mrr)114::IS10 | NEB (C3016) |
| HT115(DE3) | W3110 rnc-14::ATnJO λDE3 | Timmons et al. (2001), gift of Gary Ruvkun |
| BL21(DE3) | fhuA2 [lon] ompT gal (λ DE3) [dcm] ΔhsdS λ DE3 = λ sBamHIo ΔEcoRI-B int::(lacI::PlacUV5::T7 gene1) i21 Δnin5 | NEB (C2527) |
| SK7622 | thyA715 Δrnc-38::Kmr | Babitzke et al. (1993), gift of Sidney Kushner |
| MG1655 ΔlacZYA | F-lambda-ilvG-rfb-50 rph-1 ΔlacZYA | Gift from S. Garrity |
| MG1655 ΔlacZYA rnc14 | F-lambda-ilvG-rfb-50 rph-1 ΔlacZYA Δrnc14 | This study |
| MG1655 ΔlacZYA rnc38 | F-lambda-ilvG-rfb-50 rph-1 ΔlacZYA Δrnc38 | This study |

TABLE 5

List of plasmids

| Name | Purpose |
|---|---|
| pcDNA3.1+ | Empty control plasmid |
| pcDNA3.1-TREX1-FLAG | For expression of TREX1-FLAG protein directed from the CMV promoter |
| pcDNA3.1-P19-FLAG | For expression of P19-FLAG from the CMV promoter |
| pcDNA3.1-His-P19 | For expression of His-P19 from the CMV promoter |
| pcDNA3.1-P19-3942-His | For expression of His-P19 3942 mutant from the CMV promoter |
| pcDNA3.1-P19-7172-His | For expression of His-P19 7172 mutant from the CMV promoter |
| pcDNA3.1-RNase III | For expression of FLAG tagged E. coli RNase III |
| pRSF-GST-P19-His | For expression of GST-P19-His from T7 promoter |
| pCDF-GST-P19-His | For expression of GST-P19-His from T7 promoter |
| pCDF-RNase III | For expression of FLAG tagged E. coli RNase III from T7 promoter |
| L4440-EGFP | For expression of double stranded eGFP RNA from convergent T7 promoters |
| pGEX-4T-1-P19-His | For expression of GST-P19-His from Tac promoter |
| pGEX-4T-1-P19-T7 | For expression of GST-P19-His from Tac promoter, and hairpin RNA from the T7 promoter |
| pGEX-4T-1-P19-T7-EGFPFL | For producing EGFPFL pro-siRNA |
| pGEX-4T-1-P19-T7-EGFP-Hotspot1 | For producing EGFP Hotspot1 pro-siRNA |
| pGEX-4T-1-P19-T7-EGFP-Hotspot2 | For producing EGFP Hotspot2 pro-siRNA |
| pGEX-4T-1-P19-T7-EGFP100 | For producing EGFP100 pro-siRNA |
| pGEX-4T-1-P19-T7-LMNA | For producing LMNA pro-siRNA |
| pGEX-4T-1-P19-T7-PLK1 | For producing PLK1 pro-siRNA |
| pGEX-4T-1-P19-T7-TP53 | For producing TP53 pro-siRNA |
| pGEX-4T-1-P19-T7-Vif | For producing HIV-vif pro-siRNA |
| pGEX-4T-1-P19-T7-GagB200 | For producing gagB200 pro-siRNA |
| pGEX-4T-1-P19-T7-GagB500 | For producing gagB500 pro-siRNA |
| pLIV-1 | Empty control plasmid |
| pLIV-1-His-P19 | For expression of His-P19 protein in L. monocytogenes |

TABLE 6

List of DNA oligonucleotides

| Name | Sequence (5'-3') | SEQ ID NO | Purpose |
|---|---|---|---|
| P19-F-NheI | AATCGCTAGCATGGAACGAGCTATACAAGGA | 10 | pcDNA3.1-P19-FLAG |
| P19-R-BamHI | AATCGGATCCCTCGCTTTCTTTTTCGAAGG | 11 | pcDNA3.1-P19-FLAG |
| P19NLS-F | AATCGGATCCGATCCAAAAAGAAGAGAAAGGTAGATCCAAAAAGAAGAGAAAGGTA | 12 | pcDNA3.1-P19-FLAG |

TABLE 6-continued

List of DNA oligonucleotides

| Name | Sequence (5'-3') | SEQ ID NO | Purpose |
|---|---|---|---|
| P19NLS-R | AATCCTCGAGTCACTTATCGTCGTCATCCTTGTAATCGCCTACCTTTCTCTTCTTTTT | 13 | pcDNA3.1-P19-FLAG |
| P19-F-His-NheI | AATCGCTAGCATGCACCACCACCACCACCACGCGGGCGAACGAGCTATACAAGGA | 14 | pcDNA3.1-P19-His |
| P19-R-BamHI | AATCGGATCCTCACTCGCTTTCTTTTTCGAAGG | 15 | pcDNA3.1-P19-His |
| P19W3942G-F | CCGAGTGGCACTGAGGGCCGGCTACATAACGATGAGACGAATTC | 16 | pcDNA3.1-P19-3942-His |
| P19W3942G-R | TAGCCGGCCCTCAGTGCCACTCGGACTTTCGTCAGGAAGTTTGA | 17 | pcDNA3.1-P19-3942-His |
| P19KR7172AG-F | GTTGTATTTGCGGGCTATCTCAGATACGACAGGACGGAAGCTTC | 18 | pcDNA3.1-P19-7172-His |
| P19KR7172AG-R | TCTGAGATAGCCCGCAAATACAACTTTCCCGAAACCCCAGCTTT | 19 | pcDNA3.1-P19-7172-His |
| P19F-XbaI | AATATCTAGAATGGAACGAGCTATACAAGGA | 20 | pLIV-1-P19-His |
| P19R-His-XbaI | AATCTCTAGATCAGTGGTGGTGGTGGTGGTG | 21 | pLIV-1-P19-His |
| P19-F-BamHI | AATCGGATCCATGGAACGAGCTATACAAGGA | 22 | pGEX-4T-1-P19-His |
| P19His-R-XhoI | AATCCTCGAGTCAGTGGTGGTGGTGGTGGTGCTCGCTTTCTTTTTCGAAGG | 23 | pGEX-4T-1-P19-His |
| mc-FLAG-NheI-F | ACTTGCTAGCATGGATTACAAGGATGACGACGATAAGAACCCCATCGTAATTAATCG | 24 | pcDNA3.1-RNase III and pCDF-RNase III |
| mc-BamHI-R | ATCGGATCCTCATTCCAGCTCCAGTTTTTTCAA | 25 | RNase III and pCDF-RNase III |
| His-T7-SacI | ATCGAGCTCCCCTATAGTGAGTCGTATTAGATTCAGTGGTGGTGGTGGTGT | 26 | pGEX-4T-1-P19-T7 |
| Linker3-F | ATGAATTCGTCGACACTGCGGCCGCTCTAGAGGGCCCGTTTAAACCCGCT | 27 | pGEX-4T-1-P19-T7 |
| Linker3-R | ATCTCGAGAATGAGCTCGCTGATCAGCGGGTTTAAACGGGCCCTCTAGAG | 28 | pGEX-4T-1-P19-T7 |
| GST-F-NdeI | ATCCCATATGTCCCCTATACTAGGTTATTG | 29 | pRSF-GST-P19-His, pCDF-GST-P19-His |
| His-R-XhoI | AATCCTCGAGTCAGTGGTGGTGGTGGTGGTG | 30 | pRSF-GST-P19-His, pCDF-GST-P19-His |
| EGFP-F-SacI | AATCGAGCTCCATGGTGAGCAAGGGCGAGGA | 31 | pGEX-4T-1-P19-T7-EGFPFL |
| EGFP-F-NotI | AATCGCGGCCGCATGGTGAGCAAGGGCGAGGA | 32 | pGEX-4T-1-P19-T7-EGFPFL |
| EGFP-R-SalI | AATCGTCGACCTACTTGTACAGCTCGTCCA | 33 | pGEX-4T-1-P19-T7-EGFPFL |
| EGFP-F-XhoI | AATCCTCGAGCTACTTGTACAGCTCGTCCA | 34 | pGEX-4T-1-P19-T7-EGFPFL, EGFP northern blot probe |

TABLE 6-continued

List of DNA oligonucleotides

| Name | Sequence (5'-3') | SEQ ID NO | Purpose |
|---|---|---|---|
| EGFPHS1-F-NotI | ATCCGCGGCCGCATGGTGAGCAAGGGCGAGGAG | 35 | pGEX-4T-1-P19-T7-EGFP-Hotspot1 |
| EGFPHS1-F-SacI | ATCGAGCTCATGGTGAGCAAGGGCGAGGAG | 36 | pGEX-4T-1-P19-T7-EGFP-Hotspot1 |
| EGFPHS1-R-SalI | ATCGTCGACCAGGGTGTCGCCCTCGAACTT | 37 | pGEX-4T-1-P19-T7-EGFP-Hotspot1 |
| EGFPHS1-R-XhoI | ATCCTCGAGCAGGGTGTCGCCCTCGAACTT | 38 | pGEX-4T-1-P19-T7-EGFP-Hotspot1 |
| EGFPHS2-F-NotI | ATCCGCGGCCGCGTGAACCGCATCGAGCTGAAG | 39 | pGEX-4T-1-P19-T7-EGFP-Hotspot2 |
| EGFPHS2-F-SacI | ATCGAGCTCGTGAACCGCATCGAGCTGAAG | 40 | pGEX-4T-1-P19-T7-EGFP-Hotspot2 |
| EGFPHS2-R-SalI | ATCGTCGACCTACTTGTACAGCTCGTCCAT | 41 | pGEX-4T-1-P19-T7-EGFP-Hotspot2 |
| EGFPHS2-R-XhoI | ATCCTCGAGCTACTTGTACAGCTCGTCCAT | 42 | pGEX-4T-1-P19-T7-EGFP-Hotspot2 |
| EGFP100-F-SacI | AATCGAGCTCCCGCTACCCCGACCACATGAA | 43 | pGEX-4T-1-P19-T7-EGFP100 |
| EGFP100-F-NotI | AATCCGCGGCCGCCCGCTACCCCGACCACATGAA | 44 | pGEX-4T-1-P19-T7-EGFP100 |
| EGFP100-R-SalI | AATCGTCGACGTTGCCGTCGTCCTTGAAGAA | 45 | pGEX-4T-1-P19-T7-EGFP100 |
| EGFP100-R-XhoI | AATCCTCGAGGTTGCCGTCGTCCTTGAAGAA | 46 | pGEX-4T-1-P19-T7-EGFP100 |
| TP53-R-SalI | AATCGTCGACCAACCTCAGGCGGCTCATAGG | 47 | pGEX-4T-1-P19-T7-TP53 |
| TP53-RXhoI | AATCCTCGAGCAACCTCAGGCGGCTCATAGG | 48 | pGEX-4T-1-P19-T7-TP53 |
| TP53-F-Not | AATCGCGGCCGCTACTCCCCTGCCCTCAACAAGATG | 49 | pGEX-4T-1-P19-T7-TP53 |
| TP53-F-SacI | AATCGAGCTCTACTCCCCTGCCCTCAACAAGATG | 50 | pGEX-4T-1-P19-T7-TP53 |
| HIV-Vif-F-SacI | AATCGAGCTCGGAAAACAGATGGCAGGTGATG | 51 | pGEX-4T-1-P19-T7-Vif |
| HIV-Vif-F-NotI | AATCGCGGCCGCGGAAAACAGATGGCAGGTGATG | 52 | pGEX-4T-1-P19-T7-Vif |
| HIV-Vif-R-SalI | AATCGTCGACCTAGTGTCCATTCATTGTGTGG | 53 | pGEX-4T-1-P19-T7-Vif |
| HIV-Vif-R-XhoI | AATCCTCGAGCTAGTGTCCATTCATTGTGTGG | 54 | pGEX-4T-1-P19-T7-Vif |
| LaminAC-F-SacI | AATCGAGCTCCAAGACCCTTGACTCAGTAGCC | 55 | pGEX-4T-1-P19-T7-LMNA |
| LaminAC-F-NotI | AATCGCGGCCGCCAAGACCCTTGACTCAGTAGCC | 56 | pGEX-4T-1-P19-T7-LMNA |
| LaminAC-R-SalI | AATCGTCGACCAGCTCCTTCTTATACTGCTCCA | 57 | pGEX-4T-1-P19-T7-LMNA |
| LaminAC-R-XhoI | AATCCTCGAGCAGCTCCTTCTTATACTGCTCCA | 58 | pGEX-4T-1-P19-T7-LMNA |
| PLK1-F-NotI | AATCGCGGCCGCTCTCTGCTGCTCAAGCCGCAC | 59 | pGEX-4T-1-P19-T7-PLK1 |

TABLE 6-continued

List of DNA oligonucleotides

| Name | Sequence (5'-3') | SEQ ID NO | Purpose |
|---|---|---|---|
| PLK1-F-SacI | AATCGAGCTCTCTCTGCTGCTCAAGCCGCAC | 60 | pGEX-4T-1-P19-T7-PLK1 |
| PLK1-R-SalI | AATCGTCGACAAGTCTCAAAAGGTGGTTTGCC | 61 | pGEX-4T-1-P19-T7-PLK1 |
| PLK1-R-XhoI | AATCCTCGAGAAGTCTCAAAAGGTGGTTTGCC | 62 | pGEX-4T-1-P19-T7-PLK1 |
| Gag200-FNotI | ATCCGCGGCCGCTGTGGCAAAGAAGGGCACACAG | 63 | pGEX-4T-1-P19-T7-GagB200 |
| Gag200-FSacI | ATCGAGCTCTGTGGCAAAGAAGGGCACACAG | 64 | pGEX-4T-1-P19-T7-GagB200 |
| Gag200-RSalI | ATCGTCGACTCTTCTGGTGGGGCTGTTGGCT | 65 | pGEX-4T-1-P19-T7-GagB200 |
| Gag200-RXhoI | ATCCTCGAGTCTTCTGGTGGGGCTGTTGGCT | 66 | pGEX-4T-1-P19-T7-GagB200 |
| Gag500-FNotI | ATCCGCGGCCGCAAGCATTGGGACCAGCGGCTAC | 67 | pGEX-4T-1-P19-T7-GagB500 |
| Gag500-FSacI | ATCGAGCTCAAGCATTGGGACCAGCGGCTAC | 68 | pGEX-4T-1-P19-T7-GagB500 |
| Gag500-RSalI | ATCGTCGACTTATTGTGACGAGGGGTCGTTG | 69 | pGEX-4T-1-P19-T7-GagB500 |
| Gag500-RXhoI | ATCCTCGAGTTATTGTGACGAGGGGTCGTTG | 70 | pGEX-4T-1-P19-T7-GagB500 |
| SiSEQ1 | CAAGCAGAAGACGGCATACGA | 71 | Deep sequencing library PCR |
| SiSEQ2 | AATGATACGGCGACCACCGACAGGTTCAGAGTTCTACAGTCCGA | 72 | Deep sequencing library PCR |
| GAPDH For | CTGGGCTACACTGAGCACC | 73 | |
| GAPDH Rev | AAGTGGTCGTTGAGGGCAATG | 126 | |
| IL12 For | CACTCCCAAAACCTGCTGCTGAG | 74 | qRT-PCR |
| IL12 Rev | TCTCTTCAGAAGTGCAAGGGTA | 75 | qRT-PCR |
| IL6 For | GATGAGTACAAAAGTCCTGATCCA | 76 | qRT-PCR |
| IL6 Rev | CTGCAGCCACTGGTTCTGT | 77 | qRT-PCR |
| IL8 For | AGACAGCAGAGCACACAAGC | 78 | qRT-PCR |
| IL8 Rev | ATGGTTCCTTCCGGTGGT | 79 | qRT-PCR |
| TNFA For | CAGCCTCTTCTCCTTCCTGAT | 80 | qRT-PCR |
| TNFA Rev | GCCAGAGGGCTGATTAGAGA | 81 | qRT-PCR |
| Vif For | AGGGAAAGCTAGGGGATGGTTTT | 82 | qRT-PCR |
| Vif Rev | CCCAAATGCCAGTCTCTTTCTCC | 83 | qRT-PCR |
| IN22-Vif For | AAAGAGAGCTAATGGATGGTTTT | 84 | qRT-PCR |
| IN22-Vif Rev | CCCAAATGCCAATCTCTTTCCCC | 85 | qRT-PCR |
| UG29-Vif For | AAAGAAAGCTACTGGTTGGTGTT | 86 | qRT-PCR |
| UG29-vif Rev | CCCAAGTGCCAGTCTTTTTCTCC | 87 | qRT-PCR |
| GagABC For | CCTAGGAAAAAGGGCTGTTGGA | 88 | qRT-PCR |
| GagABC Rev | AGGAAGGCCAGATCTTCCCTAAA | 89 | qRT-PCR |

TABLE 6-continued

List of DNA oligonucleotides

| Name | Sequence (5'-3') | SEQ ID NO | Purpose |
|---|---|---|---|
| IFIT1For | GCCACAAAAAATCACAAGCCA | 90 | qRT-PCR |
| IFIT1Rev | CCATTGTCTGGATTTAAGCGG | 91 | qRT-PCR |
| LMNA For | AGCAGCGTGAGTTTGAGAGC | 92 | qRT-PCR |
| LMNA Rev | CCAGCTTGGCAGAATAAGTCTT | 93 | qRT-PCR |
| PLK1 For | CGAGGACAACGACTTCGTGTT | 94 | qRT-PCR |
| PLK1 Rev | ACAATTTGCCGTAGGTAGTATCG | 95 | qRT-PCR |
| TP53 For | ACAGCTTTGAGGTGCGTGTTT | 96 | qRT-PCR |
| TP53 Rev | CCCTTTCTTGCGGAGATTCTCT | 97 | qRT-PCR |
| eGFP For | ACGTAAACGGCCACAAGTTC | 98 | qRT-PCR |
| eGFP Rev | AAGTCGTGCTGCTTCATGTG | 99 | qRT-PCR |
| EGFP-T7-F | ACTAATACGACTCACTATAGGGATGGTGAGCAAGGGCGAGGA | 100 | EGFP northern blot probe |
| EGFPFL-si1-F | CGTGCTGCTGCCCGACAACCACTACCT | 101 | Solution hybridization |
| EGFPFL-si1-R | GAGGTAGTGGTTGTCGGGCAGCAGCACG | 102 | Solution hybridization |
| EGFPFL-si2-F | CTACAACAGCCACAACGTCTATATCA | 103 | Solution hybridization |
| EGFPFL-si2-R | TGATATAGACGTTGTGGCTGTTGTAG | 104 | Solution hybridization |
| EGFPFL-si3-F | CCTGGTCGAGCTGGACGGCGACGTAA | 105 | Solution hybridization |
| EGFPFL-si3-R | TTACGTCGCCGTCCAGCTCGACCAGG | 106 | Solution hybridization |
| ACH-5 | TATGAGGAACAGATTTTCTCACATGG | 107 | Control oligo for solution hybridization |

TABLE 7

RNA adapters for small RNA deep sequencing libraries

| Name | Sequence (5'-3') | SEQ ID NO | Purpose |
|---|---|---|---|
| 5ADPT-2 | GUUCAGAGUUCUACAGUCCGACGAUCGCUU | 108 | 5' adapter for EGFPFL |
| 5ADPT-3 | GUUCAGAGUUCUACAGUCCGACGAUCGAGU | 109 | 5' adapter for EFGP100 |
| 5ADPT-5 | GUUCAGAGUUCUACAGUCCGACGAUCCGUU | 110 | 5' adapter for PLK1 |
| 5ADPT-6 | GUUCAGAGUUCUACAGUCCGACGAUCCCGU | 111 | 5' adapter for LMNA |
| 5ADPT-7 | GUUCAGAGUUCUACAGUCCGACGAUCCACU | 112 | 5' adapter for HIV-Vif |
| 3ADPT | UCGUAUGCCGUCUUCUGCUUGUidT | 113 | 3' adapter for all libraries |

What is claimed herein is:

1. A method of producing one or more siRNA species which can inhibit the expression of a target RNA, the method comprising:
   culturing a bacterial cell comprising:
   a. a viral siRNA-binding polypeptide and
   b. a dsRNA comprising a nucleic acid sequence substantially complementary to a target RNA
   under conditions suitable for the production of siRNAs.

2. The method of claim 1, further comprising a second step of isolating the viral siRNA-binding polypeptide and eluting the siRNAs bound to the viral siRNA-binding polypeptide.

3. The method of claim 2, further comprising purifying the siRNAs eluted from the viral siRNA-binding polypeptide by HPLC.

4. The method of claim 1, further comprising contacting the cell with one or more modified nucleotides before or during the culturing step.

5. The method of claim 1, wherein the dsRNA is exogenous to the bacterial cell.

6. The method of claim 1, wherein the viral siRNA-binding polypeptide comprises a purification tag.

7. The method of claim 1, wherein the viral siRNA-binding polypeptide is encoded by a nucleic acid.

8. The method of claim 1, wherein the viral siRNA-binding polypeptide is selected from the group consisting of: p19 polypeptide; tombusvirus p19 polypeptide; B2 polypeptide; HC-Pro polypeptide; p38 polypeptide; p122 polypeptide; p130 polypeptide; p21 polypeptide; p1b polypeptide; and NS3 polypeptide.

9. The method of claim 1, wherein the dsRNA is greater than 21 nucleotides in length.

10. The method of claim 1, wherein the dsRNA is a hairpin RNA.

11. The method of claim 1, wherein the bacterial cell expresses an RNase III polypeptide.

12. The method of claim 1, wherein the bacterial cell expresses an RNase III polypeptide encoded by an exogenous nucleic acid sequence.

13. The method of claim 1, wherein the bacterial cell is an *Escherichia coli* cell.

14. The method of claim 1, wherein at least one of the viral siRNA-binding polypeptide and the dsRNA are constitutively expressed.

15. The method of claim 1, wherein at least one of the viral siRNA-binding polypeptide and the dsRNA are inducibly expressed.

16. The method of claim 1, wherein the DNA encoding at least one of the viral siRNA-binding polypeptide or the dsRNA is part of a plasmid.

17. The method of claim 1, wherein the dsRNA comprises nucleic acid sequences substantially complementary to a multiplicity of target RNAs.

* * * * *